(12) United States Patent
Wezeman et al.

(10) Patent No.: US 9,291,630 B1
(45) Date of Patent: Mar. 22, 2016

(54) RP-HPLC METHOD FOR THE ANALYSIS AND QUANTIFICATION OF PANCREATIN ACTIVE PHARMACEUTICAL AGENTS

(75) Inventors: Rachel Wezeman, Middleton, WI (US);
Lin Rao, Madison, WI (US); Kirk Cryer, Madison, WI (US); Yan Wang, Middleton, WI (US)

(73) Assignee: Scientific Protein Laboratories, LLC, Waunakee, WI (US)

( * ) Notice: Subject to any disclaimer, the term of this patent is extended or adjusted under 35 U.S.C. 154(b) by 31 days.

(21) Appl. No.: 13/598,493

(22) Filed: Aug. 29, 2012

Related U.S. Application Data

(60) Provisional application No. 61/528,582, filed on Aug. 29, 2011.

(51) Int. Cl.
*G01N 33/68* (2006.01)
*G01N 33/566* (2006.01)
*C07K 14/62* (2006.01)
*C07K 7/06* (2006.01)
*C07K 9/00* (2006.01)
*C07K 7/02* (2006.01)

(52) U.S. Cl.
CPC .......... *G01N 33/6893* (2013.01); *G01N 33/566* (2013.01); *C07K 7/02* (2013.01); *C07K 7/06* (2013.01); *C07K 9/001* (2013.01); *C07K 14/62* (2013.01)

(58) Field of Classification Search
CPC ............... G01N 33/6893; G01N 2800/042; G01N 2800/52; G01N 2800/14; G01N 33/566; G01N 33/57449; G01N 33/576; G01N 33/57484; G01N 33/543; G01N 33/588; C07K 14/62; C07K 1/1077; C07K 7/06; C07K 9/001; C07K 7/02; C07K 7/08
See application file for complete search history.

(56) References Cited

U.S. PATENT DOCUMENTS 7,125,492 B2 * 10/2006 Bidlingmeyer et al. ...... 210/635
7,479,378 B2    1/2009 Potthoff et al.
2005/0112743 A1 *  5/2005 Potthoff et al. ............... 435/186

* cited by examiner

*Primary Examiner* — Alexander Kim
(74) *Attorney, Agent, or Firm* — Reinhart Boerner Van Deuren s.c.

(57) ABSTRACT

Disclosed is a method for the separation, identification and quantification of multiple proteins in pancreatin active pharmaceutical ingredient samples.

11 Claims, 38 Drawing Sheets
(34 of 38 Drawing Sheet(s) Filed in Color)

FIG 3

| 1208 | Peak Area | | | | | | Relative amount (%)* | | | | | |
|---|---|---|---|---|---|---|---|---|---|---|---|---|
| peak # | Injection 1 | Injection 2 | 3 | Average | Stdev | %RSD | 1 | 2 | 3 | Ave. | Stdev | %RSD |
| 1+2 | 37,374 | 36,649 | 36,550 | 36,858 | 450 | 1.22 | 0.96 | 0.96 | 0.95 | 0.95 | 0.01 | 0.53 |
| 3 | 16,864 | 16,879 | 16,741 | 16,547 | 461 | 2.78 | 0.43 | 0.44 | 0.43 | 0.44 | 0.00 | 0.98 |
| 4+5 | 89,308 | 88,433 | 92,815 | 90,185 | 2,319 | 2.57 | 2.28 | 2.31 | 2.40 | 2.33 | 0.05 | 2.18 |
| 6+7 | 382,130 | 383,550 | 380,797 | 382,159 | 1,377 | 0.36 | 9.77 | 10.02 | 9.85 | 9.88 | 0.11 | 1.07 |
| 8+9 | 230,447 | 229,506 | 232,063 | 230,672 | 1,293 | 0.56 | 5.89 | 6.00 | 6.00 | 5.96 | 0.05 | 0.88 |
| 10 | 111,162 | 115,659 | 109,462 | 112,094 | 3,202 | 2.86 | 2.84 | 3.02 | 2.83 | 2.90 | 0.09 | 3.01 |
| 11+12 | 189,480 | 186,844 | 190,054 | 188,793 | 1,712 | 0.91 | 4.84 | 4.88 | 4.92 | 4.88 | 0.03 | 0.63 |
| 13+14 | 644,932 | 648,821 | 646,489 | 646,747 | 1,957 | 0.30 | 16.48 | 16.95 | 16.73 | 16.72 | 0.19 | 1.14 |
| 15 | 339,516 | 337,198 | 335,648 | 337,454 | 1,947 | 0.58 | 8.68 | 8.81 | 8.69 | 8.72 | 0.06 | 0.70 |
| 16 | 155,427 | 153,991 | 156,173 | 155,197 | 1,109 | 0.71 | 3.97 | 4.02 | 4.04 | 4.01 | 0.03 | 0.72 |
| 17+18 | 56,362 | 535,06 | 54,359 | 54,742 | 1,466 | 2.68 | 1.44 | 1.40 | 1.41 | 1.42 | 0.02 | 1.30 |
| 19+20 | 583,605 | 565,360 | 534,338 | 561,101 | 24,908 | 4.44 | 14.92 | 14.77 | 13.83 | 14.50 | 0.48 | 3.33 |
| 21 | 46,819 | 44,999 | 46,784 | 138,602 | 1,041 | 0.75 | 1.20 | 1.18 | 1.21 | 1.19 | 0.01 | 1.20 |
| 22 | 246,726 | 235,299 | 240,858 | 240,961 | 5,714 | 2.37 | 6.31 | 6.15 | 6.23 | 6.23 | 0.06 | 1.04 |
| 23 | 529,739 | 500,965 | 530,562 | 520,422 | 16,855 | 3.24 | 13.54 | 13.09 | 13.73 | 13.45 | 0.27 | 2.00 |
| 24 | 146,137 | 134,002 | 151,523 | 143,887 | 8,975 | 6.24 | 3.74 | 3.50 | 3.92 | 3.72 | 0.17 | 4.62 |
| 25 | 106,459 | 95,785 | 109,387 | 103,877 | 7,159 | 6.89 | 2.72 | 2.50 | 2.83 | 2.68 | 0.14 | 5.08 |

FIG 5

| 1208 Peak # | Retention Time (min) | MW (kDa) | Relative amount* (%) | 1208 Peak # | Retention Time (min) | MW (kDa) | Relative amount (%) |
|---|---|---|---|---|---|---|---|
| Void | 3.08 | 2.8 | 100 | P14 | 24.75 | 27.6 | 35 |
| P1/2 | 11.8/12.03 | 14.8 | 90 | | | 24.4 | 41 |
| | | 5.8 | 10 | | | 13.2 | 10 |
| P3 | 14.95 | 12.5 | 100 | | | 7.8 | 14 |
| P4/5 | 16.63/16.95 | 15.8 | 25 | P15 | 25.57 | 24.4 | 50 |
| | | 11.5 | 39 | | | 13.2 | 10 |
| | | 7.1 | 36 | | | 7.8 | 40 |
| P6 | 17.36 | 24.3 | 65 | P16 | 26.45 | 24.4 | 72 |
| | | 12.2 | 20 | | | 7.8 | 28 |
| | | 8.2 | 15 | P17 | 27.16 | 24.4 | 100 |
| P7 | 17.59 | 24.3 | 90 | P18 | 28.26 | 24.4 | 100 |
| P6/7 | | 24.3 | 65 | P19 | 29.48 | 54.7 | 33 |
| | | 12.2 | 19 | | | 47.1 | 10 |
| | | 8.2 | 15 | | | 40.2 | 29 |
| P8 | 19.37 | 25.4 | 100 | | | 27.7 | 14 |
| P9 | 19.79 | 25.4 | 100 | | | 16.8 | 14 |
| P8/9 | | 25.4 | 100 | P20 | 30.62 | 54.7 | 31 |
| P10 | 20.92 | 49.9 | 57 | | | 47.1 | 33 |
| | | 23.8 | 43 | | | 27.7 | 15 |
| P11 | 22.56 | 49.9 | 10 | | | 24.4 | 20 |
| | | 40.9 | 24 | P21 | 33.77 | 54.7 | 36 |
| | | 23.8 | 46 | | | 47.1 | 38 |
| | | 13.5 | 20 | | | 24.4 | 26 |
| P12 | 22.92 | 49.9 | 7 | P22 | 36.04 | 54.7 | 12 |
| | | 40.9 | 18 | | | 36.1 | 27 |
| | | 27.6 | 23 | | | 35.2 | 45 |
| | | 23.8 | 27 | | | 24.4 | 16 |
| | | 13.5 | 25 | P23 | 40.06 | 54.4 | 27 |
| P11/12 | | 49.9 | 10 | | | 35.3 | 37 |
| | | 40.9 | 20 | | | 24.4 | 36 |
| | | 27.6 | 25 | P24-25 | 40.60 | 54.4 | 28 |
| | | 23.8 | 25 | | | 35.3 | 49 |
| | | 13.55 | 20 | | | 24.4 | 23 |
| P13 | 24.15 | 27.6 | 100 | P25 | 42.02 | 35.3 | 46 |
| | | | | | | 24.4 | 11 |
| | | | | | | 24.4 | 11 |

FIG 9
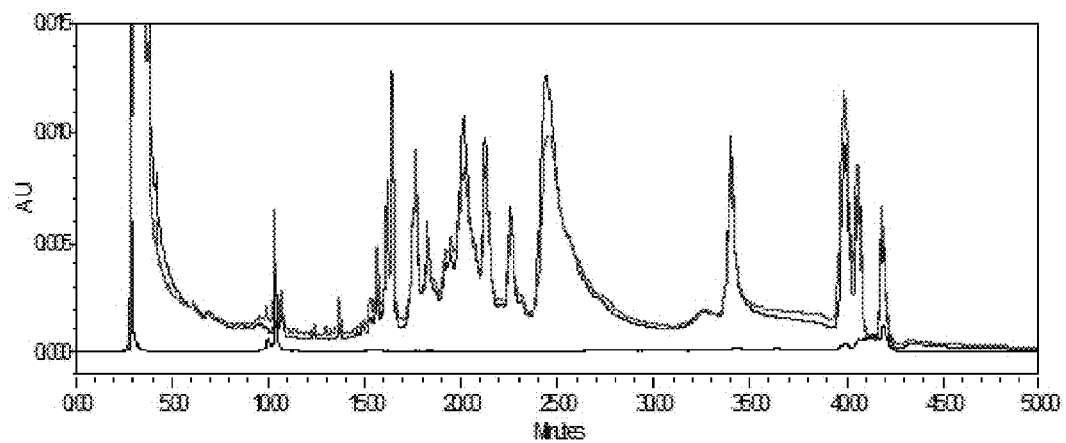
a
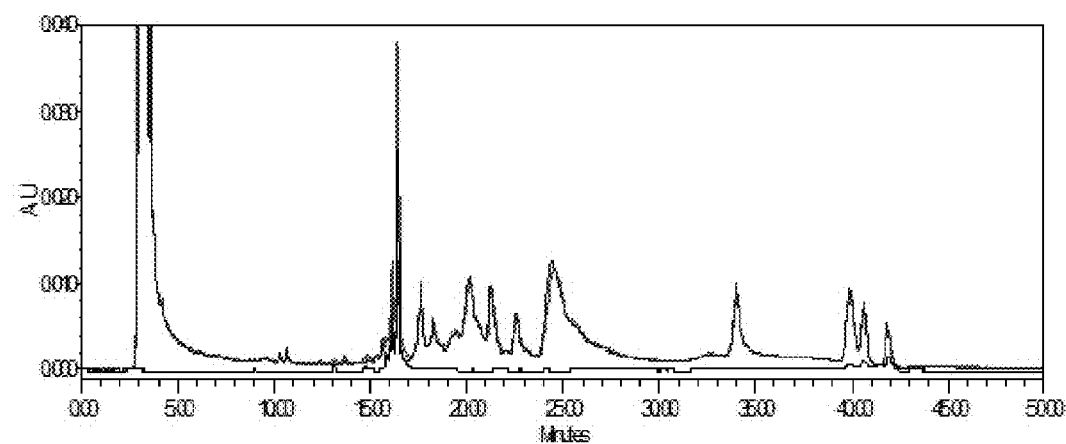
b

FIG 9 - CONT.
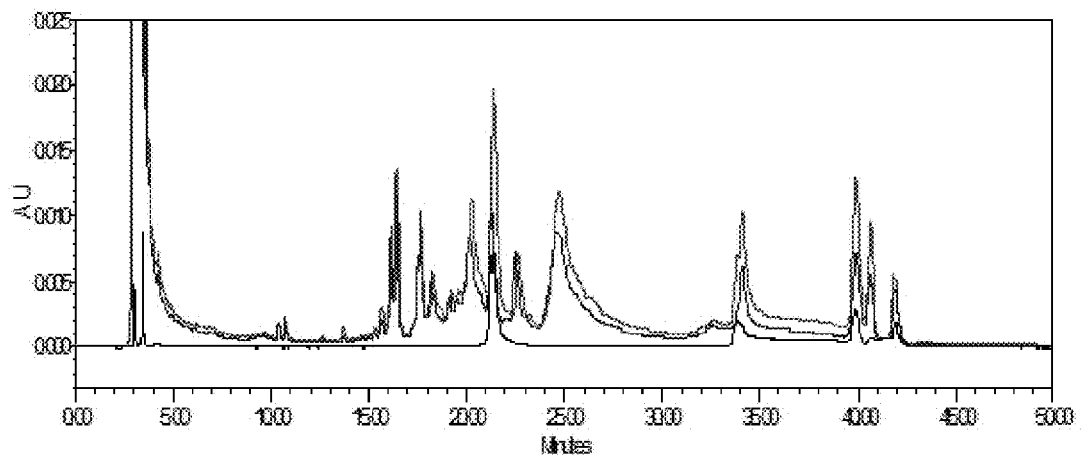
c
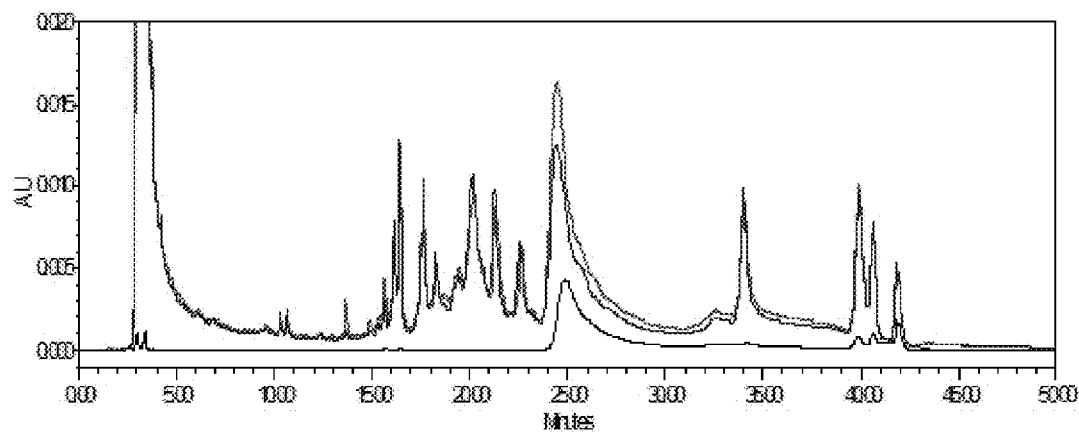
d

FIG 10

| Peak # | ID | Match to Sequence ID | Score* | MW (kDa) Observed | Expected | Detected by antibody against |
|---|---|---|---|---|---|---|
| P-1/2 | PLA₂ | gi\|129436 | 516 | 14.8 | 13.959 | PLA₂ |
|  | Colipase | gi\|47523482 | 227 | 5.8 | 12.132 |  |
| 3 | Lipase | gi\|67161 | 147 | 12.5 | 49.894 | Lipase |
| P-4 & 5 | ☐-Amylase, Chain A | gi\|62738255 | 138 | 15.8 | 55.381 |  |
|  | Trypsin, Chain E | gi\|3318722 | 120 | 11.5 | 23.457 |  |
|  | ☐-Amylase | gi\|2098469 | 132 | 7.1 | 55.325 |  |
| P-6&7 | Trypsin | gi\|136429 | 296 | 24.3 | 24.394 | Trypsin |
| P-8&9 | Elastase II | gi\|47523026 | 405 | 25.4 | 28.681 | Chymotrypsin, Elastase |
| P-10 | Lipase | gi\|67161 | 486 | 49.9 | 49.894 | Lipase |
|  | Chymotrypsin-like | gi\|73957472 | 129 | 23.8 | 28.200 | Chymotrypsin |
| P-11 | Lipase | gi\|67161 | 486 | 49.9 | 49.894 | Lipase |
|  | Lipase | gi\|67161 | 792 | 40.9 | 49.894 | Lipase |
|  | Chymotrypsin-like | gi\|73957472 | 129 | 23.8 | 28.200 | Chymotrypsin |
|  | Lithostathine | gi\|3024090 | 104 | 13.5 | 13.140 |  |
| P-12 | Lipase | gi\|67161 | 486 | 49.9 | 49.894 | Lipase |
|  | Lipase | gi\|67161 | 792 | 40.9 | 49.894 | Lipase |
|  | Lipase | gi\|67161 | 100 | 27.6 | 49.894 | Lipase |
|  | Chymotrypsin-like | gi\|73957472 | 129 | 23.8 | 28.200 | Chymotrypsin |
|  | Lithostathine | gi\|3024090 | 104 | 13.5 | 13.140 |  |
| P-13 | Chymotrypsin family | N/A | 86 | 27.6 |  | Chymotrypsin |
|  | Lipase | gi\|67161 | 486 | 49.9 | 49.894 | Lipase |
|  | Lipase | gi\|67161 | 100 | 27.6 | 49.894 | Lipase |
| P-14 | Chymotrypsin family | N/A | 86 | 27.6 |  | Chymotrypsin |
|  | Elastase | gi\|4930034 | 281 | 24.4 | 25.890 | Elastase |
|  | Elastase | gi\|7546312 | 461 | 13.2 | 15.904 | Elastase |
|  | Lipase | gi\|67161 | 486 | 49.9 | 49.894 | Lipase |
|  | Lipase | gi\|67161 | 100 | 27.6 | 49.894 | Lipase |
|  | Colipase | gi\|47523482 | 616 | 7.8 | 12.132 |  |
| P-15&16 | Elastase | gi\|7546312 | 678 | 24.4 | 25.890 | Elastase |
|  | Elastase | gi\|7546312 | 461 | 13.2 | 15.904 |  |
|  | Colipase | gi\|47523482 | 616 | 7.8 | 12.132 |  |
| P-17 & 18 | Elastase | gi\|7546312 | 414 | 24.4 | 25.890 | Elastase |
| P-19 | Alpha-Amylase | gi\|2780980 | 828 | 54.7 | 55.310 | Amylase |
|  | Alpha-Amylase | gi\|2780980 | 584 | 47.1 | 55.310 | Amylase |
|  | Alpha-Amylase | gi\|2780980 | 285 | 40.2 | 55.310 | Amylase |
|  | Alpha-Amylase | gi\|47523476 | 757 | 27.7 | 57.050 | Amylase |
|  | Elastase | gi\|7546312 | 414 | 24.4 | 25.89 | Elastase |
| P-20&21 | Alpha-Amylase | gi\|2780980 | 828 | 54.7 | 55.310 | Amylase |
|  | Alpha-Amylase | gi\|2780980 | 584 | 47.1 | 55.310 | Amylase |
|  | Alpha-Amylase | gi\|2780980 | 285 | 40.2 | 55.310 | Amylase |
|  | Elastase 1 | gi\|335937 | 286 | 24.4 | 28.865 |  |
| P-22 | Alpha-Amylase | gi\|2780980 | 584 | 54.7 | 55.310 | Amylase |
|  | CBP-B | gi\|5457422 | 239 | 36.1 | 47.351 | CBP-B |
|  | CBP-A | gi\|47523568 | 653 | 35.2 | 47.206 | CBP-B |
|  | Elastase 1 | gi\|335937 | 286 | 24.4 | 28.865 |  |
| P-23 to 25 | Alpha-Amylase | gi\|2780980 | 584 | 54.7 | 55.310 |  |
|  | CBP-A | gi\|47523568 | 653 | 35.3 | 47.206 | CBP-B |
|  | Elastase 1 | gi\|335937 | 286 | 24.4 | 28.865 |  |

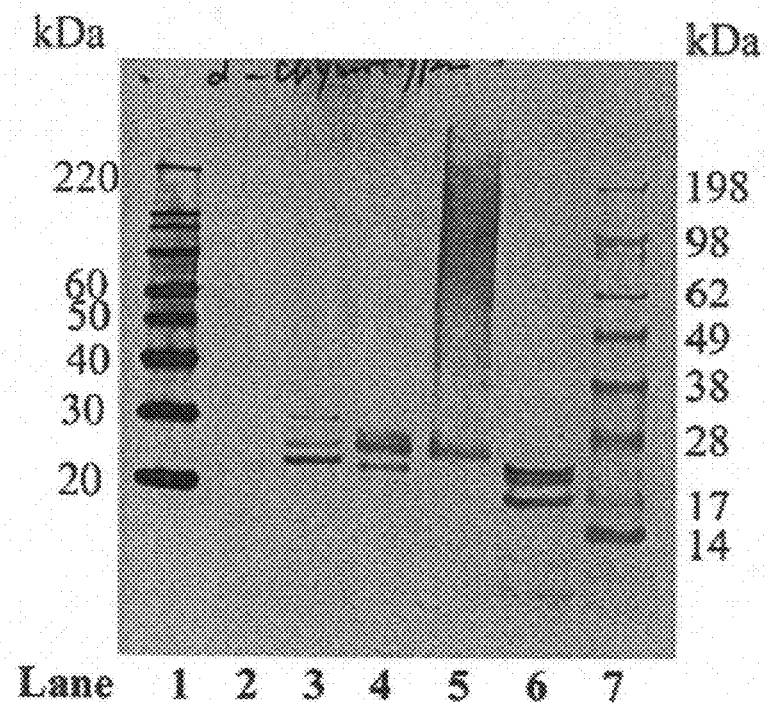

Lane# Sample ID

1&10 SeeBlue
2    Sigma Colipase
3    EPC Colipase
4    BM Colipase
5    BM Colipase-1
6    BM Colipase-2
7    BM Colipase-3
8    EPC CBP-B
9    Sigma CBP-B

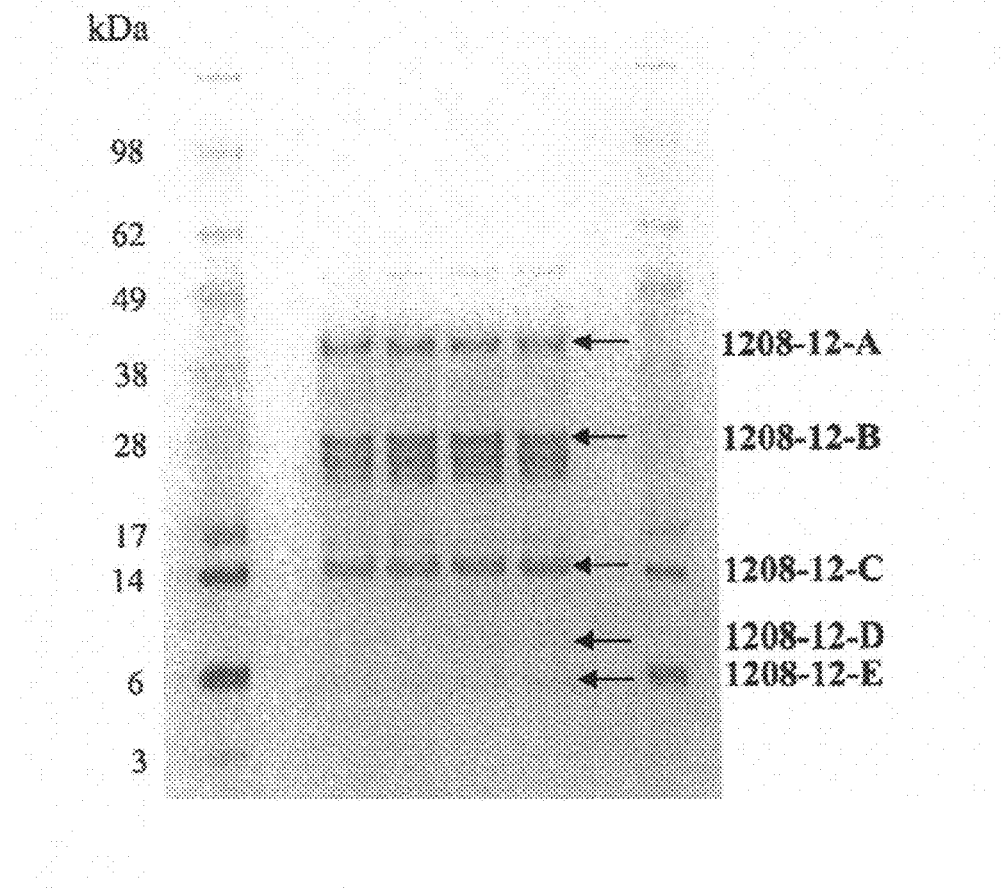

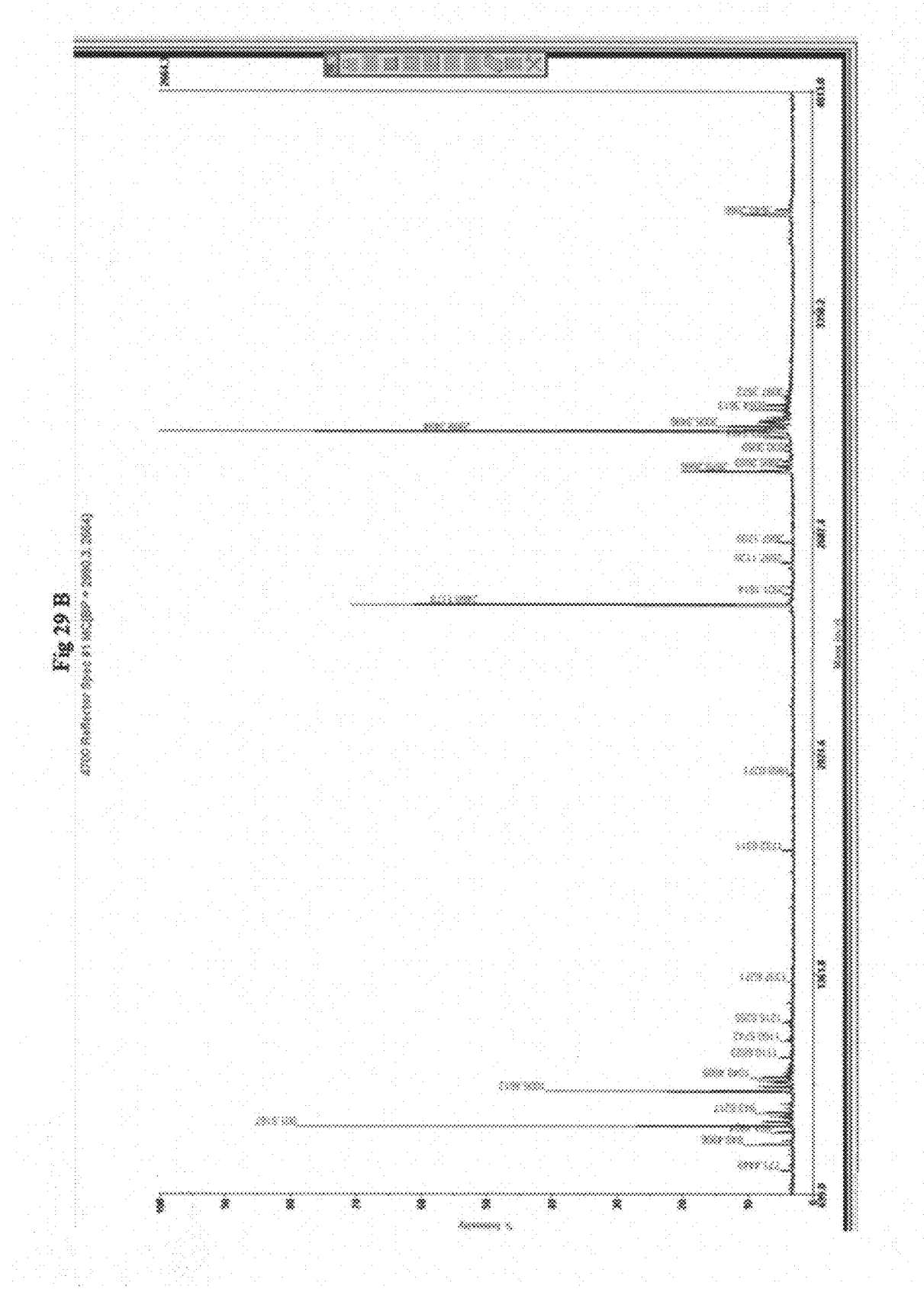

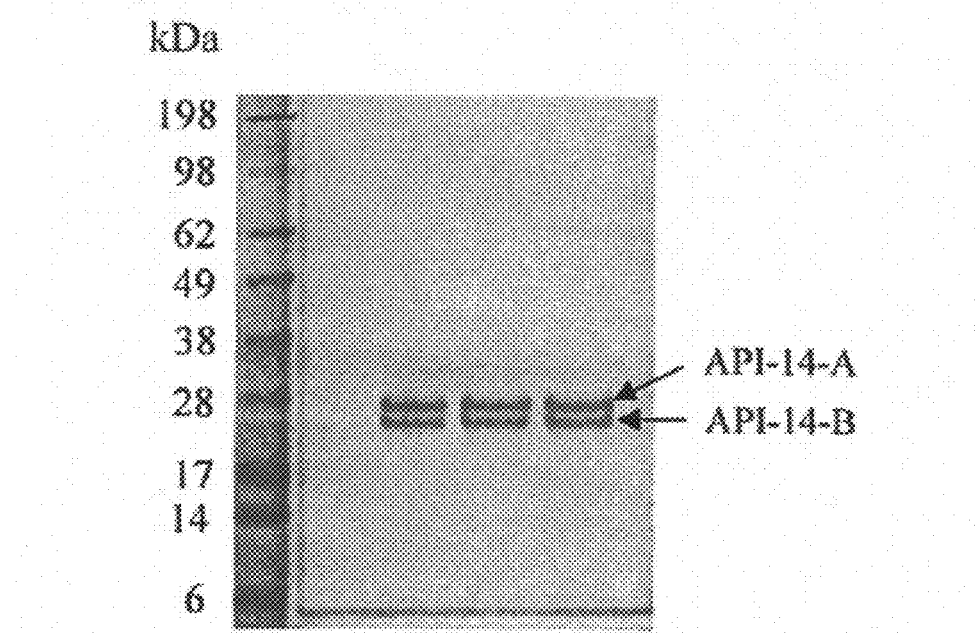

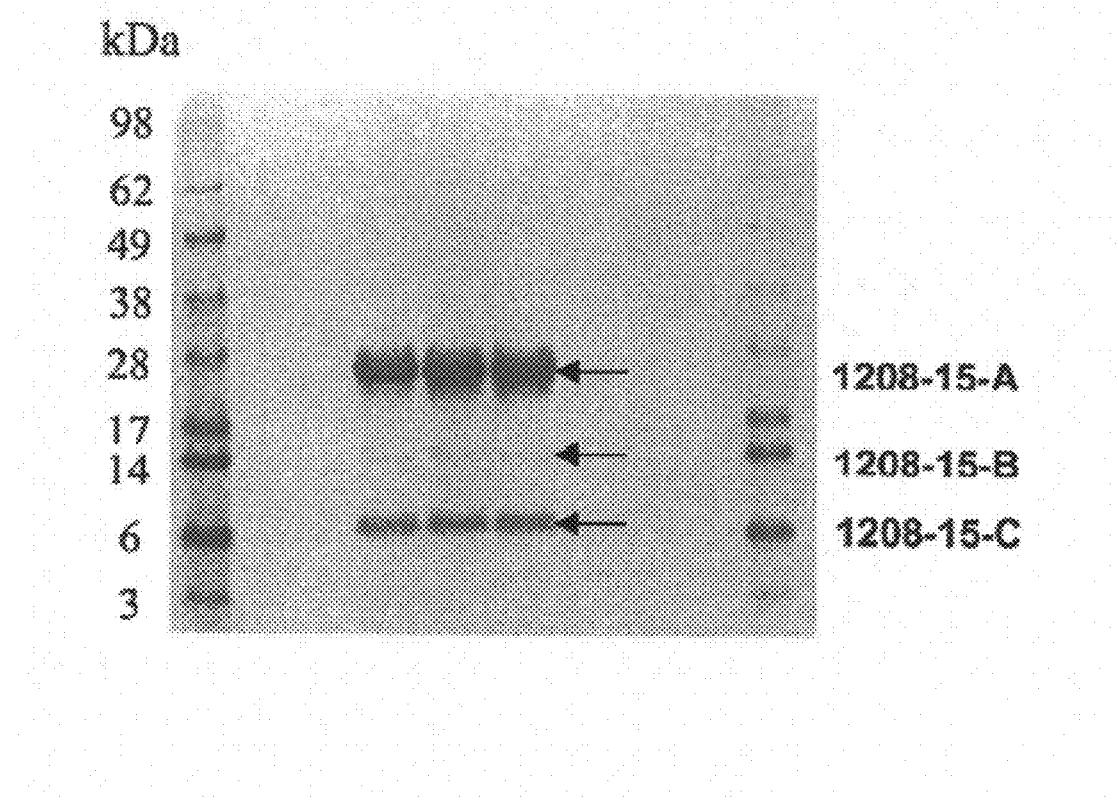

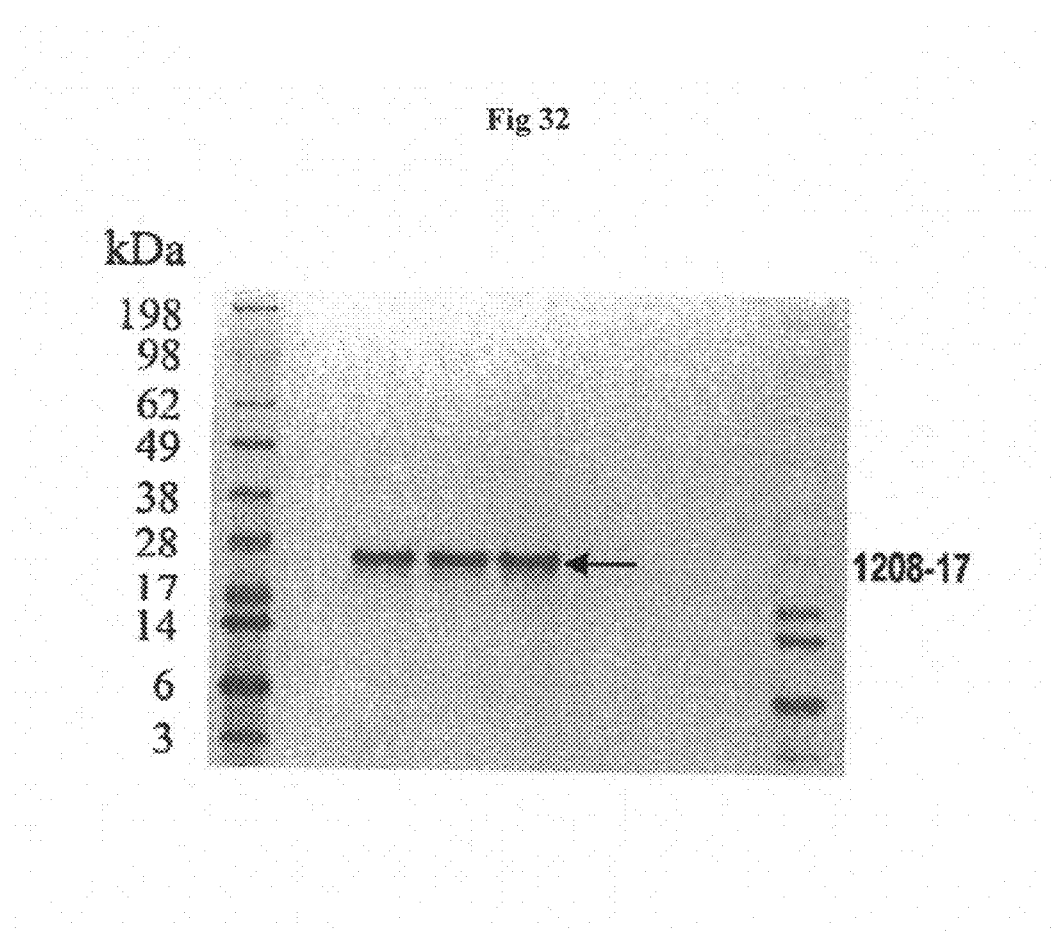

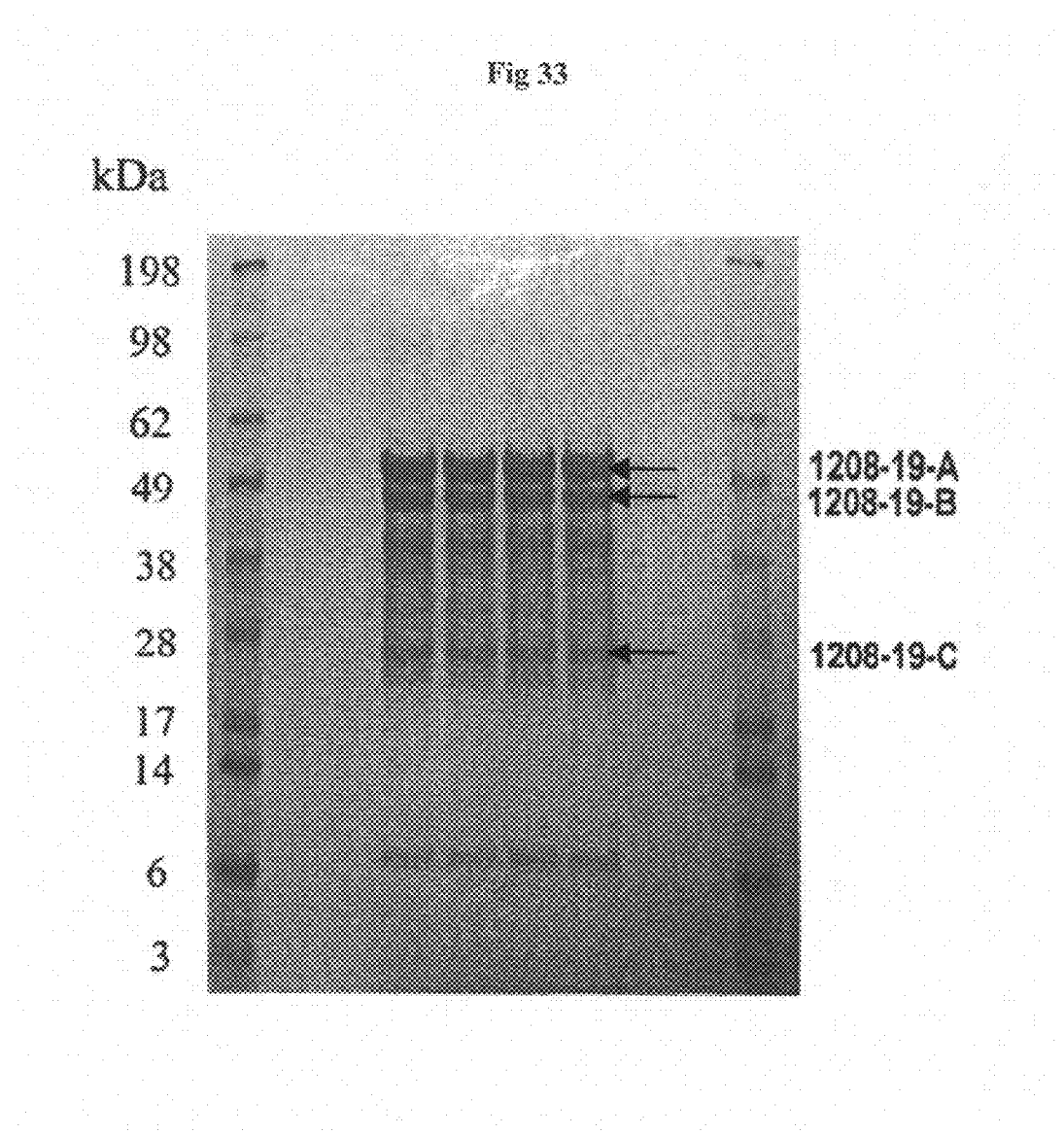

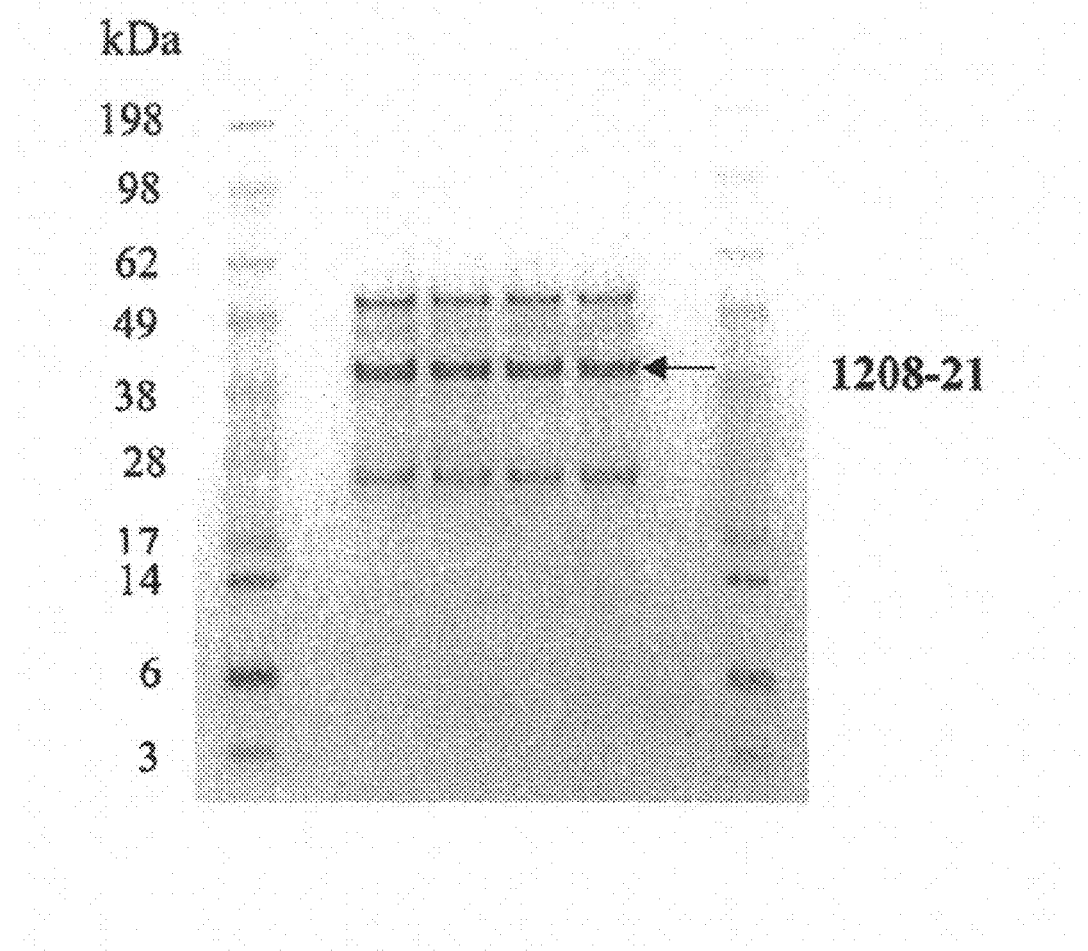

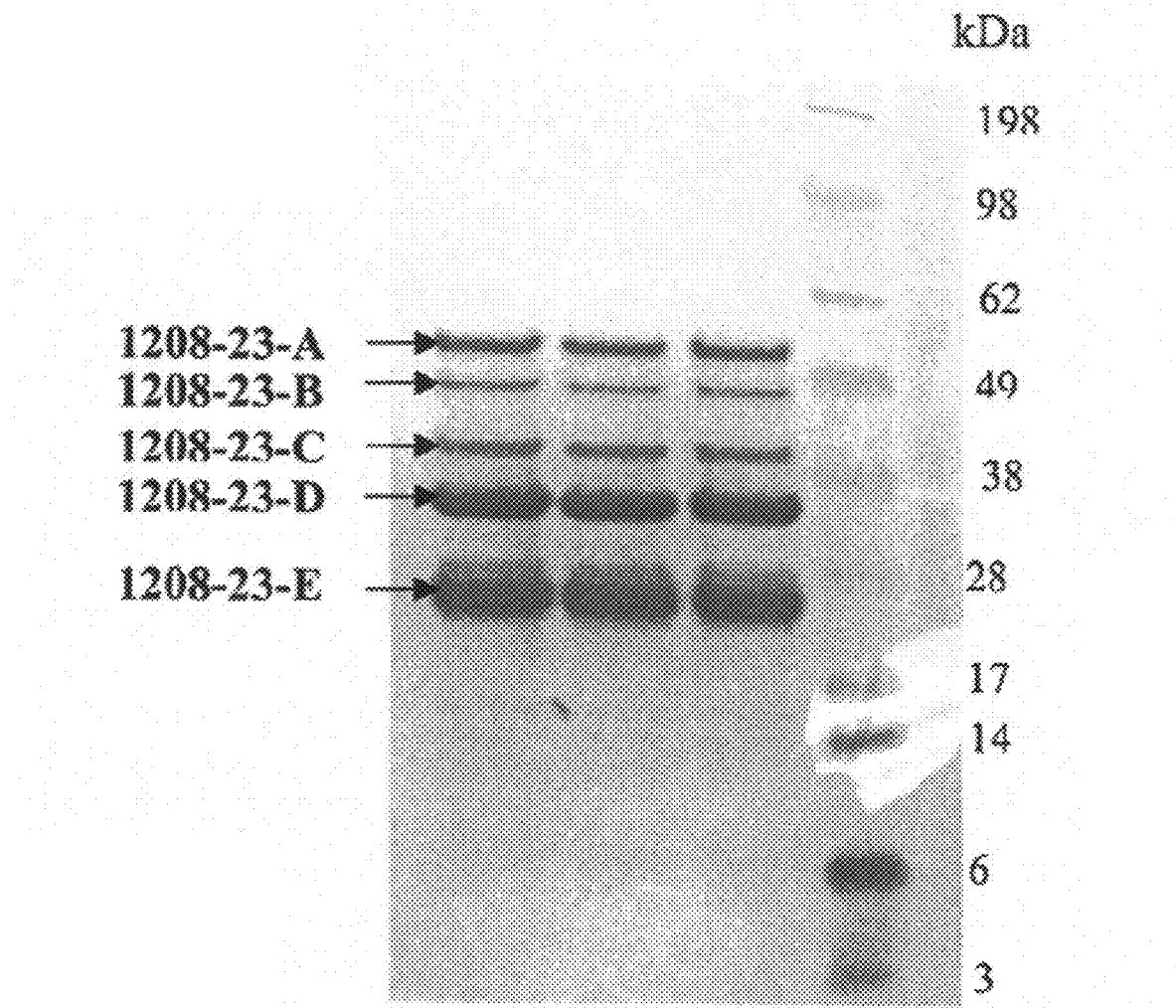

SEQUENCE LISTING

```
<160> NUMBER OF SEQ ID NOS: 34

<210> SEQ ID NO 1
<211> LENGTH: 124
<212> TYPE: PRT
<213> ORGANISM: Homo sapiens

<400> SEQUENCE: 1

Ala Leu Trp Gln Phe Arg Ser Met Ile Lys Cys Thr Ile Pro Gly Ser
1               5                   10                  15

Asp Pro Leu Leu Asp Phe Asn Asn Tyr Gly Cys Tyr Cys Gly Leu Gly
            20                  25                  30

Gly Ser Gly Thr Pro Val Asp Glu Leu Asp Arg Cys Cys Glu Thr His
        35                  40                  45

Asp Asn Cys Tyr Arg Asp Ala Lys Asn Leu Asp Ser Cys Lys Phe Leu
    50                  55                  60

Val Asp Asn Pro Tyr Thr Asn Ser Tyr Ser Tyr Ser Cys Ser Asn Thr
65                  70                  75                  80

Glu Ile Thr Cys Asn Ser Lys Asn Asn Ala Cys Glu Ala Phe Ile Cys
                85                  90                  95

Asn Cys Asp Arg Asn Ala Ala Ile Cys Phe Ser Lys Ala Pro Tyr Asn
            100                 105                 110

Lys Glu His Lys Asn Leu Asp Thr Lys Lys Tyr Cys
        115                 120
```

<210> SEQ ID NO 2
<211> LENGTH: 112
<212> TYPE: PRT
<213> ORGANISM: Homo sapiens

<400> SEQUENCE: 2

Met Glu Lys Val Leu Ala Leu Leu Val Thr Leu Thr Val Ala Tyr
1               5                   10                  15

Ala Val Pro Asp Pro Arg Gly Ile Ile Ile Asn Leu Asp Glu Gly Glu
            20                  25                  30

Leu Cys Leu Asn Ser Ala Gln Cys Lys Ser Asn Cys Cys Gln His Asp
        35                  40                  45

Thr Ile Leu Ser Leu Ser Arg Cys Ala Leu Lys Ala Arg Glu Asn Ser
    50                  55                  60

Glu Cys Ser Ala Phe Thr Leu Tyr Gly Val Tyr Tyr Lys Cys Pro Cys
65                  70                  75                  80

Glu Arg Gly Leu Thr Cys Glu Gly Asp Lys Ser Leu Val Gly Ser Ile
                85                  90                  95

Thr Asn Thr Asn Phe Gly Ile Cys His Asp Val Gly Arg Ser Ser Asp
            100                 105                 110

<210> SEQ ID NO 3
<211> LENGTH: 449
<212> TYPE: PRT
<213> ORGANISM: Homo sapiesn

<400> SEQUENCE: 3

Ser Glu Val Cys Phe Pro Arg Leu Gly Cys Phe Ser Asp Asp Ala Pro
1               5                   10                  15

Trp Ala Gly Ile Val Gln Arg Pro Leu Lys Ile Leu Pro Pro Asp Lys
            20                  25                  30

Asp Val Asp Thr Arg Phe Leu Leu Tyr Thr Asn Gln Asn Gln Asn Asn
        35                  40                  45

Tyr Gln Glu Leu Val Ala Asp Pro Ser Thr Ile Thr Asn Ser Asn Phe
    50                  55                  60

Arg Met Asp Arg Lys Thr Arg Phe Ile Ile His Gly Phe Ile Asp Lys
65                  70                  75                  80

Gly Glu Glu Asp Trp Leu Ser Asn Ile Cys Lys Asn Leu Phe Lys Val
                85                  90                  95

Glu Ser Val Asn Cys Ile Cys Val Asp Trp Lys Gly Gly Ser Arg Thr
            100                 105                 110

Gly Tyr Thr Gln Ala Ser Gln Asn Ile Arg Ile Val Gly Ala Glu Val
        115                 120                 125

Ala Tyr Phe Val Glu Val Leu Lys Ser Ser Leu Gly Tyr Ser Pro Ser
    130                 135                 140

Asn Val His Val Ile Gly His Ser Leu Gly Ser His Ala Ala Gly Glu
145                 150                 155                 160

Ala Gly Arg Arg Thr Asn Gly Thr Ile Glu Arg Ile Thr Gly Leu Asp
                165                 170                 175

Pro Ala Glu Pro Cys Phe Gln Gly Thr Pro Glu Leu Val Arg Leu Asp
            180                 185                 190

Pro Ser Asp Ala Lys Phe Val Asp Val Ile His Thr Asp Ala Ala Pro
        195                 200                 205

Ile Ile Pro Asn Leu Gly Phe Gly Met Ser Gln Thr Val Gly His Leu
    210                 215                 220

-continued

```
Asp Phe Phe Pro Asn Gly Gly Lys Gln Met Pro Gly Cys Gln Lys Asn
225                 230                 235                 240

Ile Leu Ser Gln Ile Val Asp Ile Asp Gly Ile Trp Glu Gly Thr Arg
            245                 250                 255

Asp Phe Val Ala Cys Asn His Leu Arg Ser Tyr Lys Tyr Tyr Ala Asp
        260                 265                 270

Ser Ile Leu Asn Pro Asp Gly Phe Ala Gly Phe Pro Cys Asp Ser Tyr
    275                 280                 285

Asn Val Phe Thr Ala Asn Lys Cys Phe Pro Cys Pro Ser Glu Gly Cys
290                 295                 300

Pro Gln Met Gly His Tyr Ala Asp Arg Phe Pro Gly Lys Thr Asn Gly
305                 310                 315                 320

Val Ser Gln Val Phe Tyr Leu Asn Thr Gly Asp Ala Ser Asn Phe Ala
            325                 330                 335

Arg Trp Arg Tyr Lys Val Ser Val Thr Leu Ser Gly Lys Lys Val Thr
        340                 345                 350

Gly His Ile Leu Val Ser Leu Phe Gly Asn Glu Gly Asn Ser Arg Gln
    355                 360                 365

Tyr Glu Ile Tyr Lys Gly Thr Leu Gln Pro Asp Asn Thr His Ser Asp
370                 375                 380

Glu Phe Asp Ser Asp Val Glu Val Gly Asp Leu Gln Lys Val Lys Phe
385                 390                 395                 400

Ile Trp Tyr Asn Asn Asn Val Ile Asn Pro Thr Leu Pro Arg Val Gly
            405                 410                 415

Ala Ser Lys Ile Thr Val Glu Arg Asn Asp Gly Lys Val Tyr Asp Phe
        420                 425                 430

Cys Ser Gln Glu Thr Val Arg Glu Val Leu Leu Thr Leu Asn Pro
    435                 440                 445

Cys

<210> SEQ ID NO 4
<211> LENGTH: 496
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 4

Xaa Tyr Ala Pro Gln Thr Gln Ser Gly Arg Thr Ser Ile Val His Leu
1               5                   10                  15

Phe Glu Trp Arg Trp Val Asp Ile Ala Leu Glu Cys Glu Arg Tyr Leu
            20                  25                  30

Gly Pro Lys Gly Phe Gly Gly Val Gln Val Ser Pro Pro Asn Glu Asn
        35                  40                  45

Ile Val Val Thr Asn Pro Ser Arg Pro Trp Trp Glu Arg Tyr Gln Pro
    50                  55                  60

Val Ser Tyr Lys Leu Cys Thr Arg Ser Gly Asn Glu Asn Glu Phe Arg
65                  70                  75                  80

Asp Met Val Thr Arg Cys Asn Asn Val Gly Val Arg Ile Tyr Val Asp
                85                  90                  95

Ala Val Ile Asn His Met Cys Gly Ser Gly Ala Ala Ala Gly Thr Gly
            100                 105                 110

Thr Thr Cys Gly Ser Tyr Cys Asn Pro Gly Asn Arg Glu Phe Pro Ala
```

```
                115                 120                 125
Val Pro Tyr Ser Ala Trp Asp Phe Asn Asp Gly Lys Cys Lys Thr Ala
130                 135                 140

Ser Gly Gly Ile Glu Ser Tyr Asn Asp Pro Tyr Gln Val Arg Asp Cys
145                 150                 155                 160

Gln Leu Val Gly Leu Leu Asp Leu Ala Leu Glu Lys Asp Tyr Val Arg
                165                 170                 175

Ser Met Ile Ala Asp Tyr Leu Asn Lys Leu Ile Asp Ile Gly Val Ala
                180                 185                 190

Gly Phe Arg Ile Asp Ala Ser Lys His Met Trp Pro Gly Asp Ile Lys
            195                 200                 205

Ala Val Leu Asp Lys Leu His Asn Leu Asn Thr Asn Trp Phe Pro Ala
210                 215                 220

Gly Ser Arg Pro Phe Ile Phe Gln Glu Val Ile Asp Leu Gly Gly Glu
225                 230                 235                 240

Ala Ile Lys Ser Ser Glu Tyr Phe Gly Asn Gly Arg Val Thr Glu Phe
                245                 250                 255

Lys Tyr Gly Ala Lys Leu Gly Thr Val Val Arg Lys Trp Ser Gly Glu
                260                 265                 270

Lys Met Ser Tyr Leu Lys Asn Trp Gly Glu Gly Trp Gly Phe Met Pro
                275                 280                 285

Ser Asp Arg Ala Leu Val Phe Val Asp Asn His Asp Asn Gln Arg Gly
290                 295                 300

His Gly Ala Gly Gly Ser Ser Ile Leu Thr Phe Trp Asp Ala Arg Leu
305                 310                 315                 320

Tyr Lys Ile Ala Val Gly Phe Met Leu Ala His Pro Tyr Gly Phe Thr
                325                 330                 335

Arg Val Met Ser Ser Tyr Arg Trp Ala Arg Asn Phe Val Asn Gly Glu
                340                 345                 350

Asp Val Asn Asp Trp Ile Gly Pro Pro Asn Asn Gly Val Ile Lys
            355                 360                 365

Glu Val Thr Ile Asn Ala Asp Thr Thr Cys Gly Asn Asp Trp Val Cys
370                 375                 380

Glu His Arg Trp Arg Glu Ile Arg Asn Met Val Trp Phe Arg Asn Val
385                 390                 395                 400

Val Asp Gly Gln Pro Phe Ala Asn Trp Trp Asp Asn Gly Ser Asn Gln
                405                 410                 415

Val Ala Phe Gly Arg Gly Asn Arg Gly Phe Ile Val Phe Asn Asn Asp
                420                 425                 430

Asp Trp Gln Leu Ser Ser Thr Leu Gln Thr Gly Leu Pro Gly Gly Thr
            435                 440                 445

Tyr Cys Asp Val Ile Ser Gly Asp Lys Val Gly Asn Ser Cys Thr Gly
        450                 455                 460

Ile Lys Val Tyr Val Ser Ser Asp Gly Thr Ala Gln Phe Ser Ile Ser
465                 470                 475                 480

Asn Ser Ala Glu Asp Pro Phe Ile Ala Ile His Ala Glu Ser Lys Leu
                485                 490                 495

<210> SEQ ID NO 5
<211> LENGTH: 223
<212> TYPE: PRT
<213> ORGANISM: Homo sapiens
<220> FEATURE:
<221> NAME/KEY: misc_feature
<222> LOCATION: (97)..(97)
```

<223> OTHER INFORMATION: Xaa can be any naturally occurring amino acid

<400> SEQUENCE: 5

```
Ile Val Gly Gly Tyr Thr Cys Ala Ala Asn Ser Ile Pro Tyr Gln Val
1               5                   10                  15
Ser Leu Asn Ser Gly Ser His Phe Cys Gly Gly Ser Leu Ile Asn Ser
            20                  25                  30
Gln Trp Val Val Ser Ala Ala His Cys Tyr Lys Ser Arg Ile Gln Val
        35                  40                  45
Arg Leu Gly Glu His Asn Ile Asp Val Leu Glu Gly Asn Glu Gln Phe
    50                  55                  60
Ile Asn Ala Ala Lys Ile Ile Thr His Pro Asn Phe Asn Gly Asn Thr
65                  70                  75                  80
Leu Asp Asn Asp Ile Met Leu Ile Lys Leu Ser Ser Pro Ala Thr Leu
                85                  90                  95
Xaa Ser Arg Val Ala Thr Val Ser Leu Pro Arg Ser Cys Ala Ala Ala
            100                 105                 110
Gly Thr Glu Cys Leu Ile Ser Gly Trp Gly Asn Thr Lys Ser Ser Gly
        115                 120                 125
Ser Ser Tyr Pro Ser Leu Leu Gln Cys Leu Lys Ala Pro Val Leu Ser
    130                 135                 140
Asp Ser Ser Cys Lys Ser Ser Tyr Pro Gly Gln Ile Thr Gly Asn Met
145                 150                 155                 160
Ile Cys Val Gly Phe Leu Glu Gly Gly Lys Asp Ser Cys Gln Gly Asp
                165                 170                 175
Ser Gly Gly Pro Val Val Cys Asn Gly Gln Leu Gln Gly Ile Val Ser
            180                 185                 190
Trp Gly Tyr Gly Cys Ala Gln Lys Asn Lys Pro Gly Val Tyr Thr Lys
        195                 200                 205
Val Cys Asn Tyr Val Asn Trp Ile Gln Gln Thr Ile Ala Ala Asn
    210                 215                 220
```

<210> SEQ ID NO 6
<211> LENGTH: 496
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 6

```
Xaa Tyr Ala Pro Gln Thr Gln Ser Gly Arg Thr Ser Ile Val His Leu
1               5                   10                  15
Phe Glu Trp Arg Trp Val Asp Ile Ala Leu Glu Cys Glu Arg Tyr Leu
            20                  25                  30
Gly Pro Lys Gly Phe Gly Gly Val Gln Val Ser Pro Pro Asn Glu Asn
        35                  40                  45
Ile Val Val Thr Asn Pro Ser Arg Pro Trp Trp Glu Arg Tyr Gln Pro
    50                  55                  60
Val Ser Tyr Lys Leu Cys Thr Arg Ser Gly Asn Glu Asn Glu Phe Arg
65                  70                  75                  80
Asp Met Val Thr Arg Cys Asn Asn Val Gly Val Arg Ile Tyr Val Asp
                85                  90                  95
Ala Val Ile Asn His Met Cys Gly Ser Gly Ala Ala Ala Gly Thr Gly
            100                 105                 110
```

Thr Thr Cys Gly Ser Tyr Cys Asn Pro Gly Ser Arg Glu Phe Pro Ala
            115                 120                 125

Val Pro Tyr Ser Ala Trp Asp Phe Asn Asp Gly Lys Cys Lys Thr Ala
130                 135                 140

Ser Gly Gly Ile Glu Ser Tyr Asn Asp Pro Tyr Gln Val Arg Asp Cys
145                 150                 155                 160

Gln Leu Val Gly Leu Leu Asp Leu Ala Leu Glu Lys Asp Tyr Val Arg
            165                 170                 175

Ser Met Ile Ala Asp Tyr Leu Asn Lys Leu Ile Asp Ile Gly Val Ala
            180                 185                 190

Gly Phe Arg Ile Asp Ala Ser Lys His Met Trp Pro Gly Asp Ile Lys
            195                 200                 205

Ala Val Leu Asp Lys Leu His Asn Leu Asn Thr Asn Trp Phe Pro Ala
210                 215                 220

Gly Ser Arg Pro Phe Ile Phe Gln Glu Val Ile Asp Leu Gly Gly Glu
225                 230                 235                 240

Ala Ile Gln Ser Ser Glu Tyr Phe Gly Asn Gly Arg Val Thr Glu Phe
            245                 250                 255

Lys Tyr Gly Ala Lys Leu Gly Thr Val Val Arg Lys Trp Ser Gly Glu
            260                 265                 270

Lys Met Ser Tyr Leu Lys Asn Trp Gly Glu Gly Trp Gly Phe Met Pro
            275                 280                 285

Ser Asp Arg Ala Leu Val Phe Val Asp Asn His Asp Asn Gln Arg Gly
            290                 295                 300

His Gly Ala Gly Gly Ala Ser Ile Leu Thr Phe Trp Asp Ala Arg Leu
305                 310                 315                 320

Tyr Lys Val Ala Val Gly Phe Met Leu Ala His Pro Tyr Gly Phe Thr
            325                 330                 335

Arg Val Met Ser Ser Tyr Arg Trp Ala Arg Asn Phe Val Asn Gly Glu
            340                 345                 350

Asp Val Asn Asp Trp Ile Gly Pro Pro Asn Asn Asn Gly Val Ile Lys
            355                 360                 365

Glu Val Thr Ile Asn Ala Asp Thr Thr Cys Gly Asn Asp Trp Val Cys
370                 375                 380

Glu His Arg Trp Arg Glu Ile Arg Asn Met Val Trp Phe Arg Asn Val
385                 390                 395                 400

Val Asp Gly Glu Pro Phe Ala Asn Trp Trp Asp Asn Gly Ser Asn Gln
            405                 410                 415

Val Ala Phe Gly Arg Gly Asn Arg Gly Phe Ile Val Phe Asn Asn Asp
            420                 425                 430

Asp Trp Gln Leu Ser Ser Thr Leu Gln Thr Gly Leu Pro Gly Gly Thr
            435                 440                 445

Tyr Cys Asp Val Ile Ser Gly Asp Lys Val Gly Asn Ser Cys Thr Gly
450                 455                 460

Ile Lys Val Tyr Val Ser Ser Asp Gly Thr Ala Gln Phe Ser Ile Ser
465                 470                 475                 480

Asn Ser Ala Glu Asp Pro Phe Ile Ala Ile His Ala Glu Ser Lys Leu
            485                 490                 495

<210> SEQ ID NO 7
<211> LENGTH: 231
<212> TYPE: PRT
<213> ORGANISM: Homo sapiens

<400> SEQUENCE: 7

```
Phe Pro Thr Asp Asp Asp Lys Ile Val Gly Gly Tyr Thr Cys Ala
1               5                   10                  15

Ala Asn Ser Ile Pro Tyr Gln Val Ser Leu Asn Ser Gly Ser His Phe
            20                  25                  30

Cys Gly Gly Ser Leu Ile Asn Ser Gln Trp Val Val Ser Ala Ala His
        35                  40                  45

Cys Tyr Lys Ser Arg Ile Gln Val Arg Leu Gly Glu His Asn Ile Asp
    50                  55                  60

Val Leu Glu Gly Asn Glu Gln Phe Ile Asn Ala Ala Lys Ile Ile Thr
65                  70                  75                  80

His Pro Asn Phe Asn Gly Asn Thr Leu Asp Asn Asp Ile Met Leu Ile
            85                  90                  95

Lys Leu Ser Ser Pro Ala Thr Leu Asn Ser Arg Val Ala Thr Val Ser
            100                 105                 110

Leu Pro Arg Ser Cys Ala Ala Ala Gly Thr Glu Cys Leu Ile Ser Gly
            115                 120                 125

Trp Gly Asn Thr Lys Ser Ser Gly Ser Ser Tyr Pro Ser Leu Leu Gln
130                 135                 140

Cys Leu Lys Ala Pro Val Leu Ser Asp Ser Ser Cys Lys Ser Ser Tyr
145                 150                 155                 160

Pro Gly Gln Ile Thr Gly Asn Met Ile Cys Val Gly Phe Leu Glu Gly
            165                 170                 175

Gly Lys Asp Ser Cys Gln Gly Asp Ser Gly Gly Pro Val Val Cys Asn
            180                 185                 190

Gly Gln Leu Gln Gly Ile Val Ser Trp Gly Tyr Gly Cys Ala Gln Lys
            195                 200                 205

Asn Lys Pro Gly Val Tyr Thr Lys Val Cys Asn Tyr Val Asn Trp Ile
            210                 215                 220

Gln Gln Thr Ile Ala Ala Asn
225                 230

<210> SEQ ID NO 8
<211> LENGTH: 250
<212> TYPE: PRT
<213> ORGANISM: Homo sapiens

<400> SEQUENCE: 8

Met Ile Arg Ala Leu Leu Leu Ser Thr Leu Val Ala Gly Ala Leu Ser
1               5                   10                  15

Cys Gly Leu Pro Ala Asn Leu Pro Gln Leu Pro Arg Val Val Gly Gly
            20                  25                  30

Glu Asp Ala Arg Pro Asn Ser Trp Pro Trp Gln Val Ser Leu Gln Tyr
            35                  40                  45

Asp Ser Ser Gly Gln Trp Arg His Thr Cys Gly Gly Thr Leu Val Asp
    50                  55                  60

Gln Ser Trp Val Leu Thr Ala Ala His Cys Ile Ser Ser Ser Arg Thr
65                  70                  75                  80

Tyr Arg Val Val Leu Gly Arg His Ser Leu Ser Thr Asn Glu Pro Gly
            85                  90                  95

Ser Leu Ala Val Lys Val Ser Lys Leu Val Val His Gln Asp Trp Asn
            100                 105                 110

Ser Asn Gln Leu Ser Asn Gly Asn Asp Ile Ala Leu Leu Lys Leu Ala
            115                 120                 125

Ser Pro Val Ser Leu Thr Asp Lys Ile Gln Leu Gly Cys Leu Pro Ala
```

```
                130                 135                 140
Ala Gly Thr Ile Leu Pro Asn Asn Tyr Val Cys Tyr Val Thr Gly Trp
145                 150                 155                 160

Gly Arg Leu Gln Thr Asn Gly Ala Ser Pro Asp Ile Leu Gln Gln Gly
                165                 170                 175

Gln Leu Leu Val Val Asp Tyr Ala Thr Cys Ser Lys Pro Gly Trp Trp
                180                 185                 190

Gly Ser Thr Val Lys Thr Asn Met Ile Cys Ala Gly Gly Asp Gly Ile
                195                 200                 205

Ile Ser Ser Cys Asn Gly Asp Ser Gly Gly Pro Leu Asn Cys Gln Gly
                210                 215                 220

Ala Asn Gly Gln Trp Gln Val His Gly Ile Val Ser Phe Gly Ser Ser
225                 230                 235                 240

Leu Gly Cys Asn Tyr Tyr His Lys Pro Ser
                245                 250

<210> SEQ ID NO 9
<211> LENGTH: 449
<212> TYPE: PRT
<213> ORGANISM: Homo sapiens

<400> SEQUENCE: 9

Ser Glu Val Cys Phe Pro Arg Leu Gly Cys Phe Ser Asp Asp Ala Pro
1               5                   10                  15

Trp Ala Gly Ile Val Gln Arg Pro Leu Lys Ile Leu Pro Pro Asp Lys
                20                  25                  30

Asp Val Asp Thr Arg Phe Leu Leu Tyr Thr Asn Gln Asn Gln Asn Asn
                35                  40                  45

Tyr Gln Glu Leu Val Ala Asp Pro Ser Thr Ile Thr Asn Ser Asn Phe
50                  55                  60

Arg Met Asp Arg Lys Thr Arg Phe Ile Ile His Gly Phe Ile Asp Lys
65                  70                  75                  80

Gly Glu Glu Asp Trp Leu Ser Asn Ile Cys Lys Asn Leu Phe Lys Val
                85                  90                  95

Glu Ser Val Asn Cys Ile Cys Val Asp Trp Lys Gly Gly Ser Arg Thr
                100                 105                 110

Gly Tyr Thr Gln Ala Ser Gln Asn Ile Arg Ile Val Gly Ala Glu Val
                115                 120                 125

Ala Tyr Phe Val Glu Val Leu Lys Ser Ser Leu Gly Tyr Ser Pro Ser
                130                 135                 140

Asn Val His Val Ile Gly His Ser Leu Gly Ser His Ala Ala Gly Glu
145                 150                 155                 160

Ala Gly Arg Arg Thr Asn Gly Thr Ile Glu Arg Ile Thr Gly Leu Asp
                165                 170                 175

Pro Ala Glu Pro Cys Phe Gln Gly Thr Pro Glu Leu Val Arg Leu Asp
                180                 185                 190

Pro Ser Asp Ala Lys Phe Val Asp Val Ile His Thr Asp Ala Ala Pro
                195                 200                 205

Ile Ile Pro Asn Leu Gly Phe Gly Met Ser Gln Thr Val Gly His Leu
                210                 215                 220

Asp Phe Phe Pro Asn Gly Gly Lys Gln Met Pro Gly Cys Gln Lys Asn
225                 230                 235                 240

Ile Leu Ser Gln Ile Val Asp Ile Asp Gly Ile Trp Glu Gly Thr Arg
                245                 250                 255
```

-continued

```
Asp Phe Val Ala Cys Asn His Leu Arg Ser Tyr Lys Tyr Ala Asp
            260                 265                 270

Ser Ile Leu Asn Pro Asp Gly Phe Ala Gly Phe Pro Cys Asp Ser Tyr
275                 280                 285

Asn Val Phe Thr Ala Asn Lys Cys Phe Pro Cys Pro Ser Glu Gly Cys
            290                 295                 300

Pro Gln Met Gly His Tyr Ala Asp Arg Phe Pro Gly Lys Thr Asn Gly
305                 310                 315                 320

Val Ser Gln Val Phe Tyr Leu Asn Thr Gly Asp Ala Ser Asn Phe Ala
                325                 330                 335

Arg Trp Arg Tyr Lys Val Ser Val Thr Leu Ser Gly Lys Lys Val Thr
            340                 345                 350

Gly His Ile Leu Val Ser Leu Phe Gly Asn Glu Gly Asn Ser Arg Gln
        355                 360                 365

Tyr Glu Ile Tyr Lys Gly Thr Leu Gln Pro Asp Asn Thr His Ser Asp
    370                 375                 380

Glu Phe Asp Ser Asp Val Glu Val Gly Asp Leu Gln Lys Val Lys Phe
385                 390                 395                 400

Ile Trp Tyr Asn Asn Asn Val Ile Asn Pro Thr Leu Pro Arg Val Gly
                405                 410                 415

Ala Ser Lys Ile Thr Val Glu Arg Asn Asp Gly Lys Val Tyr Asp Phe
            420                 425                 430

Cys Ser Gln Glu Thr Val Arg Glu Val Leu Leu Thr Leu Asn Pro
        435                 440                 445

Cys

<210> SEQ ID NO 10
<211> LENGTH: 264
<212> TYPE: PRT
<213> ORGANISM: Homo sapien

<400> SEQUENCE: 10

Met Leu Leu Leu Ser Leu Thr Leu Ser Leu Val Leu Gly Ser Ser
1               5                   10                  15

Trp Gly Cys Gly Ile Pro Ala Ile Lys Pro Val Leu Ser Phe Ser Gln
                20                  25                  30

Arg Ile Val Asn Gly Glu Asn Ala Val Pro Gly Ser Trp Pro Trp Gln
            35                  40                  45

Val Ser Leu Gln Asp Lys Ser Gly Phe His Phe Cys Gly Gly Ser Leu
        50                  55                  60

Ile Ser Gln Ser Trp Val Val Thr Ala Ala His Cys Asn Val Ile Pro
65                  70                  75                  80

Gly Arg His Val Val Val Leu Gly Glu Tyr Asp Arg Ser Ser Asn Ala
                85                  90                  95

Glu Pro Leu Gln Val Leu Ser Ile Ser Lys Ala Ile Thr Tyr Pro Ser
            100                 105                 110

Trp Asn Pro Thr Thr Leu Asn Asn Asp Leu Thr Leu Leu Lys Leu Ala
        115                 120                 125

Ser Pro Ala Arg Tyr Thr Gln Arg Ile Ser Pro Val Cys Leu Ala Ser
    130                 135                 140

Pro Asp Glu Glu Leu Pro Ala Gly Leu Lys Cys Ala Thr Thr Gly Trp
145                 150                 155                 160

Gly Arg Leu Ser Gly Val Gly Asn Val Thr Pro Ala Arg Leu Gln Gln
                165                 170                 175
```

```
Val Ala Leu Pro Leu Val Thr Val Asn Glu Cys Arg Gln Tyr Trp Gly
            180                 185                 190

Ser Arg Ile Thr Asp Ala Met Ile Cys Ala Gly Gly Ser Gly Ala Ser
            195                 200                 205

Ser Cys Gln Gly Asp Ser Gly Gly Pro Leu Val Cys Gln Lys Gly Asn
            210                 215                 220

Thr Trp Val Leu Ile Gly Ile Val Ser Trp Gly Thr Thr Asn Cys Asn
225                 230                 235                 240

Val Arg Gln Pro Ala Ile Tyr Thr Arg Val Ser Lys Phe Ser Thr Trp
            245                 250                 255

Ile Ser Gln Val Ile Ala Tyr Asn
            260

<210> SEQ ID NO 11
<211> LENGTH: 449
<212> TYPE: PRT
<213> ORGANISM: Homo sapiens

<400> SEQUENCE: 11

Ser Glu Val Cys Phe Pro Arg Leu Gly Cys Phe Ser Asp Asp Ala Pro
1               5                   10                  15

Trp Ala Gly Ile Val Gln Arg Pro Leu Lys Ile Leu Pro Pro Asp Lys
            20                  25                  30

Asp Val Asp Thr Arg Phe Leu Leu Tyr Thr Asn Gln Asn Gln Asn Asn
        35                  40                  45

Tyr Gln Glu Leu Val Ala Asp Pro Ser Thr Ile Thr Asn Ser Asn Phe
    50                  55                  60

Arg Met Asp Arg Lys Thr Arg Phe Ile Ile His Gly Phe Ile Asp Lys
65                  70                  75                  80

Gly Glu Glu Asp Trp Leu Ser Asn Ile Cys Lys Asn Leu Phe Lys Val
                85                  90                  95

Glu Ser Val Asn Cys Ile Cys Val Asp Trp Lys Gly Gly Ser Arg Thr
            100                 105                 110

Gly Tyr Thr Gln Ala Ser Gln Asn Ile Arg Ile Val Gly Ala Glu Val
        115                 120                 125

Ala Tyr Phe Val Glu Val Leu Lys Ser Ser Leu Gly Tyr Ser Pro Ser
    130                 135                 140

Asn Val His Val Ile Gly His Ser Leu Gly Ser His Ala Ala Gly Glu
145                 150                 155                 160

Ala Gly Arg Arg Thr Asn Gly Thr Ile Glu Arg Ile Thr Gly Leu Asp
                165                 170                 175

Pro Ala Glu Pro Cys Phe Gln Gly Thr Pro Glu Leu Val Arg Leu Asp
            180                 185                 190

Pro Ser Asp Ala Lys Phe Val Asp Val Ile His Thr Asp Ala Ala Pro
        195                 200                 205

Ile Ile Pro Asn Leu Gly Phe Gly Met Ser Gln Thr Val Gly His Leu
    210                 215                 220

Asp Phe Phe Pro Asn Gly Gly Lys Gln Met Pro Gly Cys Gln Lys Asn
225                 230                 235                 240

Ile Leu Ser Gln Ile Val Asp Ile Asp Gly Ile Trp Glu Gly Thr Arg
                245                 250                 255

Asp Phe Val Ala Cys Asn His Leu Arg Ser Tyr Lys Tyr Tyr Ala Asp
            260                 265                 270

Ser Ile Leu Asn Pro Asp Gly Phe Ala Gly Phe Pro Cys Asp Ser Tyr
        275                 280                 285
```

-continued

Asn Val Phe Thr Ala Asn Lys Cys Phe Pro Cys Pro Ser Glu Gly Cys
     290                 295                 300

Pro Gln Met Gly His Tyr Ala Asp Arg Phe Pro Gly Lys Thr Asn Gly
305                 310                 315                 320

Val Ser Gln Val Phe Tyr Leu Asn Thr Gly Asp Ala Ser Asn Phe Ala
                325                 330                 335

Arg Trp Arg Tyr Lys Val Ser Val Thr Leu Ser Gly Lys Lys Val Thr
                340                 345                 350

Gly His Ile Leu Val Ser Leu Phe Gly Asn Glu Gly Asn Ser Arg Gln
                355                 360                 365

Tyr Glu Ile Tyr Lys Gly Thr Leu Gln Pro Asp Asn Thr His Ser Asp
370                 375                 380

Glu Phe Asp Ser Asp Val Glu Val Gly Asp Leu Gln Lys Val Lys Phe
385                 390                 395                 400

Ile Trp Tyr Asn Asn Asn Val Ile Asn Pro Thr Leu Pro Arg Val Gly
                405                 410                 415

Ala Ser Lys Ile Thr Val Glu Arg Asn Asp Gly Lys Val Tyr Asp Phe
                420                 425                 430

Cys Ser Gln Glu Thr Val Arg Glu Glu Val Leu Leu Thr Leu Asn Pro
                435                 440                 445

Cys

<210> SEQ ID NO 12
<211> LENGTH: 449
<212> TYPE: PRT
<213> ORGANISM: Homo sapiens

<400> SEQUENCE: 12

Ser Glu Val Cys Phe Pro Arg Leu Gly Cys Phe Ser Asp Asp Ala Pro
1               5                   10                  15

Trp Ala Gly Ile Val Gln Arg Pro Leu Lys Ile Leu Pro Pro Asp Lys
                20                  25                  30

Asp Val Asp Thr Arg Phe Leu Leu Tyr Thr Asn Gln Asn Gln Asn Asn
            35                  40                  45

Tyr Gln Glu Leu Val Ala Asp Pro Ser Thr Ile Thr Asn Ser Asn Phe
50                  55                  60

Arg Met Asp Arg Lys Thr Arg Phe Ile Ile His Gly Phe Ile Asp Lys
65                  70                  75                  80

Gly Glu Glu Asp Trp Leu Ser Asn Ile Cys Lys Asn Leu Phe Lys Val
                85                  90                  95

Glu Ser Val Asn Cys Ile Cys Val Asp Trp Lys Gly Gly Ser Arg Thr
                100                 105                 110

Gly Tyr Thr Gln Ala Ser Gln Asn Ile Arg Ile Val Gly Ala Glu Val
            115                 120                 125

Ala Tyr Phe Val Glu Val Leu Lys Ser Ser Leu Gly Tyr Ser Pro Ser
130                 135                 140

Asn Val His Val Ile Gly His Ser Leu Gly Ser His Ala Ala Gly Glu
145                 150                 155                 160

Ala Gly Arg Arg Thr Asn Gly Thr Ile Glu Arg Ile Thr Gly Leu Asp
                165                 170                 175

Pro Ala Glu Pro Cys Phe Gln Gly Thr Pro Glu Leu Val Arg Leu Asp
            180                 185                 190

Pro Ser Asp Ala Lys Phe Val Asp Val Ile His Thr Asp Ala Ala Pro
        195                 200                 205

```
Ile Ile Pro Asn Leu Gly Phe Gly Met Ser Gln Thr Val Gly His Leu
210                 215                 220

Asp Phe Phe Pro Asn Gly Gly Lys Gln Met Pro Gly Cys Gln Lys Asn
225                 230                 235                 240

Ile Leu Ser Gln Ile Val Asp Ile Asp Gly Ile Trp Glu Gly Thr Arg
                245                 250                 255

Asp Phe Val Ala Cys Asn His Leu Arg Ser Tyr Lys Tyr Tyr Ala Asp
                260                 265                 270

Ser Ile Leu Asn Pro Asp Gly Phe Ala Gly Phe Pro Cys Asp Ser Tyr
            275                 280                 285

Asn Val Phe Thr Ala Asn Lys Cys Phe Pro Cys Pro Ser Glu Gly Cys
            290                 295                 300

Pro Gln Met Gly His Tyr Ala Asp Arg Phe Pro Gly Lys Thr Asn Gly
305                 310                 315                 320

Val Ser Gln Val Phe Tyr Leu Asn Thr Gly Asp Ala Ser Asn Phe Ala
                325                 330                 335

Arg Trp Arg Tyr Lys Val Ser Val Thr Leu Ser Gly Lys Lys Val Thr
                340                 345                 350

Gly His Ile Leu Val Ser Leu Phe Gly Asn Glu Gly Asn Ser Arg Gln
            355                 360                 365

Tyr Glu Ile Tyr Lys Gly Thr Leu Gln Pro Asp Asn Thr His Ser Asp
370                 375                 380

Glu Phe Asp Ser Asp Val Glu Val Gly Asp Leu Gln Lys Val Lys Phe
385                 390                 395                 400

Ile Trp Tyr Asn Asn Asn Val Ile Asn Pro Thr Leu Pro Arg Val Gly
                405                 410                 415

Ala Ser Lys Ile Thr Val Glu Arg Asn Asp Gly Lys Val Tyr Asp Phe
                420                 425                 430

Cys Ser Gln Glu Thr Val Arg Glu Glu Val Leu Leu Thr Leu Asn Pro
            435                 440                 445

Cys

<210> SEQ ID NO 13
<211> LENGTH: 122
<212> TYPE: PRT
<213> ORGANISM: Homo sapiens
<220> FEATURE:
<221> NAME/KEY: misc_feature
<222> LOCATION: (11)..(11)
<223> OTHER INFORMATION: Xaa can be any naturally occurring amino acid

<400> SEQUENCE: 13

Met Leu Pro Ser Met Ser Leu Pro Ser Leu Xaa Trp Met Leu Leu Ser
1               5                   10                  15

Cys Leu Met Leu Leu Ser Gln Val Gln Gly Glu Asp Ser Pro Ala Asp
                20                  25                  30

Thr Pro Ser Ala Arg Ile Ser Cys Pro Lys Gly Ser Met Ala Tyr Ala
                35                  40                  45

Ser Tyr Cys Tyr Ala Leu Phe Ile Thr Pro Lys Thr Trp Met Gly Ala
            50                  55                  60

Asp Met Ala Cys Gln Lys Arg Pro Ser Gly His Leu Val Ser Val Leu
65                  70                  75                  80

Ser Gly Ala Glu Ala Ser Phe Val Ser Ser Leu Ile Lys Asn Asn Leu
                85                  90                  95

Asn Ala Leu Ser Asp Val Trp Ile Gly Leu His Asp Pro Thr Glu Gly
```

```
                    100                 105                 110
Leu Glu Pro Asn Ala Gly Gly Trp Glu Trp
        115                 120

<210> SEQ ID NO 14
<211> LENGTH: 240
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 14

Xaa Val Gly Gly Thr Glu Ala Gln Arg Asn Ser Trp Pro Ser Gln Ile
1               5                   10                  15

Ser Leu Gln Tyr Arg Ser Gly Ser Ser Trp Ala His Thr Cys Gly Gly
            20                  25                  30

Thr Leu Ile Arg Gln Asn Trp Val Met Thr Ala Ala His Cys Val Asp
        35                  40                  45

Arg Glu Leu Thr Phe Arg Val Val Gly Glu His Asn Leu Asn Gln
    50                  55                  60

Asn Asp Gly Thr Glu Gln Tyr Val Gly Val Gln Lys Ile Val Val His
65                  70                  75                  80

Pro Tyr Trp Asn Thr Asp Asp Val Ala Ala Gly Tyr Asp Ile Ala Leu
                85                  90                  95

Leu Arg Leu Ala Gln Ser Val Thr Leu Asn Ser Tyr Val Gln Leu Gly
            100                 105                 110

Val Leu Pro Arg Ala Gly Thr Ile Leu Ala Asn Asn Ser Pro Cys Tyr
        115                 120                 125

Ile Thr Gly Trp Gly Leu Thr Arg Thr Asn Gly Gln Leu Ala Gln Thr
    130                 135                 140

Leu Gln Gln Ala Tyr Leu Pro Thr Val Asp Tyr Ala Ile Cys Ser Ser
145                 150                 155                 160

Ser Ser Tyr Trp Gly Ser Thr Val Lys Asn Ser Met Val Cys Ala Gly
                165                 170                 175

Gly Asp Gly Val Arg Ser Gly Cys Gln Gly Asp Ser Gly Gly Pro Leu
            180                 185                 190

His Cys Leu Val Asn Gly Gln Tyr Ala Val His Gly Val Thr Ser Phe
        195                 200                 205

Val Ser Arg Leu Gly Cys Asn Val Thr Arg Lys Pro Thr Val Phe Thr
    210                 215                 220

Arg Val Ser Ala Tyr Ile Ser Trp Ile Asn Asn Val Ile Ala Ser Asn
225                 230                 235                 240

<210> SEQ ID NO 15
<211> LENGTH: 240
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 15

Xaa Val Gly Gly Thr Glu Ala Gln Arg Asn Ser Trp Pro Ser Gln Ile
1               5                   10                  15

Ser Leu Gln Tyr Arg Ser Gly Ser Ser Trp Ala His Thr Cys Gly Gly
            20                  25                  30
```

```
Thr Leu Ile Arg Gln Asn Trp Val Met Thr Ala Ala His Cys Val Asp
        35                  40                  45

Arg Glu Leu Thr Phe Arg Val Val Gly Glu His Asn Leu Asn Gln
 50                  55                  60

Asn Asp Gly Thr Glu Gln Tyr Val Gly Val Lys Ile Val Val His
 65                  70                  75                  80

Pro Tyr Trp Asn Thr Asp Val Ala Ala Gly Tyr Asp Ile Ala Leu
                 85                  90                  95

Leu Arg Leu Ala Gln Ser Val Thr Leu Asn Ser Tyr Val Gln Leu Gly
                100                 105                 110

Val Leu Pro Arg Ala Gly Thr Ile Leu Ala Asn Asn Ser Pro Cys Tyr
                115                 120                 125

Ile Thr Gly Trp Gly Leu Thr Arg Thr Asn Gly Gln Leu Ala Gln Thr
                130                 135                 140

Leu Gln Gln Ala Tyr Leu Pro Thr Val Asp Tyr Ala Ile Cys Ser Ser
145                 150                 155                 160

Ser Ser Tyr Trp Gly Ser Thr Val Lys Asn Ser Met Val Cys Ala Gly
                165                 170                 175

Gly Asp Gly Val Arg Ser Gly Cys Gln Gly Asp Ser Gly Gly Pro Leu
                180                 185                 190

His Cys Leu Val Asn Gly Gln Tyr Ala Val His Gly Val Thr Ser Phe
                195                 200                 205

Val Ser Arg Leu Gly Cys Asn Val Thr Arg Lys Pro Thr Val Phe Thr
                210                 215                 220

Arg Val Ser Ala Tyr Ile Ser Trp Ile Asn Asn Val Ile Ala Ser Asn
225                 230                 235                 240

<210> SEQ ID NO 16
<211> LENGTH: 8
<212> TYPE: PRT
<213> ORGANISM: Homo sapiens

<400> SEQUENCE: 16

Gln Gly Asn Ser Leu Leu Leu Arg
1               5

<210> SEQ ID NO 17
<211> LENGTH: 8
<212> TYPE: PRT
<213> ORGANISM: Homo sapiens

<400> SEQUENCE: 17

Asn Trp Asn Glu Met Gly Val Arg
1               5

<210> SEQ ID NO 18
<211> LENGTH: 16
<212> TYPE: PRT
<213> ORGANISM: Homo sapiens

<400> SEQUENCE: 18

Arg Asp His Val Lys Asp Asp Pro Gly Ile Pro Ile Asn Ala Gly Asp
1               5                  10                  15

<210> SEQ ID NO 19
<211> LENGTH: 27
<212> TYPE: PRT
<213> ORGANISM: Homo sapiens
```

-continued

<400> SEQUENCE: 19

Trp Leu Thr Phe Cys Ala His Asp His Arg Pro Lys Val Gln Ser Gln
1               5                   10                  15

Asn Pro Arg Asn Gly Ala Ala Gly Glu Pro Ala
            20                  25

<210> SEQ ID NO 20
<211> LENGTH: 240
<212> TYPE: PRT
<213> ORGANISM: Homo sapiens

<400> SEQUENCE: 20

Val Val Gly Gly Thr Glu Ala Gln Arg Asn Ser Trp Pro Ser Gln Ile
1               5                   10                  15

Ser Leu Gln Tyr Arg Ser Gly Ser Ser Trp Ala His Thr Cys Gly Gly
            20                  25                  30

Thr Leu Ile Arg Gln Asn Trp Val Met Thr Ala Ala His Cys Val Asp
        35                  40                  45

Arg Glu Leu Thr Phe Arg Val Val Gly Glu His Asn Leu Asn Gln
    50                  55                  60

Asn Asp Gly Thr Glu Gln Tyr Val Gly Val Gln Lys Ile Val Val His
65                  70                  75                  80

Pro Tyr Trp Asn Thr Asp Asp Val Ala Ala Gly Tyr Asp Ile Ala Leu
                85                  90                  95

Leu Arg Leu Ala Gln Ser Val Thr Leu Asn Ser Tyr Val Gln Leu Gly
            100                 105                 110

Val Leu Pro Arg Ala Gly Thr Ile Leu Ala Asn Asn Ser Pro Cys Tyr
        115                 120                 125

Ile Thr Gly Trp Gly Leu Thr Arg Thr Asn Gly Gln Leu Ala Gln Thr
    130                 135                 140

Leu Gln Gln Ala Tyr Leu Pro Thr Val Asp Tyr Ala Ile Cys Ser Ser
145                 150                 155                 160

Ser Ser Tyr Trp Gly Ser Thr Val Lys Asn Ser Met Val Cys Ala Gly
                165                 170                 175

Gly Asp Gly Val Arg Ser Gly Cys Gln Gly Asp Ser Gly Gly Pro Leu
            180                 185                 190

His Cys Leu Val Asn Gly Gln Tyr Ala Val His Gly Val Thr Ser Phe
        195                 200                 205

Val Ser Arg Leu Gly Cys Asn Val Thr Arg Lys Pro Thr Val Phe Thr
    210                 215                 220

Arg Val Ser Ala Tyr Ile Ser Trp Ile Asn Asn Val Ile Ala Ser Asn
225                 230                 235                 240

<210> SEQ ID NO 21
<211> LENGTH: 240
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 21

Xaa Val Gly Gly Thr Glu Ala Gln Arg Asn Ser Trp Pro Ser Gln Ile
1               5                   10                  15

Ser Leu Gln Tyr Arg Ser Gly Ser Ser Trp Ala His Thr Cys Gly Gly
            20                  25                  30

```
Thr Leu Ile Arg Gln Asn Trp Val Met Thr Ala Ala His Cys Val Asp
             35                  40                  45

Arg Glu Leu Thr Phe Arg Val Val Gly Glu His Asn Leu Asn Gln
 50                  55                  60

Asn Asp Gly Thr Glu Gln Tyr Val Gly Val Gln Lys Ile Val Val His
 65                  70                  75                  80

Pro Tyr Trp Asn Thr Asp Asp Val Ala Ala Gly Tyr Asp Ile Ala Leu
                 85                  90                  95

Leu Arg Leu Ala Gln Ser Val Thr Leu Asn Ser Tyr Val Gln Leu Gly
                100                 105                 110

Val Leu Pro Arg Ala Gly Thr Ile Leu Ala Asn Asn Ser Pro Cys Tyr
            115                 120                 125

Ile Thr Gly Trp Gly Leu Thr Arg Thr Asn Gly Gln Leu Ala Gln Thr
130                 135                 140

Leu Gln Gln Ala Tyr Leu Pro Thr Val Asp Tyr Ala Ile Cys Ser Ser
145                 150                 155                 160

Ser Ser Tyr Trp Gly Ser Thr Val Lys Asn Ser Met Val Cys Ala Gly
                165                 170                 175

Gly Asp Gly Val Arg Ser Gly Cys Gln Gly Asp Ser Gly Gly Pro Leu
            180                 185                 190

His Cys Leu Val Asn Gly Gln Tyr Ala Val His Gly Val Thr Ser Phe
        195                 200                 205

Val Ser Arg Leu Gly Cys Asn Val Thr Arg Lys Pro Thr Val Phe Thr
    210                 215                 220

Arg Val Ser Ala Tyr Ile Ser Trp Ile Asn Asn Val Ile Ala Ser Asn
225                 230                 235                 240

<210> SEQ ID NO 22
<211> LENGTH: 240
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 22

Xaa Val Gly Gly Thr Glu Ala Gln Arg Asn Ser Trp Pro Ser Gln Ile
 1               5                  10                  15

Ser Leu Gln Tyr Arg Ser Gly Ser Ser Trp Ala His Thr Cys Gly Gly
             20                  25                  30

Thr Leu Ile Arg Gln Asn Trp Val Met Thr Ala Ala His Cys Val Asp
             35                  40                  45

Arg Glu Leu Thr Phe Arg Val Val Val Gly Glu His Asn Leu Asn Gln
 50                  55                  60

Asn Asp Gly Thr Glu Gln Tyr Val Gly Val Gln Lys Ile Val Val His
 65                  70                  75                  80

Pro Tyr Trp Asn Thr Asp Asp Val Ala Ala Gly Tyr Asp Ile Ala Leu
                 85                  90                  95

Leu Arg Leu Ala Gln Ser Val Thr Leu Asn Ser Tyr Val Gln Leu Gly
                100                 105                 110

Val Leu Pro Arg Ala Gly Thr Ile Leu Ala Asn Asn Ser Pro Cys Tyr
            115                 120                 125

Ile Thr Gly Trp Gly Leu Thr Arg Thr Asn Gly Gln Leu Ala Gln Thr
130                 135                 140

Leu Gln Gln Ala Tyr Leu Pro Thr Val Asp Tyr Ala Ile Cys Ser Ser
```

```
                145                 150                 155                 160
Ser Ser Tyr Trp Gly Ser Thr Val Lys Asn Ser Met Val Cys Ala Gly
                    165                 170                 175

Gly Asp Gly Val Arg Ser Gly Cys Gln Gly Asp Ser Gly Gly Pro Leu
                    180                 185                 190

His Cys Leu Val Asn Gly Gln Tyr Ala Val His Gly Val Thr Ser Phe
                    195                 200                 205

Val Ser Arg Leu Gly Cys Asn Val Thr Arg Lys Pro Thr Val Phe Thr
210                 215                 220

Arg Val Ser Ala Tyr Ile Ser Trp Ile Asn Asn Val Ile Ala Ser Asn
225                 230                 235                 240

<210> SEQ ID NO 23
<211> LENGTH: 112
<212> TYPE: PRT
<213> ORGANISM: Homo sapiens

<400> SEQUENCE: 23

Met Glu Lys Val Leu Ala Leu Leu Leu Val Thr Leu Thr Val Ala Tyr
1               5                   10                  15

Ala Val Pro Asp Pro Arg Gly Ile Ile Ile Asn Leu Asp Glu Gly Glu
                20                  25                  30

Leu Cys Leu Asn Ser Ala Gln Cys Lys Ser Asn Cys Cys Gln His Asp
            35                  40                  45

Thr Ile Leu Ser Leu Ser Arg Cys Ala Leu Lys Ala Arg Glu Asn Ser
        50                  55                  60

Glu Cys Ser Ala Phe Thr Leu Tyr Gly Val Tyr Tyr Lys Cys Pro Cys
65                  70                  75                  80

Glu Arg Gly Leu Thr Cys Glu Gly Asp Lys Ser Leu Val Gly Ser Ile
                85                  90                  95

Thr Asn Thr Asn Phe Gly Ile Cys His Asp Val Gly Arg Ser Ser Asp
                100                 105                 110

<210> SEQ ID NO 24
<211> LENGTH: 240
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 24

Xaa Val Gly Gly Thr Glu Ala Gln Arg Asn Ser Trp Pro Ser Gln Ile
1               5                   10                  15

Ser Leu Gln Tyr Arg Ser Gly Ser Ser Trp Ala His Thr Cys Gly Gly
                20                  25                  30

Thr Leu Ile Arg Gln Asn Trp Val Met Thr Ala Ala His Cys Val Asp
            35                  40                  45

Arg Glu Leu Thr Phe Arg Val Val Val Gly Glu His Asn Leu Asn Gln
        50                  55                  60

Asn Asp Gly Thr Glu Gln Tyr Val Gly Val Gln Lys Ile Val Val His
65                  70                  75                  80

Pro Tyr Trp Asn Thr Asp Asp Val Ala Ala Gly Tyr Asp Ile Ala Leu
                85                  90                  95

Leu Arg Leu Ala Gln Ser Val Thr Leu Asn Ser Tyr Val Gln Leu Gly
                100                 105                 110
```

```
Val Leu Pro Arg Ala Gly Thr Ile Leu Ala Asn Asn Ser Pro Cys Tyr
            115                 120                 125

Ile Thr Gly Trp Gly Leu Thr Arg Thr Asn Gly Gln Leu Ala Gln Thr
    130                 135                 140

Leu Gln Gln Ala Tyr Leu Pro Thr Val Asp Tyr Ala Ile Cys Ser Ser
145                 150                 155                 160

Ser Ser Tyr Trp Gly Thr Val Lys Asn Ser Met Val Cys Ala Gly
                165                 170                 175    Gly

Gly Asp Gly Val Arg Ser Gly Cys Gln Gly Asp Ser Gly Gly Pro Leu
            180                 185                 190

His Cys Leu Val Asn Gly Gln Tyr Ala Val His Gly Val Thr Ser Phe
            195                 200                 205

Val Ser Arg Leu Gly Cys Asn Val Thr Arg Lys Pro Thr Val Phe Thr
            210                 215                 220

Arg Val Ser Ala Tyr Ile Ser Trp Ile Asn Asn Val Ile Ala Ser Asn
225                 230                 235                 240

<210> SEQ ID NO 25
<211> LENGTH: 496
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 25

Xaa Tyr Ala Pro Gln Thr Gln Ser Gly Arg Thr Ser Ile Val His Leu
1               5                   10                  15

Phe Glu Trp Arg Trp Val Asp Ile Ala Leu Glu Cys Glu Arg Tyr Leu
                20                  25                  30

Gly Pro Lys Gly Phe Gly Gly Val Gln Val Ser Pro Pro Asn Glu Asn
            35                  40                  45

Val Val Val Thr Asn Pro Ser Arg Pro Trp Trp Glu Arg Tyr Gln Pro
 50                 55                  60

Val Ser Tyr Lys Leu Cys Thr Arg Ser Gly Asn Glu Asn Glu Phe Arg
65                  70                  75                  80

Asp Met Val Thr Arg Cys Asn Asn Val Gly Val Arg Ile Tyr Val Asp
                85                  90                  95

Ala Val Ile Asn His Met Cys Gly Ser Gly Ala Ala Ala Gly Thr Gly
            100                 105                 110

Thr Thr Cys Gly Ser Tyr Cys Asn Pro Gly Ser Arg Glu Phe Pro Ala
            115                 120                 125

Val Pro Tyr Ser Ala Trp Asp Phe Asn Asp Gly Lys Cys Lys Thr Ala
    130                 135                 140

Ser Gly Gly Ile Glu Ser Tyr Asn Asp Pro Tyr Gln Val Arg Asp Cys
145                 150                 155                 160

Gln Leu Val Gly Leu Leu Asp Leu Ala Leu Glu Lys Asp Tyr Val Arg
                165                 170                 175

Ser Met Ile Ala Asp Tyr Leu Asn Lys Leu Ile Asp Ile Gly Val Ala
            180                 185                 190

Gly Phe Arg Ile Asp Ala Ser Lys His Met Trp Pro Gly Asp Ile Lys
            195                 200                 205

Ala Val Leu Asp Lys Leu His Asn Leu Asn Thr Asn Trp Phe Pro Ala
    210                 215                 220

Gly Ser Arg Pro Phe Ile Phe Gln Glu Val Ile Asp Leu Gly Gly Glu
```

```
                    225                 230                 235                 240

Ala Ile Gln Ser Ser Glu Tyr Phe Gly Asn Gly Arg Val Thr Glu Phe
                        245                 250                 255

Lys Tyr Gly Ala Lys Leu Gly Thr Val Val Arg Lys Trp Ser Gly Glu
                    260                 265                 270

Lys Met Ser Tyr Leu Lys Asn Trp Gly Glu Gly Trp Gly Phe Met Pro
                275                 280                 285

Ser Asp Arg Ala Leu Val Phe Val Asp Asn His Asp Asn Gln Arg Gly
            290                 295                 300

His Gly Ala Gly Gly Ala Ser Ile Leu Thr Phe Trp Asp Ala Arg Leu
        305                 310                 315                 320

Tyr Lys Val Ala Val Gly Phe Met Leu Ala His Pro Tyr Gly Phe Thr
                        325                 330                 335

Arg Val Met Ser Ser Tyr Arg Trp Ala Arg Asn Phe Val Asn Gly Glu
                    340                 345                 350

Asp Val Asn Asp Trp Ile Gly Pro Pro Asn Asn Asn Gly Val Ile Lys
                355                 360                 365

Glu Val Thr Ile Asn Ala Asp Thr Thr Cys Gly Asn Asp Trp Val Cys
            370                 375                 380

Glu His Arg Trp Arg Glu Ile Arg Asn Met Val Trp Phe Arg Asn Val
        385                 390                 395                 400

Val Asp Gly Gln Pro Phe Ala Asn Trp Trp Asp Asn Gly Ser Asn Gln
                        405                 410                 415

Val Ala Phe Gly Arg Gly Asn Arg Gly Phe Ile Val Phe Asn Asn Asp
                    420                 425                 430

Asp Trp Gln Leu Ser Ser Thr Leu Gln Thr Gly Leu Pro Gly Gly Thr
                435                 440                 445

Tyr Cys Asp Val Ile Ser Gly Asp Lys Val Gly Asn Ser Cys Thr Gly
            450                 455                 460

Ile Lys Val Tyr Val Ser Ser Asp Gly Thr Ala Gln Phe Ser Ile Ser
        465                 470                 475                 480

Asn Ser Ala Glu Asp Pro Phe Ile Ala Ile His Ala Glu Ser Lys Leu
                        485                 490                 495

<210> SEQ ID NO 26
<211> LENGTH: 496
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 26

Xaa Tyr Ala Pro Gln Thr Gln Ser Gly Arg Thr Ser Ile Val His Leu
        1               5                   10                  15

Phe Glu Trp Arg Trp Val Asp Ile Ala Leu Glu Cys Glu Arg Tyr Leu
                        20                  25                  30

Gly Pro Lys Gly Phe Gly Gly Val Gln Val Ser Pro Pro Asn Glu Asn
                    35                  40                  45

Val Val Val Thr Asn Pro Ser Arg Pro Trp Trp Glu Arg Tyr Gln Pro
                50                  55                  60

Val Ser Tyr Lys Leu Cys Thr Arg Ser Gly Asn Glu Asn Glu Phe Arg
        65                  70                  75                  80

Asp Met Val Thr Arg Cys Asn Asn Val Gly Val Arg Ile Tyr Val Asp
                        85                  90                  95
```

-continued

Ala Val Ile Asn His Met Cys Gly Ser Gly Ala Ala Gly Thr Gly
            100                 105             110

Thr Thr Cys Gly Ser Tyr Cys Asn Pro Gly Ser Arg Glu Phe Pro Ala
        115                 120                 125

Val Pro Tyr Ser Ala Trp Asp Phe Asn Asp Gly Lys Cys Lys Thr Ala
130                 135                 140

Ser Gly Gly Ile Glu Ser Tyr Asn Asp Pro Tyr Gln Val Arg Asp Cys
145                 150                 155                 160

Gln Leu Val Gly Leu Leu Asp Leu Ala Leu Glu Lys Asp Tyr Val Arg
                165                 170                 175

Ser Met Ile Ala Asp Tyr Leu Asn Lys Leu Ile Asp Ile Gly Val Ala
            180                 185                 190

Gly Phe Arg Ile Asp Ala Ser Lys His Met Trp Pro Gly Asp Ile Lys
        195                 200                 205

Ala Val Leu Asp Lys Leu His Asn Leu Asn Thr Asn Trp Phe Pro Ala
210                 215                 220

Gly Ser Arg Pro Phe Ile Phe Gln Glu Val Ile Asp Leu Gly Gly Glu
225                 230                 235                 240

Ala Ile Gln Ser Ser Glu Tyr Phe Gly Asn Gly Arg Val Thr Glu Phe
                245                 250                 255

Lys Tyr Gly Ala Lys Leu Gly Thr Val Val Arg Lys Trp Ser Gly Glu
            260                 265                 270

Lys Met Ser Tyr Leu Lys Asn Trp Gly Glu Gly Trp Gly Phe Met Pro
        275                 280                 285

Ser Asp Arg Ala Leu Val Phe Val Asp Asn His Asp Asn Gln Arg Gly
290                 295                 300

His Gly Ala Gly Gly Ala Ser Ile Leu Thr Phe Trp Asp Ala Arg Leu
305                 310                 315                 320

Tyr Lys Val Ala Val Gly Phe Met Leu Ala His Pro Tyr Gly Phe Thr
                325                 330                 335

Arg Val Met Ser Ser Tyr Arg Trp Ala Arg Asn Phe Val Asn Gly Glu
            340                 345                 350

Asp Val Asn Asp Trp Ile Gly Pro Pro Asn Asn Asn Gly Val Ile Lys
        355                 360                 365

Glu Val Thr Ile Asn Ala Asp Thr Thr Cys Gly Asn Asp Trp Val Cys
370                 375                 380

Glu His Arg Trp Arg Glu Ile Arg Asn Met Val Trp Phe Arg Asn Val
385                 390                 395                 400

Val Asp Gly Gln Pro Phe Ala Asn Trp Trp Asp Asn Gly Ser Asn Gln
                405                 410                 415

Val Ala Phe Gly Arg Gly Asn Arg Gly Phe Ile Val Phe Asn Asn Asp
            420                 425                 430

Asp Trp Gln Leu Ser Ser Thr Leu Gln Thr Gly Leu Pro Gly Gly Thr
        435                 440                 445

Tyr Cys Asp Val Ile Ser Gly Asp Lys Val Gly Asn Ser Cys Thr Gly
450                 455                 460

Ile Lys Val Tyr Val Ser Ser Asp Gly Thr Ala Gln Phe Ser Ile Ser
465                 470                 475                 480

Asn Ser Ala Glu Asp Pro Phe Ile Ala Ile His Ala Glu Ser Lys Leu
                485                 490                 495

<210> SEQ ID NO 27
<211> LENGTH: 511

<212> TYPE: PRT
<213> ORGANISM: Homo sapiens

<400> SEQUENCE: 27

```
Met Lys Leu Phe Leu Leu Ser Ala Phe Gly Phe Cys Trp Ala Gln
1               5                   10                  15

Tyr Ala Pro Gln Thr Gln Ser Gly Arg Thr Ser Ile Val His Leu Phe
            20                  25                  30

Glu Trp Arg Trp Val Asp Ile Ala Leu Glu Cys Glu Arg Tyr Leu Gly
        35                  40                  45

Pro Lys Gly Phe Gly Gly Val Gln Val Ser Pro Pro Asn Glu Asn Ile
    50                  55                  60

Val Val Thr Asn Pro Ser Arg Pro Trp Trp Glu Arg Tyr Gln Pro Val
65                  70                  75                  80

Ser Tyr Lys Leu Cys Thr Arg Ser Gly Asn Glu Asn Glu Phe Arg Asp
                85                  90                  95

Met Val Thr Arg Cys Asn Asn Val Gly Val Arg Ile Tyr Val Asp Ala
            100                 105                 110

Val Ile Asn His Met Cys Gly Ser Gly Ala Ala Ala Gly Thr Gly Thr
        115                 120                 125

Thr Cys Gly Ser Tyr Cys Asn Pro Gly Asn Arg Glu Phe Pro Ala Val
130                 135                 140

Pro Tyr Ser Ala Trp Asp Phe Asn Asp Gly Lys Cys Lys Thr Ala Ser
145                 150                 155                 160

Gly Gly Ile Glu Ser Tyr Asn Asp Pro Tyr Gln Val Arg Asp Cys Gln
                165                 170                 175

Leu Val Gly Leu Leu Asp Leu Ala Leu Glu Lys Asp Tyr Val Arg Ser
            180                 185                 190

Met Ile Ala Asp Tyr Leu Asn Lys Leu Ile Asp Ile Gly Val Ala Gly
        195                 200                 205

Phe Arg Ile Asp Ala Ser Lys His Met Trp Pro Gly Asp Ile Lys Ala
    210                 215                 220

Val Leu Asp Lys Leu His Asn Leu Asn Thr Asn Trp Phe Pro Ala Gly
225                 230                 235                 240

Ser Arg Pro Phe Ile Phe Gln Glu Val Ile Asp Leu Gly Gly Glu Ala
                245                 250                 255

Ile Gln Ser Ser Glu Tyr Phe Gly Asn Gly Arg Val Thr Glu Phe Lys
            260                 265                 270

Tyr Gly Ala Lys Leu Gly Thr Val Val Arg Lys Trp Ser Gly Glu Lys
        275                 280                 285

Met Ser Tyr Leu Lys Asn Trp Gly Glu Gly Trp Gly Phe Met Pro Ser
    290                 295                 300

Asp Arg Ala Leu Val Phe Val Asp Asn His Asp Asn Gln Arg Gly His
305                 310                 315                 320

Gly Ala Gly Gly Ala Ser Ile Leu Thr Phe Trp Asp Ala Arg Leu Tyr
                325                 330                 335

Lys Val Ala Val Gly Phe Met Leu Ala His Pro Tyr Gly Phe Thr Arg
            340                 345                 350

Val Met Ser Ser Tyr Arg Trp Ala Arg Asn Phe Val Asn Gly Gln Asp
        355                 360                 365

Val Asn Asp Trp Ile Gly Pro Pro Asn Asn Gly Val Ile Lys Glu
    370                 375                 380

Val Thr Ile Asn Ala Asp Thr Thr Cys Gly Asn Asp Trp Val Cys Glu
385                 390                 395                 400
```

```
His Arg Trp Arg Gln Ile Arg Asn Met Val Trp Phe Arg Asn Val Val
                405                 410                 415

Asp Gly Gln Pro Phe Ala Asn Trp Trp Ala Asn Gly Ser Asn Gln Val
            420                 425                 430

Ala Phe Gly Arg Gly Asn Arg Gly Phe Ile Val Phe Asn Asn Asp Asp
        435                 440                 445

Trp Gln Leu Ser Ser Thr Leu Gln Thr Gly Leu Pro Gly Gly Thr Tyr
    450                 455                 460

Cys Asp Val Ile Ser Gly Asp Lys Val Gly Asn Ser Cys Thr Gly Ile
465                 470                 475                 480

Lys Val Tyr Val Ser Ser Asp Gly Thr Ala Gln Phe Ser Ile Ser Asn
                485                 490                 495

Ser Ala Glu Asp Pro Phe Ile Ala Ile His Ala Glu Ser Lys Leu
            500                 505                 510

<210> SEQ ID NO 28
<211> LENGTH: 496
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 28

Xaa Tyr Ala Pro Gln Thr Gln Ser Gly Arg Thr Ser Ile Val His Leu
1               5                   10                  15

Phe Glu Trp Arg Trp Val Asp Ile Ala Leu Glu Cys Glu Arg Tyr Leu
                20                  25                  30

Gly Pro Lys Gly Phe Gly Gly Val Gln Val Ser Pro Pro Asn Glu Asn
            35                  40                  45

Val Val Val Thr Asn Pro Ser Arg Pro Trp Trp Glu Arg Tyr Gln Pro
    50                  55                  60

Val Ser Tyr Lys Leu Cys Thr Arg Ser Gly Asn Glu Asn Glu Phe Arg
65                  70                  75                  80

Asp Met Val Thr Arg Cys Asn Asn Val Gly Val Arg Ile Tyr Val Asp
                85                  90                  95

Ala Val Ile Asn His Met Cys Gly Ser Gly Ala Ala Ala Gly Thr Gly
            100                 105                 110

Thr Thr Cys Gly Ser Tyr Cys Asn Pro Gly Ser Arg Glu Phe Pro Ala
        115                 120                 125

Val Pro Tyr Ser Ala Trp Asp Phe Asn Asp Gly Lys Cys Lys Thr Ala
    130                 135                 140

Ser Gly Gly Ile Glu Ser Tyr Asn Asp Pro Tyr Gln Val Arg Asp Cys
145                 150                 155                 160

Gln Leu Val Gly Leu Leu Asp Leu Ala Leu Glu Lys Asp Tyr Val Arg
                165                 170                 175

Ser Met Ile Ala Asp Tyr Leu Asn Lys Leu Ile Asp Ile Gly Val Ala
            180                 185                 190

Gly Phe Arg Ile Asp Ala Ser Lys His Met Trp Pro Gly Asp Ile Lys
        195                 200                 205

Ala Val Leu Asp Lys Leu His Asn Leu Asn Thr Asn Trp Phe Pro Ala
    210                 215                 220

Gly Ser Arg Pro Phe Ile Phe Gln Glu Val Ile Asp Leu Gly Gly Glu
225                 230                 235                 240
```

```
Ala Ile Gln Ser Ser Glu Tyr Phe Gly Asn Gly Arg Val Thr Glu Phe
                245                 250                 255

Lys Tyr Gly Ala Lys Leu Gly Thr Val Val Arg Lys Trp Ser Gly Glu
            260                 265                 270

Lys Met Ser Tyr Leu Lys Asn Trp Gly Glu Gly Trp Gly Phe Met Pro
        275                 280                 285

Ser Asp Arg Ala Leu Val Phe Val Asp Asn His Asp Asn Gln Arg Gly
    290                 295                 300

His Gly Ala Gly Gly Ala Ser Ile Leu Thr Phe Trp Asp Ala Arg Leu
305                 310                 315                 320

Tyr Lys Val Ala Val Gly Phe Met Leu Ala His Pro Tyr Gly Phe Thr
                325                 330                 335

Arg Val Met Ser Ser Tyr Arg Trp Ala Arg Asn Phe Val Asn Gly Glu
            340                 345                 350

Asp Val Asn Asp Trp Ile Gly Pro Pro Asn Asn Asn Gly Val Ile Lys
        355                 360                 365

Glu Val Thr Ile Asn Ala Asp Thr Thr Cys Gly Asn Asp Trp Val Cys
    370                 375                 380

Glu His Arg Trp Arg Glu Ile Arg Asn Met Val Trp Phe Arg Asn Val
385                 390                 395                 400

Val Asp Gly Gln Pro Phe Ala Asn Trp Trp Asp Asn Gly Ser Asn Gln
                405                 410                 415

Val Ala Phe Gly Arg Gly Asn Arg Gly Phe Ile Val Phe Asn Asn Asp
            420                 425                 430

Asp Trp Gln Leu Ser Ser Thr Leu Gln Thr Gly Leu Pro Gly Gly Thr
        435                 440                 445

Tyr Cys Asp Val Ile Ser Gly Asp Lys Val Gly Asn Ser Cys Thr Gly
    450                 455                 460

Ile Lys Val Tyr Val Ser Ser Asp Gly Thr Ala Gln Phe Ser Ile Ser
465                 470                 475                 480

Asn Ser Ala Glu Asp Pro Phe Ile Ala Ile His Ala Glu Ser Lys Leu
                485                 490                 495

<210> SEQ ID NO 29
<211> LENGTH: 416
<212> TYPE: PRT
<213> ORGANISM: Homo sapiens

<400> SEQUENCE: 29

Met Leu Ala Phe Leu Ile Leu Val Thr Val Thr Leu Ala Ser Ala His
1               5                   10                  15

His Ser Gly Glu His Phe Glu Gly Glu Lys Val Phe Arg Val Asn Val
            20                  25                  30

Glu Asp Glu Asn Asp Ile Ser Leu Leu His Glu Leu Ala Ser Thr Arg
        35                  40                  45

Gln Ile Asp Phe Trp Lys Pro Asp Ser Val Thr Gln Ile Lys Pro His
    50                  55                  60

Ser Thr Val Asp Phe Arg Val Lys Ala Glu Asp Ile Leu Ala Val Glu
65                  70                  75                  80

Asp Phe Leu Glu Gln Asn Glu Leu Gln Tyr Glu Val Leu Ile Asn Asn
                85                  90                  95

Leu Arg Ser Val Leu Glu Ala Gln Phe Asp Ser Arg Val Arg Thr Thr
            100                 105                 110

Gly His Ser Tyr Glu Lys Tyr Asn Asn Trp Glu Thr Ile Glu Ala Trp
        115                 120                 125
```

Thr Lys Gln Val Thr Ser Glu Asn Pro Asp Leu Ile Ser Arg Thr Ala
            130                 135                 140

Ile Gly Thr Thr Phe Leu Gly Asn Asn Ile Tyr Leu Leu Lys Val Gly
145                 150                 155                 160

Lys Pro Gly Pro Asn Lys Pro Ala Ile Phe Met Asp Cys Gly Phe His
                    165                 170                 175

Ala Arg Glu Trp Ile Ser His Ala Phe Cys Gln Trp Phe Val Arg Glu
            180                 185                 190

Ala Val Leu Thr Tyr Gly Tyr Glu Ser His Met Thr Glu Phe Leu Asn
        195                 200                 205

Lys Leu Asp Phe Tyr Val Leu Pro Val Leu Asn Ile Asp Gly Tyr Ile
    210                 215                 220

Tyr Thr Trp Thr Lys Asn Arg Met Trp Arg Lys Thr Arg Ser Thr Asn
225                 230                 235                 240

Ala Gly Thr Thr Cys Ile Gly Thr Asp Pro Asn Arg Asn Phe Asp Ala
                245                 250                 255

Gly Trp Cys Thr Thr Gly Ala Ser Thr Asp Pro Cys Asp Glu Thr Tyr
            260                 265                 270

Cys Gly Ser Ala Ala Glu Ser Glu Lys Glu Thr Lys Ala Leu Ala Asp
        275                 280                 285

Phe Ile Arg Asn Asn Leu Ser Ser Ile Lys Ala Tyr Leu Thr Ile His
    290                 295                 300

Ser Tyr Ser Gln Met Ile Leu Tyr Pro Tyr Ser Tyr Asp Tyr Lys Leu
305                 310                 315                 320

Pro Glu Asn Asn Ala Glu Leu Asn Asn Leu Ala Lys Ala Ala Val Lys
                325                 330                 335

Glu Leu Ala Thr Leu Tyr Gly Thr Lys Tyr Thr Tyr Gly Pro Gly Ala
            340                 345                 350

Thr Thr Ile Tyr Pro Ala Ala Gly Gly Ser Asp Asp Trp Ala Tyr Asp
        355                 360                 365

Gln Gly Ile Lys Tyr Ser Phe Thr Phe Glu Leu Arg Asp Lys Gly Arg
    370                 375                 380

Tyr Gly Phe Ile Leu Pro Glu Ser Gln Ile Gln Ala Thr Cys Glu Glu
385                 390                 395                 400

Thr Met Leu Ala Ile Lys Tyr Val Thr Asn Tyr Val Leu Gly His Leu
                405                 410                 415

<210> SEQ ID NO 30
<211> LENGTH: 511
<212> TYPE: PRT
<213> ORGANISM: Homo sapiens

<400> SEQUENCE: 30

Met Lys Leu Phe Leu Leu Leu Ser Ala Phe Gly Phe Cys Trp Ala Gln
1               5                   10                  15

Tyr Ala Pro Gln Thr Gln Ser Gly Arg Thr Ser Ile Val His Leu Phe
            20                  25                  30

Glu Trp Arg Trp Val Asp Ile Ala Leu Glu Cys Glu Arg Tyr Leu Gly
        35                  40                  45

Pro Lys Gly Phe Gly Gly Val Gln Val Ser Pro Asn Glu Asn Ile
    50                  55                  60

Val Val Thr Asn Pro Ser Arg Pro Trp Trp Glu Arg Tyr Gln Pro Val
65                  70                  75                  80

Ser Tyr Lys Leu Cys Thr Arg Ser Gly Asn Glu Asn Glu Phe Arg Asp 85                  90                  95
Met Val Thr Arg Cys Asn Asn Val Gly Val Arg Ile Tyr Val Asp Ala
                100                 105                 110

Val Ile Asn His Met Cys Gly Ser Gly Ala Ala Gly Thr Gly Thr
            115                 120                 125

Thr Cys Gly Ser Tyr Cys Asn Pro Gly Asn Arg Glu Phe Pro Ala Val
            130                 135                 140

Pro Tyr Ser Ala Trp Asp Phe Asn Asp Gly Lys Cys Lys Thr Ala Ser
145                 150                 155                 160

Gly Gly Ile Glu Ser Tyr Asn Asp Pro Tyr Gln Val Arg Asp Cys Gln
                165                 170                 175

Leu Val Gly Leu Leu Asp Leu Ala Leu Glu Lys Asp Tyr Val Arg Ser
            180                 185                 190

Met Ile Ala Asp Tyr Leu Asn Lys Leu Ile Asp Ile Gly Val Ala Gly
        195                 200                 205

Phe Arg Ile Asp Ala Ser Lys His Met Trp Pro Gly Asp Ile Lys Ala
    210                 215                 220

Val Leu Asp Lys Leu His Asn Leu Asn Thr Asn Trp Phe Pro Ala Gly
225                 230                 235                 240

Ser Arg Pro Phe Ile Phe Gln Glu Val Ile Asp Leu Gly Gly Glu Ala
                245                 250                 255

Ile Gln Ser Ser Glu Tyr Phe Gly Asn Gly Arg Val Thr Glu Phe Lys
            260                 265                 270

Tyr Gly Ala Lys Leu Gly Thr Val Val Arg Lys Trp Ser Gly Glu Lys
            275                 280                 285

Met Ser Tyr Leu Lys Asn Trp Gly Glu Gly Trp Gly Phe Met Pro Ser
        290                 295                 300

Asp Arg Ala Leu Val Phe Val Asp Asn His Asp Asn Gln Arg Gly His
305                 310                 315                 320

Gly Ala Gly Gly Ala Ser Ile Leu Thr Phe Trp Asp Ala Arg Leu Tyr
                325                 330                 335

Lys Val Ala Val Gly Phe Met Leu Ala His Pro Tyr Gly Phe Thr Arg
            340                 345                 350

Val Met Ser Ser Tyr Arg Trp Ala Arg Asn Phe Val Asn Gly Gln Asp
            355                 360                 365

Val Asn Asp Trp Ile Gly Pro Pro Asn Asn Gly Val Ile Lys Glu
        370                 375                 380

Val Thr Ile Asn Ala Asp Thr Thr Cys Gly Asn Asp Trp Val Cys Glu
385                 390                 395                 400

His Arg Trp Arg Gln Ile Arg Asn Met Val Trp Phe Arg Asn Val Val
                405                 410                 415

Asp Gly Gln Pro Phe Ala Asn Trp Trp Ala Asn Gly Ser Asn Gln Val
            420                 425                 430

Ala Phe Gly Arg Gly Asn Arg Gly Phe Ile Val Phe Asn Asn Asp Asp
            435                 440                 445

Trp Gln Leu Ser Ser Thr Leu Gln Thr Gly Leu Pro Gly Gly Thr Tyr
        450                 455                 460

Cys Asp Val Ile Ser Gly Asp Lys Val Gly Asn Ser Cys Thr Gly Ile
465                 470                 475                 480

Lys Val Tyr Val Ser Ser Asp Gly Thr Ala Gln Phe Ser Ile Ser Asn
                485                 490                 495

Ser Ala Glu Asp Pro Phe Ile Ala Ile His Ala Glu Ser Lys Leu
            500                 505                 510

```
<210> SEQ ID NO 31
<211> LENGTH: 496
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 31
```

| | | | | | | | | | | | | | | | |
|---|---|---|---|---|---|---|---|---|---|---|---|---|---|---|---|
| Xaa | Tyr | Ala | Pro | Gln | Thr | Gln | Ser | Gly | Arg | Thr | Ser | Ile | Val | His | Leu |
| 1 | | | | 5 | | | | | 10 | | | | | 15 | |
| Phe | Glu | Trp | Arg | Trp | Val | Asp | Ile | Ala | Leu | Glu | Cys | Glu | Arg | Tyr | Leu |
| | | | 20 | | | | | 25 | | | | | 30 | | |
| Gly | Pro | Lys | Gly | Phe | Gly | Gly | Val | Gln | Val | Ser | Pro | Pro | Asn | Glu | Asn |
| | | | 35 | | | | | 40 | | | | | 45 | | |
| Val | Val | Val | Thr | Asn | Pro | Ser | Arg | Pro | Trp | Trp | Glu | Arg | Tyr | Gln | Pro |
| | 50 | | | | | 55 | | | | | 60 | | | | |
| Val | Ser | Tyr | Lys | Leu | Cys | Thr | Arg | Ser | Gly | Asn | Glu | Asn | Glu | Phe | Arg |
| 65 | | | | | 70 | | | | | 75 | | | | | 80 |
| Asp | Met | Val | Thr | Arg | Cys | Asn | Asn | Val | Gly | Val | Arg | Ile | Tyr | Val | Asp |
| | | | | 85 | | | | | 90 | | | | | 95 | |
| Ala | Val | Ile | Asn | His | Met | Cys | Gly | Ser | Gly | Ala | Ala | Gly | Thr | Gly |
| | | | 100 | | | | | 105 | | | | | 110 | | |
| Thr | Thr | Cys | Gly | Ser | Tyr | Cys | Asn | Pro | Gly | Ser | Arg | Glu | Phe | Pro | Ala |
| | | | 115 | | | | | 120 | | | | | 125 | | |
| Val | Pro | Tyr | Ser | Ala | Trp | Asp | Phe | Asn | Asp | Gly | Lys | Cys | Lys | Thr | Ala |
| | 130 | | | | | 135 | | | | | 140 | | | | |
| Ser | Gly | Gly | Ile | Glu | Ser | Tyr | Asn | Asp | Pro | Tyr | Gln | Val | Arg | Asp | Cys |
| 145 | | | | | 150 | | | | | 155 | | | | | 160 |
| Gln | Leu | Val | Gly | Leu | Leu | Asp | Leu | Ala | Leu | Glu | Lys | Asp | Tyr | Val | Arg |
| | | | | 165 | | | | | 170 | | | | | 175 | |
| Ser | Met | Ile | Ala | Asp | Tyr | Leu | Asn | Lys | Leu | Ile | Asp | Ile | Gly | Val | Ala |
| | | | 180 | | | | | 185 | | | | | 190 | | |
| Gly | Phe | Arg | Ile | Asp | Ala | Ser | Lys | His | Met | Trp | Pro | Gly | Asp | Ile | Lys |
| | | | 195 | | | | | 200 | | | | | 205 | | |
| Ala | Val | Leu | Asp | Lys | Leu | His | Asn | Leu | Asn | Thr | Asn | Trp | Phe | Pro | Ala |
| | 210 | | | | | 215 | | | | | 220 | | | | |
| Gly | Ser | Arg | Pro | Phe | Ile | Phe | Gln | Glu | Val | Ile | Asp | Leu | Gly | Gly | Glu |
| 225 | | | | | 230 | | | | | 235 | | | | | 240 |
| Ala | Ile | Gln | Ser | Ser | Glu | Tyr | Phe | Gly | Asn | Gly | Arg | Val | Thr | Glu | Phe |
| | | | | 245 | | | | | 250 | | | | | 255 | |
| Lys | Tyr | Gly | Ala | Lys | Leu | Gly | Thr | Val | Val | Arg | Lys | Trp | Ser | Gly | Glu |
| | | | 260 | | | | | 265 | | | | | 270 | | |
| Lys | Met | Ser | Tyr | Leu | Lys | Asn | Trp | Gly | Glu | Gly | Trp | Gly | Phe | Met | Pro |
| | | | 275 | | | | | 280 | | | | | 285 | | |
| Ser | Asp | Arg | Ala | Leu | Val | Phe | Val | Asp | Asn | His | Asp | Asn | Gln | Arg | Gly |
| | 290 | | | | | 295 | | | | | 300 | | | | |
| His | Gly | Ala | Gly | Gly | Ala | Ser | Ile | Leu | Thr | Phe | Trp | Asp | Ala | Arg | Leu |
| 305 | | | | | 310 | | | | | 315 | | | | | 320 |
| Tyr | Lys | Val | Ala | Val | Gly | Phe | Met | Leu | Ala | His | Pro | Tyr | Gly | Phe | Thr |
| | | | | 325 | | | | | 330 | | | | | 335 | |
| Arg | Val | Met | Ser | Ser | Tyr | Arg | Trp | Ala | Arg | Asn | Phe | Val | Asn | Gly | Glu |
| | | | 340 | | | | | 345 | | | | | 350 | | |

Asp Val Asn Asp Trp Ile Gly Pro Asn Asn Gly Val Ile Lys
            355                 360                 365

Glu Val Thr Ile Asn Ala Asp Thr Thr Cys Gly Asn Asp Trp Val Cys
    370                 375                 380

Glu His Arg Trp Arg Glu Ile Arg Asn Met Val Trp Phe Arg Asn Val
385                 390                 395                 400

Val Asp Gly Gln Pro Phe Ala Asn Trp Trp Asp Asn Gly Ser Asn Gln
                405                 410                 415

Val Ala Phe Gly Arg Gly Asn Arg Gly Phe Ile Val Phe Asn Asn Asp
            420                 425                 430

Asp Trp Gln Leu Ser Ser Thr Leu Gln Thr Gly Leu Pro Gly Gly Thr
        435                 440                 445

Tyr Cys Asp Val Ile Ser Gly Asp Lys Val Gly Asn Ser Cys Thr Gly
    450                 455                 460

Ile Lys Val Tyr Val Ser Ser Asp Gly Thr Ala Gln Phe Ser Ile Ser
465                 470                 475                 480

Asn Ser Ala Glu Asp Pro Phe Ile Ala Ile His Ala Glu Ser Lys Leu
                485                 490                 495

<210> SEQ ID NO 32
<211> LENGTH: 496
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 32

Xaa Tyr Ala Pro Gln Thr Gln Ser Gly Arg Thr Ser Ile Val His Leu
1               5                   10                  15

Phe Glu Trp Arg Trp Val Asp Ile Ala Leu Glu Cys Glu Arg Tyr Leu
            20                  25                  30

Gly Pro Lys Gly Phe Gly Gly Val Gln Val Ser Pro Pro Asn Glu Asn
        35                  40                  45

Val Val Val Thr Asn Pro Ser Arg Pro Trp Trp Glu Arg Tyr Gln Pro
    50                  55                  60

Val Ser Tyr Lys Leu Cys Thr Arg Ser Gly Asn Glu Asn Glu Phe Arg
65                  70                  75                  80

Asp Met Val Thr Arg Cys Asn Asn Val Gly Val Arg Ile Tyr Val Asp
                85                  90                  95

Ala Val Ile Asn His Met Cys Gly Ser Gly Ala Ala Ala Gly Thr Gly
            100                 105                 110

Thr Thr Cys Gly Ser Tyr Cys Asn Pro Gly Ser Arg Glu Phe Pro Ala
        115                 120                 125

Val Pro Tyr Ser Ala Trp Asp Phe Asn Asp Gly Lys Cys Lys Thr Ala
    130                 135                 140

Ser Gly Gly Ile Glu Ser Tyr Asn Asp Pro Tyr Gln Val Arg Asp Cys
145                 150                 155                 160

Gln Leu Val Gly Leu Leu Asp Leu Ala Leu Glu Lys Asp Tyr Val Arg
                165                 170                 175

Ser Met Ile Ala Asp Tyr Leu Asn Lys Leu Ile Asp Ile Gly Val Ala
            180                 185                 190

Gly Phe Arg Ile Asp Ala Ser Lys His Met Trp Pro Gly Asp Ile Lys
        195                 200                 205

Ala Val Leu Asp Lys Leu His Asn Leu Asn Thr Asn Trp Phe Pro Ala

-continued

```
                210                 215                 220
Gly Ser Arg Pro Phe Ile Phe Gln Glu Val Ile Asp Leu Gly Gly Glu
225                 230                 235                 240

Ala Ile Gln Ser Ser Glu Tyr Phe Gly Asn Gly Arg Val Thr Glu Phe
                245                 250                 255

Lys Tyr Gly Ala Lys Leu Gly Thr Val Val Arg Lys Trp Ser Gly Glu
                260                 265                 270

Lys Met Ser Tyr Leu Lys Asn Trp Gly Glu Gly Trp Gly Phe Met Pro
                275                 280                 285

Ser Asp Arg Ala Leu Val Phe Val Asp Asn His Asp Asn Gln Arg Gly
                290                 295                 300

His Gly Ala Gly Gly Ala Ser Ile Leu Thr Phe Trp Asp Ala Arg Leu
305                 310                 315                 320

Tyr Lys Val Ala Val Gly Phe Met Leu Ala His Pro Tyr Gly Phe Thr
                325                 330                 335

Arg Val Met Ser Ser Tyr Arg Trp Ala Arg Asn Phe Val Asn Gly Glu
                340                 345                 350

Asp Val Asn Asp Trp Ile Gly Pro Pro Asn Asn Asn Gly Val Ile Lys
                355                 360                 365

Glu Val Thr Ile Asn Ala Asp Thr Thr Cys Gly Asn Asp Trp Val Cys
                370                 375                 380

Glu His Arg Trp Arg Glu Ile Arg Asn Met Val Trp Phe Arg Asn Val
385                 390                 395                 400

Val Asp Gly Gln Pro Phe Ala Asn Trp Trp Asp Asn Gly Ser Asn Gln
                405                 410                 415

Val Ala Phe Gly Arg Gly Asn Arg Gly Phe Ile Val Phe Asn Asn Asp
                420                 425                 430

Asp Trp Gln Leu Ser Ser Thr Leu Gln Thr Gly Leu Pro Gly Gly Thr
                435                 440                 445

Tyr Cys Asp Val Ile Ser Gly Asp Lys Val Gly Asn Ser Cys Thr Gly
450                 455                 460

Ile Lys Val Tyr Val Ser Ser Asp Gly Thr Ala Gln Phe Ser Ile Ser
465                 470                 475                 480

Asn Ser Ala Glu Asp Pro Phe Ile Ala Ile His Ala Glu Ser Lys Leu
                485                 490                 495
```

<210> SEQ ID NO 33
<211> LENGTH: 419
<212> TYPE: PRT
<213> ORGANISM: Homo sapiens

<400> SEQUENCE: 33

```
Met Trp Gly Leu Leu Ile Phe Ser Val Leu Gly Gly Val Leu Ala
1               5                   10                  15

Lys Glu Asp Phe Val Gly His Gln Val Leu Arg Ile Ser Val Asp Asp
                20                  25                  30

Glu Ala Gln Val Gln Lys Val Lys Glu Leu Glu Asp Leu Glu His Leu
                35                  40                  45

Gln Leu Asp Phe Trp Arg Gly Pro Ala Arg Pro Gly Phe Pro Ile Asp
                50                  55                  60

Val Arg Val Pro Phe Pro Ser Ile Gln Ala Val Lys Val Phe Leu Glu
65                  70                  75                  80

Ala His Gly Ile Arg Tyr Thr Ile Met Ile Glu Asp Val Gln Leu Leu
                85                  90                  95
```

```
Leu Asp Glu Glu Gln Glu Gln Met Phe Ala Ser Gln Gly Arg Ala Arg
                100                 105                 110

Thr Thr Ser Thr Phe Asn Tyr Ala Thr Tyr His Thr Leu Glu Glu Ile
            115                 120                 125

Tyr Asp Phe Met Asp Ile Leu Val Ala Glu His Pro Gln Leu Val Ser
130                 135                 140

Lys Leu Gln Ile Gly Ser Ser Tyr Glu Gly Arg Pro Ile Tyr Val Leu
145                 150                 155                 160

Lys Phe Ser Thr Gly Gly Asn Asn Arg Pro Ala Ile Trp Ile Asp Thr
                165                 170                 175

Gly Ile His Ser Arg Glu Trp Val Thr Gln Ala Ser Gly Val Trp Phe
            180                 185                 190

Ala Lys Lys Ile Thr Glu Asp Tyr Gly Gln Asp Pro Ala Phe Thr Ala
        195                 200                 205

Ile Leu Asp Asn Leu Asp Ile Phe Leu Glu Ile Val Thr Asn Pro Asp
210                 215                 220

Gly Phe Ala Phe Thr His Ser Glu Asn Arg Met Trp Arg Lys Thr Arg
225                 230                 235                 240

Ser Arg Thr Ser Gly Ser Phe Cys Val Gly Val Asp Pro Asn Arg Asn
                245                 250                 255

Trp Asp Ala Gly Phe Gly Gly Ala Gly Ala Ser Ser Asn Pro Cys Ser
            260                 265                 270

Glu Thr Tyr His Gly Lys Phe Pro Asn Ser Glu Val Glu Val Lys Ser
        275                 280                 285

Ile Val Asp Phe Val Asn Asp His Gly Asn Ile Lys Ala Phe Ile Ser
290                 295                 300

Ile His Ser Tyr Ser Gln Leu Leu Leu Tyr Pro Tyr Gly Tyr Lys Thr
305                 310                 315                 320

Glu Ala Pro Ala Asp Lys Asp Glu Leu Asp Gln Ile Ser Lys Ser Ala
                325                 330                 335

Val Ala Ala Leu Thr Ser Leu Tyr Gly Thr Lys Phe Gln Tyr Gly Ser
            340                 345                 350

Ile Ile Thr Thr Ile Tyr Gln Ala Ser Gly Gly Thr Ile Asp Trp Thr
        355                 360                 365

Tyr Asn Gln Gly Ile Lys Tyr Ser Phe Ser Phe Glu Leu Arg Asp Thr
370                 375                 380

Gly Arg Tyr Gly Phe Leu Leu Pro Ala Ser Gln Ile Ile Pro Thr Ala
385                 390                 395                 400

Gln Glu Thr Trp Leu Ala Leu Leu Thr Ile Met Glu His Thr Leu Asn
                405                 410                 415

His Pro Tyr

<210> SEQ ID NO 34
<211> LENGTH: 266
<212> TYPE: PRT
<213> ORGANISM: Homo sapiens

<400> SEQUENCE: 34

Met Leu Arg Leu Leu Val Val Ala Ser Leu Val Leu Tyr Gly His Ser
1               5                   10                  15

Thr Gln Asp Phe Pro Glu Thr Asn Ala Arg Val Val Gly Gly Thr Glu
                20                  25                  30

Ala Gln Arg Asn Ser Trp Pro Ser Gln Ile Ser Leu Gln Tyr Arg Ser
            35                  40                  45
```

-continued

```
Gly Ser Ser Trp Ala His Thr Cys Gly Gly Thr Leu Ile Arg Gln Asn
    50                  55                  60

Trp Val Met Thr Ala Ala His Cys Val Asp Arg Glu Leu Thr Phe Arg
65                  70                  75                  80

Val Val Val Gly Glu His Asn Leu Asn Gln Asn Asp Gly Tyr Glu Gln
                85                  90                  95

Tyr Val Gly Val Gln Lys Ile Val Val His Pro Tyr Trp Asn Thr Asp
            100                 105                 110

Asp Val Ala Ala Gly Tyr Asp Ile Ala Leu Leu Arg Leu Ala Gln Ser
            115                 120                 125

Val Thr Leu Asn Ser Tyr Val Gln Leu Gly Val Leu Pro Arg Ala Gly
    130                 135                 140

Thr Ile Leu Ala Asn Asn Ser Pro Cys Tyr Ile Thr Gly Trp Gly Leu
145                 150                 155                 160

Thr Arg Thr Asn Gly Gln Leu Ala Gln Thr Leu Gln Gln Ala Tyr Leu
            165                 170                 175

Pro Thr Val Asp Tyr Ala Ile Cys Ser Ser Ser Tyr Trp Gly Ser
            180                 185                 190

Thr Val Lys Asn Ser Met Val Cys Ala Gly Gly Asp Gly Val Arg Ser
            195                 200                 205

Gly Cys Gln Gly Asp Ser Gly Gly Pro Leu His Cys Leu Val Asn Gly
    210                 215                 220

Gln Tyr Ala Val His Gly Val Thr Ser Phe Val Ser Arg Leu Gly Cys
225                 230                 235                 240

Asn Val Thr Arg Lys Pro Thr Val Phe Thr Arg Val Ser Ala Tyr Ile
            245                 250                 255

Ser Trp Ile Asn Asn Val Ile Ala Ser Asn
            260                 265
```

RP-HPLC METHOD FOR THE ANALYSIS AND QUANTIFICATION OF PANCREATIN ACTIVE PHARMACEUTICAL AGENTS

This patent application claims the benefit of provisional patent application No. 61/528,582 filed on Aug. 29, 2011.

FIELD OF THE INVENTION

Background of the Invention

Pancreatin is a mixture of several digestive enzymes produced by the exocrine cells of the pancreas. It is composed of amylase, lipase and protease. The pancreas gland produces both endocrine secretions that enter the blood stream and exocrine secretions that enter the duodenum. Whereas the endocrine secretions comprise hormones such as insulin and glucagon, the exocrine secretions to a large part are made up of enzymes necessary for digestion of food in the duodenum.

Without these enzymes (normally produced by the human pancreas), a substantial portion of undigested food simply passes through the digestive tract and provides no nutritional benefit. Pancreatin can be manufactured from the pancreas of either a pig or a cow. Porcine pancreatin juice is closest to that of humans, with high proportions of lipase and alpha-amylase in comparison with other mammals. Therefore, porcine pancreatin is made only from the pancreas of pigs, and is used to treat conditions in which pancreatic secretions are deficient, such as surgical pancreatectomy, pancreatitis and cystic fibrosis. Pancreatin has been claimed to help with food allergies, celiac disease, autoimmune disease, cancer and weight loss. Pancreatin is sometimes called "pancreatic acid", although it is neither a single chemical nor an acid.

Pancreatin enzyme products (PEPs) of porcine or bovine origin have been available in the United States for the treatment of exocrine pancreatic insufficiency (EPI) since before the enactment of the Federal Food, Drug, and Cosmetic Act of 1938 (the Act). With the exception of one PEP approved in 1996, PEPs have been marketed without New Drug Applications (NDAs) and were considered as dietary supplements. In recent years, however, the use of PEPs has been severely restricted in the US and Europe due to being derived from animal product, with a risk of viral transmission and bioactivity poorly characterized and standardized. The Food and Drug Administration (FDA) considers that an Over The Counter (OTC) monograph is not sufficient to adequately regulate these drug products and to standardize enzyme bioactivity, safety and effectiveness. The FDA's guidance for the industry requires all pharmaceutical companies marketing pancreatic enzymes for pancreatin deficiency to be approved under New Drug Applications. Since April 2010, PEPs are available by prescription only and only PEPs approved by the FDA remain on the market.

To be approved, an NDA must meet the requirements in 21 CFR §314.50 regarding chemistry, manufacturing and controls (CMC) information. The drug substance should be adequately characterized using chemical, physical and biological testing. Batch-to-batch consistency with respect to chemical identity, biological activity of different classes of enzymes including specific activity, and identity and purity levels should be demonstrated. Since Pancreatin is referenced in a new NDA, the agency expects the pancreatin Drug Master File (DMF) to meet current ICH Q6B requirements for specifications. Specifications for the drug substance should include tests for identity, biological activity of different classes of enzyme, purity and other relevant attributes. Because of the complexity of pancreatin extract product, it is unlikely that currently-available physiological and biological analytical tools would be able to demonstrate that the active ingredients in pancreatic extract products from two different batches/manufacturers are the same. Current United States Pharmacopeia (USP) monograph tests are insufficient to characterize the API to meet the ICH guideline. The new regulatory guidelines now require better methods to characterize pancreatin API.

SUMMARY OF THE INVENTION

In light of the foregoing, it is an object of the present invention to provide a method for the separation of proteins in a sample of pancreatin active pharmaceutical ingredient ("API"), the method comprising reverse phase-high performance liquid chromatography ("RP-HPLC"). In particular, proteins including trypsin, chymotrypsin, elastase, carboxypeptidase-B, phospholipase-A2, lipase, colipase, and amylase can be separated and identified using the methods of the invention. Separation of pancreatin proteins according to the methods can be achieved on, for example, a $C_4$ RP-HPLC column.

It is yet another object of the invention to provide a method for the separation and identification of proteins in a sample of pancreatin API, the method comprising separating proteins from a pancreatin API sample via RP-HPLC and identifying each protein by one or more methods of co-chromatography (spiking), sodium dodecyl sulfate polyacrylamide gel electrophoresis (SDS-PAGE), matrix-assisted laser desorption ionization-time of flight mass spectroscopy (MALDI-TOF-TOF MS) and Western Blotting. In accordance with the method, proteins including trypsin, chymotrypsin, elastase, carboxypeptidase-B, phospholipase-A2, lipase, colipase, and amylase can be separated and identified using the methods of the invention. Also in accordance with the method, separation of the pancreatin proteins can be achieved on, for example, a $C_4$ RP-HPLC column.

It is still another object of the invention to provide a method for the analysis of proteins in a sample of pancreatin API, the method comprising separating proteins from a pancreatin API sample via RP-HPLC; identifying each protein by one or more methods of co-chromatography (spiking), SDS-PAGE, MALDI-TOF-TOF MS and Western Blotting; and calculating amounts of each identified protein present in the sample of pancreatin. In accordance with the method, proteins including trypsin, chymotrypsin, elastase, carboxypeptidase-B, phospholipase-A2, lipase, colipase, and amylase can be separated and identified using the methods of the invention. Also in accordance with the method, separation of the pancreatin proteins can be achieved on, for example, a $C_4$ RP-HPLC column. Further in accordance with the method, calculation of amounts of each identified protein can be achieved using various software, such as, for example, Empower software.

Accordingly, it will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Other objects, features, benefits and advantages of the present invention will be apparent from this summary and the following descriptions of certain embodiments, and will be readily apparent to those skilled in the art. Such objects, features, benefits and advantages will be apparent from the above as taken into conjunction with the accompanying examples, data, and all reasonable inferences to be drawn therefrom.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is a table with relative amounts of various proteins in RP-HPLC peaks of pancreatin API sample 1.

FIG. 5 is a table with the molecular weights of pancreatin API proteins collected from RP-HPLC; *Relative abundance (%) of a protein band in a peak; "1208"=pancreatin API.

FIG. 9 is RP-HPLC analysis of spiked pancreatic API spiked with commercially-available standards of procine enzymes (spiking in red): a) $PLA_2$; b) trypsin; c) elastase; and d) amylase.

FIG. 10 is a table that identifies individual proteins by MS and Western Blotting detected by primary and secondary antibodies.

FIG. 11 is a Western Blot analysis of pancreatin peaks.

FIG. 28 Western Blot of pancreatin API-12.

FIG. 30 Western Blot of pancreatin API-14.

FIG. 31 Western Blot of pancreatin API-15.

FIG. 32 Western Blot of pancreatin API-17.

FIG. 33 Western Blot of pancreatin API-19.

FIG. 34 Western Blot of pancreatin API-21.

FIG. 36 Western Blot of pancreatin API-24.

DETAILED DESCRIPTION OF THE INVENTION

Reverse Phase-High Performance Liquid Chromatography

Figure 1:
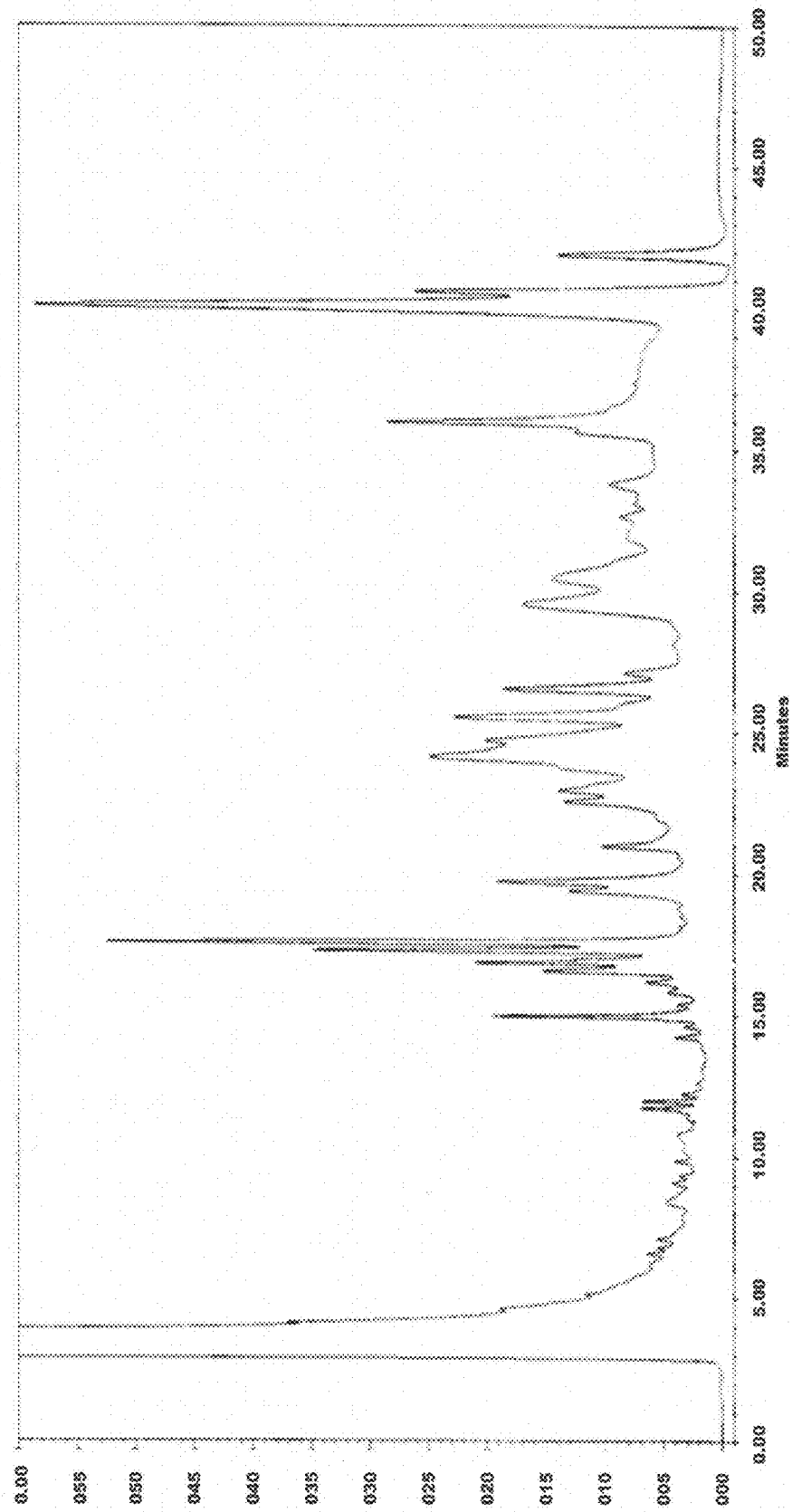
FIG. 1 is the RP-HPLC analysis of pancreatin API sample 1.

Accordingly, the present invention includes a RP-HPLC method to separate proteins in a pancreatin API sample. The method comprises treating a pancreatin sample with a solvent to afford a soluble protein sample; fractionating the soluble protein sample using reverse phase-high performance liquid chromatography (RP-HPLC); collecting each of the fractionated proteins individually; and characterizing each of the fractionated proteins using one or methods selected from the group consisting of co-chromatography, SDS-PAGE, Western Blotting and MALDI-TOF-MS. The RP-HPLC mode separates proteins based on their hydrophobic characteristics. Proteins bind to RP-HPLC columns in aqueous mobile phase and are eluted from the column by increasing the hydrophobicity of mobile phase. The stationary phase (resin) is made up of hydrophobic alkyl chains ($-CH_2-CH_2-CH_2-CH_3$). There are three common chain lengths: $C_4$, $C_8$, and $C_{18}$, but others exist. Proteins are large molecules and can have multiple hydrophobic moieties to interact with the column. The shorter chain length ($C_4$), therefore, is often more appropriate for protein separation.

Illustrating certain non-limiting aspects and embodiments of the invention, a $C_4$ column (Vydac 214MS54, 250×4.6 mm, 5 micron, or water BEH C4, 250×4.6 mm, 3.5 micron) is used for the separation of pancreatin API proteins. Pancreatin proteins are separated by running a linear-segmented gradient of acetonitrile containing 0.1% trifluoroacetic acid (TFA). The eluted proteins are detected at 280 nm. The relative amounts of individual peaks are quantified using Waters Empower software. Quantification is based on integrated peak area of protein peaks using a threshold set at 0.5-120, and peak width set at 20-100.

Generally, to identify the protein peaks in pancreatin API, known protein standard solutions are spiked into the pancreatin sample and chromatography procedures are performed under the same elution conditions.

Sample Preparation for RP-HPLC

Pancreatin API samples are prepared as described below in Example 1. The soluble fraction of pancreatin API after centrifugation is used for RP-HPLC analysis. Soluble and insoluble fractions of pancreatin API are analyzed by SDS-PAGE to examine the components in both fractions (see Example 2). The results show that more than 95% of pancreatin API proteins are solubilized in the method procedure, and the majority components of the insoluble proteins are likely truncated lipase and chymotrypsin-like proteases as identified by SDS-PAGE or Western blot.

To optimize separation of pancreatin proteins on RP-HPLC, different columns, $C_4$, $C_8$ and $C_{18}$, and various elution gradients are tested. The best resolution is obtained from a $C_4$ column using elution conditions described in Table 1.

TABLE 1

(Column: $C_4$; Temperature: 40° C.; Sample: 1-2 mg/mL in 0.1% TFA; Autosampler temperature: 10° C.;
Mobile phase:
Solvent A: 0.1% TFA in PureLab water
Solvent B: 0.1% TFA in Acetonitrile)
Elution Conditions:

| Time (min) | Flow (mL/min) | Solvent A (%) | Solvent B (%) |
|---|---|---|---|
| 0 | 1.0 | 85 | 15 |
| 14 | 1.0 | 65 | 35 |
| 28 | 1.0 | 60 | 40 |
| 37 | 1.0 | 50 | 50 |
| 37.5 | 1.2 | 10 | 91 |
| 38.0 | 1.2 | 10 | 90 |
| 39.0 | 1.0 | 85 | 15 |
| 50.0 | 1.0 | 85 | 15 |

Figure 2:
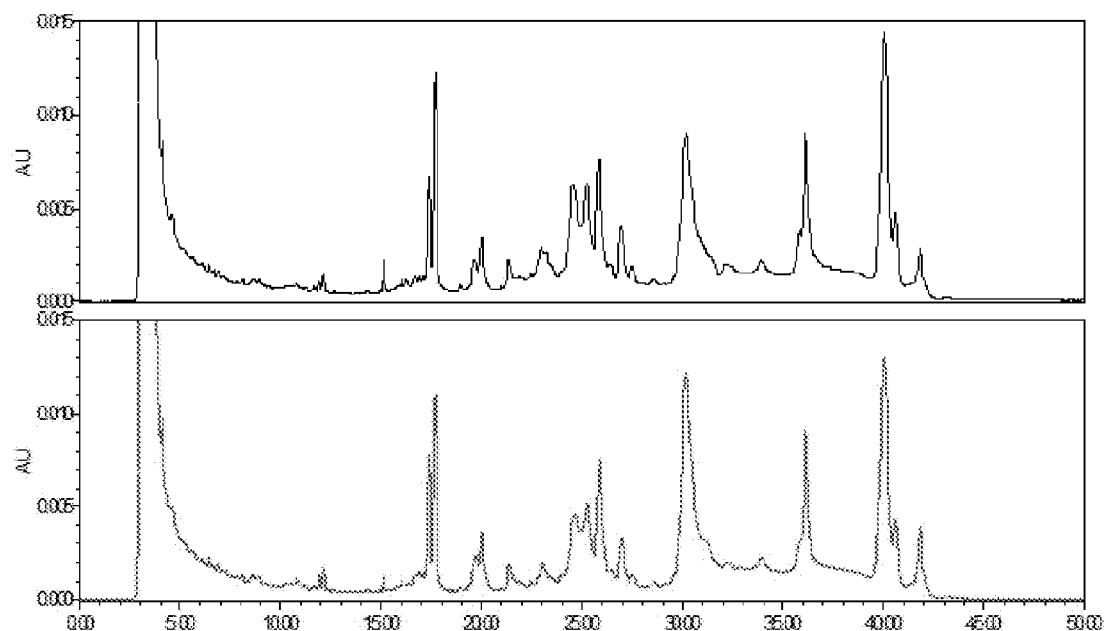
FIG. 2 is a protein profile of pancreatin API a) sample 1 and 2) sample 2.

The RP-HPLC analysis shows the major twenty five protein peaks present in pancreatin API sample 1 (FIG. 1; Injection: 100 µL of supernatant of pancreatin API; Column: $C_4$ (4.6×250 mm); Solvent A: 0.1% TFA in PureLab water; Solvent B: 0.1% TFA in acetonitrile; Elution method: method above detection: 280 nm). Similar HPLC profiles are obtained from two different batches (sample 1; SPL-1208-1257)(sample 2; SPL-1208-1211) of pancreatin API (FIG. 2; Loading: 100 µL of 1 mg/mL sample 1; Elution: developed method). The relative amounts of each protein can be calculated using an integration threshold of 10 to 120 and peak width of 25 to 100. The settings can be adjusted as needed until an appropriate baseline position of the peak is obtained. FIG. 3 lists the results calculated from three replicates using threshold of 10 and a peak width of 100 (Injection: 100 µL of 2 mg/mL sample 1; Calculation: Peak width=100, threshold=10; *Relative amount (%)=Individual peak area/total peak area×100). The maximum % RSD is less than 7% for all 25 peaks, indicating that the method is reproducible with precision.

Determination of Molecular Weights (MW)

Electrophoretic separations by SDS-PAGE are performed on peaks collected from RP-HPLC to determine the MW of the proteins. Sodium dodecyl sulfate (SDS) is an anionic detergent which denatures proteins and binds to proteins specifically in a mass ratio of 1.4:1. Therefore, the number of SDS molecules that bind to a protein is proportional to the number of amino acids of the protein. A reducing agent (Dithiothreitol, or "DTT") in the sample loading buffer cleaves disulfide bonds covalently linking other protein subunits. Under reducing and denaturing conditions, all proteins in the sample are resolved according to size (MW) during SDS-PAGE.

A linear relationship exists between the logarithm of the molecular weight of an SDS-denatured protein and its $R_f$. The $R_f$ is calculated as the ratio of the distance migrated by the molecule to that migrated by a marker dye-front. Determination of molecular weight (Mr) is achieved by plotting a standard curve of distance migrated vs. $\log_{10}$ MW for protein standards, and read off the log Mr of the protein to be identified after measuring distance migrated on the same gel. Quantification of proteins is based on integrated optical density of a band. The Kodak 1D 3.6 software is designed based on this principle and is used for this data analysis.

Different SDS-polyacrylamide gels and different running buffers are tested for separation. The following combinations of gel and running buffer are evaluated: 4-20% Tris-glycine gel with Tris-glycine buffer; 10% Bis-Tris NuPAGE with MOPS buffer; 12% Bis-Tris NuPAGE with MOPS buffer; 4-12% Bis-Tris NuPAGE with MOPS buffer; and 4-12% Bis-Tris NuPAGE with MES buffer. The best separation for pancreatin API proteins is obtained with 4-12% Bis-Tris NuPAGE using MES buffer (see Example 4 below).

Figure 4:
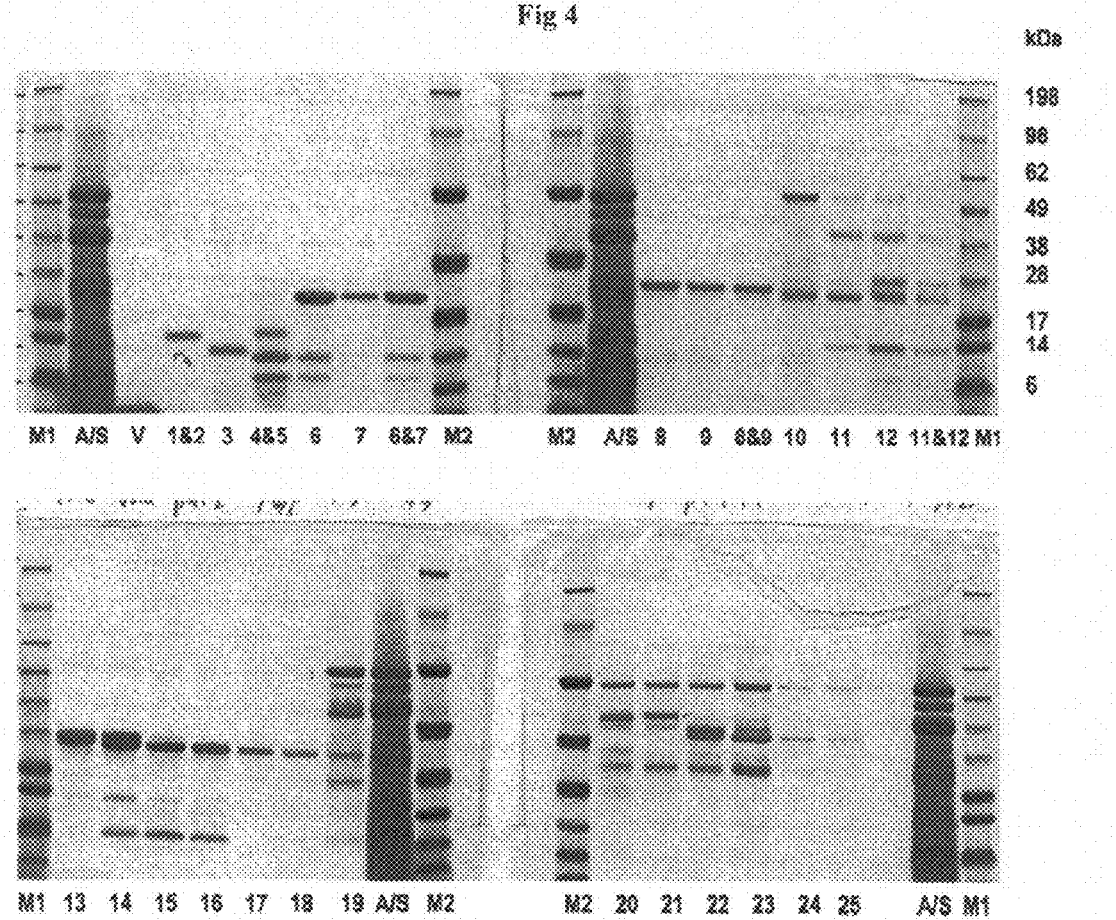
FIG. 4 depicts the molecular weights of RP-HPLC pancreatin API protein peak fractions (4-12% SDS-PAGE). M1: SeeBlue plus protein marker; M2: MultiMark; A/S: Appliend sample for HPLC; V: Void; 1-25: HPLC pancreatin API Fraction #1-25.

Determination of molecular weight (MW) is done by SDS-PAGE. The molecular weights of the HPLC-pancreatin API peak fractions (the fractions numbers match the elution profile in FIG. 2) are presented in FIG. 4 and FIG. 5 (see also Example 4). Void fraction collected from the largest peak in pancreatin API-HPLC chromatograms contains only small fragments (less than 3 kDa) with relatively small quantities.

Western Blotting

Western blot analysis is used to characterize pancreatin proteins. Because of the ability of antibody molecules to recognize and bind to antigen very specifically, this antibody-binding specificity can be used to identify proteins. Proteins across different species with similar functions may share sequence homology. Therefore, antibodies against the protein in one species could also react with the protein in other species with similar function.

In a typical Western blot analysis, pancreatin API proteins are separated on a denaturing SDS polyacrylamide gel and are transferred (blotted) to a nitrocellulose membrane. The membrane is then exposed sequentially to solutions containing primary antibody, followed by a secondary antibody coupled to an enzyme. The membrane is then soaked in a substrate solution to develop a colored reaction, which results in identifying the antigen as a band.

Experiments are carried out using a Novagen HIS-Tag AP Western Kit. Primary antibodies used in this study are listed in Table 2. Immunoreactive proteins are detected using Alkaline Phosphatase (AP)-conjugated goat anti-mouse or anti-rabbit immunoglobulin (Promega, Madison, Wis.). All antibodies are diluted to the appropriate level in blocking solution.

TABLE 2

| Antibody | Source | Immunogen | Vender, Cat. # | Dilution |
|---|---|---|---|---|
| Anti-PLA$_2$ | Rabbit | Porcine pancreatic phospholipase A$_2$ | Upstate Cat. #06-150 | 1:500 |
| Anti-Carboxypeptidase B | Rabbit | Porcine pancreatic Carboxypeptidase B | Biogenesis Cat. #1810-0130 | 1:4000 |
| Anti-Trypsin | Rabbit | Human pancreatic Trypsin | Fitzgerald Cat. #70-XR77 | 1:1000 |
| Anti-Chrymotrypsin | Rabbit | Human pancreatic Chymotrypsin | Fitzgerald Cat. #20-CR79 | 1:1000 |
| Anti-Amylase | Rabbit | Human pancreatic amylase | Fitzgerald Cat. #20-AR07 | 1:3000 |
| Anti-Lipase | Rabbit | Human pancreatic lipase | Fitzgerald Cat. #10-L50 | 1:100 |
| Anti-Elastase | Rabbit | Human pancreatic | Fitzgerald Cat. #20-ER66 | 1:500 |

MALDI-TOF-TOF Mass Spectrometry

Matrix-assisted laser desorption ionization-time of flight mass spectrometry (MALDI-TOF-TOF MS) techniques are utilized to identify proteins in pancreatin API. MALDI-TOF mass spectrometry is a relatively novel tool for protein characterization. The technique is based upon an ultraviolet absorbing matrix. The matrix and biomolecules (peptide fragments generated using amino-acid specific proteolytic enzyme, for example) are mixed at a molecular level in an appropriate solvent with a ~104-fold molar excess of the matrix. The solvent prevents aggregation of the polymer. The sample/matrix mixture is placed onto a sample probe tip. The solvent is then removed, leaving co-crystallized biomolecules homogeneously dispersed within matrix molecules. When the pulsed laser beam is tuned to the appropriate frequency, the energy is transferred to the matrix causing desorption and ionization of the biomolecules. The ionized biomolecules are accelerated in an electric field and enter the flight tube where they are then separated in time and reach the detector. An analyzer measures the time-of-flight (TOF). The flight time of an ion is related to its mass-to-charge ratio. In this way, each molecule yields a distinct signal; thus, mass spectra can be generated. The masses of the peptides are obtained from mass spectrometry. Proteins are identified by matching the observed sequences of the peptides to NCBI proteins database (3,794,285 sequences in the database, see Example 5). The pancreatin API protein samples are prepared and sent out for MS analysis at the Mass Spectrometry Facility (Biotechnology Center, University of Wisconsin-Madison).

Quantitation of Trypsin in Pancreatin API

Due to the availability of high-purity commercial standards, the trypsin in pancreatin API samples can be quantitated using an external standard.

Figure 6:
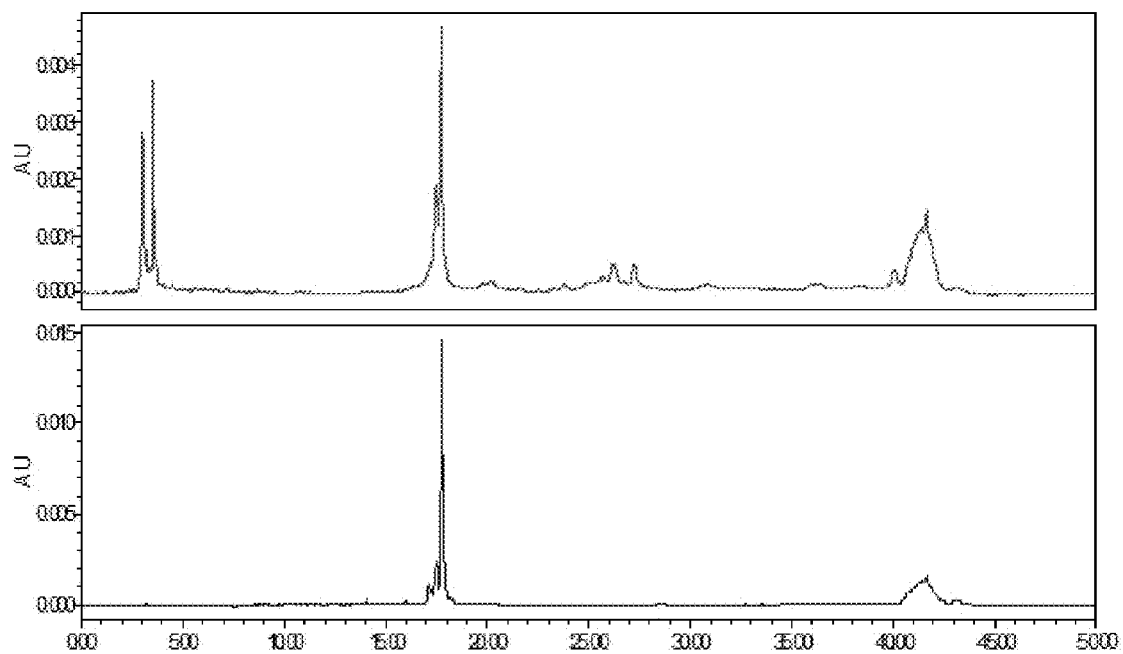
FIG. 6 is the RP-HPLC analysis of trypsin standard.

To select a good external standard, porcine trypsin is purchased from Sigma and US Biological (USB). The standards are dissolved in HPLC solvent A and analyzed by RP-HPLC. Trypsin from Sigma has a higher purity than that of USB (FIG. 6). The Sigma product (Cat. # T0303) contains 3 major peaks of trypsin (retention times 17 to 18 min). The chromatograms also contain a broad peak at 41.5 minutes due to gradient wash and re-equilibration. The USB trypsin (Cat. #22715) contains two major peaks of trypsin (retention time between 17 and 18 min) and several other large peaks. Because of its higher purity, Sigma trypsin is used for quantification of trypsin in SPL API samples.

Figure 7:
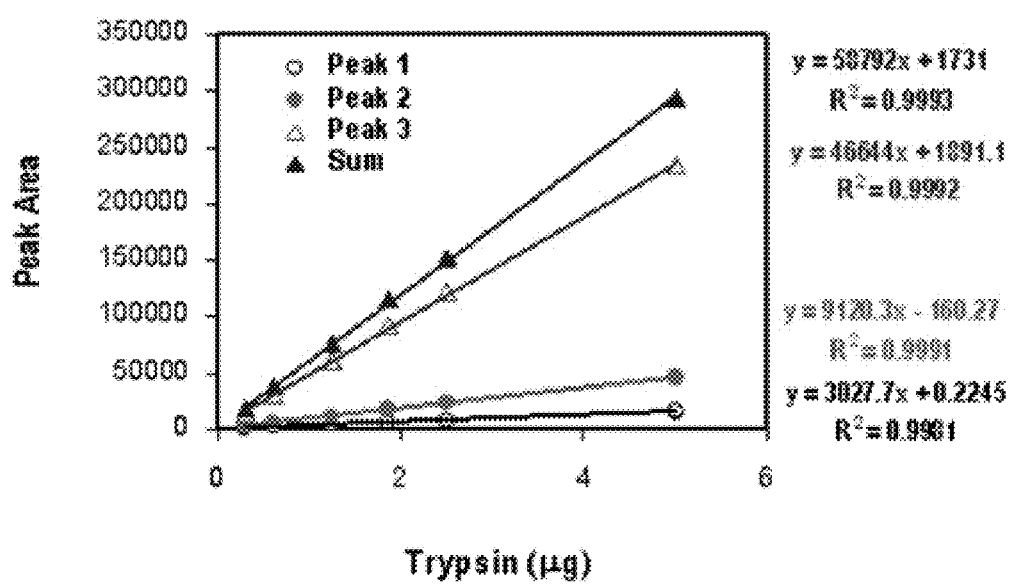
FIG. 7 depicts standard curves generated using Sigma trypsin.

Standard curves are generated using Sigma trypsin. Serial dilutions of trypsin standards, 0.0625, 0.125, 0.25, 0.5, 0.75 1.0 and 2.0 mg/mL are prepared and analyzed by RP-HPLC. Two injections are performed for each concentration and are averaged. Data is calculated for linearity between peak area and trypsin amount (each of the three peaks and their sums). The linear range of the standard curve for trypsin is 0.156 to 5.0 µg. In this range, $R^2$ values of 0.9982 to 0.9989 are obtained (Table 3 and FIG. 7).

TABLE 3

RP-HPLC Analysis of Trypsin Standard

| Trypsin | Peak Area | | | |
|---|---|---|---|---|
| (µg) | Peak 1 | Peak 2 | Peak 3 | Sum |
| 0.3125 | 808 | 2488 | 13855 | 17151 |
| 0.3125 | 846 | 2630 | 14736 | 18212 |
| 0.625 | 1765 | 5438 | 29741 | 36944 |
| 0.625 | 1741 | 5144 | 29598 | 36483 |
| 1.25 | 3739 | 11147 | 61024 | 75910 |
| 1.25 | 3674 | 11360 | 60570 | 75604 |
| 1.875 | 6080 | 17615 | 91933 | 115628 |
| 1.875 | 6010 | 16723 | 91808 | 114541 |
| 2.5 | 7514 | 22891 | 120092 | 150497 |
| 2.5 | 7877 | 23140 | 121756 | 152773 |
| 5 | 14925 | 44476 | 233429 | 292830 |
| 5 | 15040 | 45932 | 232793 | 293765 |

Using the standard curve, the amounts of trypsin are quantified in pancreatin API, sample 1 and sample 2. As seen in Table 4, similar levels of trypsin are detected in these two different lots of SPL API-1208. The % RSD values of trypsin concentration from three injections of 1208-1257 ranged from 0.4 to 11.9% for three separated trypsin peaks. The % RSD value was much lower (0.5%) when all three peak areas were summed.

TABLE 4

| Trypsin | Peak Area | | | |
|---|---|---|---|---|
| (µg) | Peak 1 | Peak 2 | Peak 3 | Sum |
| 0.3125 | 808 | 2488 | 13855 | 17151 |
| 0.3125 | 846 | 2630 | 14736 | 18212 |
| 0.625 | 1765 | 5438 | 29741 | 36944 |
| 0.625 | 1741 | 5144 | 29598 | 36483 |
| 1.25 | 3739 | 11147 | 61024 | 75910 |
| 1.25 | 3674 | 11360 | 60570 | 75604 |
| 1.875 | 6080 | 17615 | 91933 | 115628 |
| 1.875 | 6010 | 16723 | 91808 | 114541 |
| 2.5 | 7514 | 22891 | 120092 | 150497 |
| 2.5 | 7877 | 23140 | 121756 | 152773 |
| 5 | 14925 | 44476 | 233429 | 292830 |
| 5 | 15040 | 45932 | 232793 | 293765 |

Identification of Individual Proteins

The RP-HPLC peak fractions of pancreatin API sample 1 are manually collected and lyophilized. The dried protein fractions are dissolved in 1× lithium dodecylsulfate (LDS) sample buffer containing 50 mM dithiothreitol (DTT). Proteins are identified using the methods of co-chromatography (spiking), SDS-PAGE, Western Blotting and MALDI-TOF-MS.

Co-Chromatography (Spiking Studies)

Porcine pancreatic enzymes, trypsin, elastase, carboxypeptidase-B (CPB), carboxypeptidase-A (CPA), phospholipase-A2 ($PLA_2$), lipase, colipase, and amylase are commercially available. The purities of trypsin, elastase, $PLA_2$ and amylase are high enough for spiking; the others are further purified.

Figure 8:
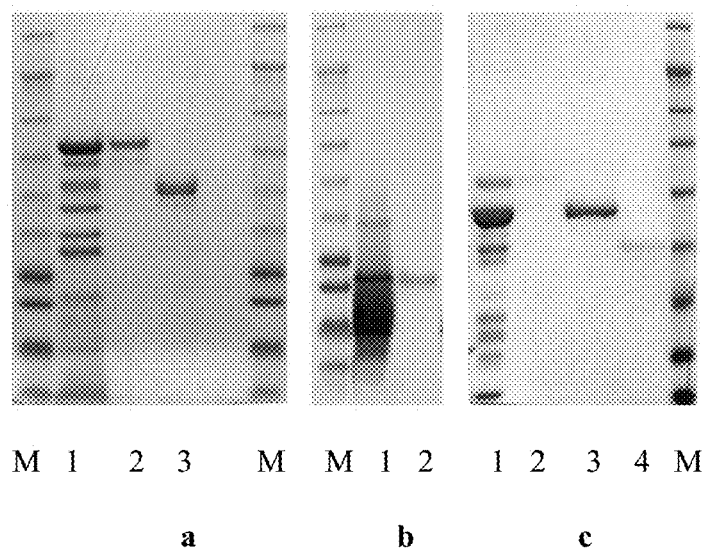
FIG. 8 is an SDS-PAGE analysis of purified porcine pancreatic a) lipase; b) colipase; and c) carboxypeptidase-B, wherein lane 1 represents unpurified enzyme and lanes 2-4 represent purified enzymes.

Purification of Standard Pancreatic Proteins: Lipase, Colipase and Carboxypeptidase-B by SDS-PAGE Porcine pancreatic enzymes, lipase (USP, Cat. #1494079, Lot # I1E327), colipase (Boehringer Mannhein) and carboxypeptidase-B (Sigma, Cat. # C9584, Lot #108H74061) are purchased. After separation on SDS-PAGE under reducing conditions, proteins are revealed by SimplyBlue SafeStain (Invitrogen, Cat. # LC6060). Protein bands of interest are excised and eluted with 100 mM sodium acetate (NaOAc) containing 0.1% SDS and 10 mM DTT, pH 7.8. Eluted proteins are dialyzed overnight at 4° C. against 100 mM NaOAc buffer, pH 7.8 to remove SDS. The SDS-PAGE analysis (FIG. 8) of the purified pancreatic enzymes shows a purity of greater than 95% for all three enzymes.

The pancreatin API samples are spiked with commercially-available standards of porcine enzymes: trypsin, elastase, $PLA_2$ and amylase. The results show that $PLA_2$ co-eluted with RP-HPLC peaks 1&2, trypsin co-eluted with peaks 4-7, elastase co-eluted with peak 15 and amylase co-eluted with peak 19 (see FIG. 9).

The purified lipase, colipase and CPB are also analyzed by RP-HPLC. When spiking the purified enzymes into pancreatin API proteins, the results are inconclusive because a significant degradation of pancreatin API proteins occurs at pH 6.0 (the higher pH is the result of mixing purified enzyme and pancreatin API protein sample).

Protein Identification by Western Blotting

Western Blotting or immunoblotting procedures combine the resolution of gel electrophoresis with the specificity of antibody detection. An antibody locks on to a specific protein even when surrounded by others proteins. This method is used to determine the presence and the molecular weights of proteins in pancreatin API samples.

The primary and secondary antibodies used in this study are listed in FIG. 10. The RP-HPLC separated pancreatin API proteins that react with these antibodies are summarized in FIG. 10. (See Example 5).

Protein Identification by MALDI-TOF-TOF Mass Spectrometry

Matrix Assisted Laser Desorption Ionization Time-of-flight-Time-of-flight (MALDI-TOF-TOF) Mass Spectrometry (MS) is used to determine both the accurate peptide mass and peptide sequences of pancreatin API proteins.

Trypsin, chymotrypsin, elastase (three types: elastase, elastase-I and elastase-II), carboxypeptidase (two types: carboxypeptidase-A and carboxypeptidase-B), phospholipase-$A_2$, lipase, colipase, and amylase are identified in a pancreatin API sample (FIG. 10). In addition, porcine pancreatic lithostathine (an inhibitor of calcium carbonate crystals and bacterial aggregation in the pancreas) is also identified (see Example 5).

The MS results generated from peak 13 did not match any sequences in the database, but immunoblot analysis showed that it reacted specifically with human anti-chymotrypsin antibody (FIG. 11). This suggests that this protein is a member of the chymotrypsin family, like elastase, trypsin and kallikrein. No known porcine chymotrypsin peptide sequences are found in sequence databases.

In summary, all proteins revealed in the RP-HPLC elution profile of pancreatin API are identified by methods of co-chromatography (HPLC spiking), Western blotting, or MS. No unexpected proteins are detected. Some proteins existed in different sizes (full length or truncated) and isoforms.

EXAMPLES

Example 1

RP-HPLC

Separation and identification of panreatin API proteins. Quantification of Trypsin in pancreatin APIs using an external Trypsin standard.

Materials and Equipment:
1) Porcine Trypsin: Sigma, Cat. # T0303;
2) Pancreatin API samples
3) Trifluoroacetic acid (TFA): Pierce, Cat. #28904;
4) PureLab water;
5) Acetonitrile: J. T. Baker, Cat. #9829, or equivalent;
6) 50 mL Sterile centrifuge tubes: Fisher, Cat. #06-443-18;
7) 15 mL Sterile centrifuge tubes: Corning, Cat. #430766;
8) 1.5 mL Eppendorf tubes;
9) $C_4$ column: Vydac, Cat. #214MS54, 250×4.6 mm, 5 micron;
10) Waters Alliance HPLC 2695 System with 2487 UV detector;
11) Eppendorf centrifuge: CENT-7000005

Mobile Phase:
Solvent A (0.1% TFA in $H_2O$): add 1 mL TFA to 1 L PureLab water;
Solvent B (0.1% TFA in acetonitrile): add 1 mL TFA to 1 L acetonitrile.

Preparation of Protein Samples:

Pancreatin API protein samples: 1 mg/mL. Weigh 30 mg of pancreatin API powder is put into a 50-mL centrifuge tube. 30 mL of Solvent A is subsequently added to the tube, and proteins are extracted by shaking on a rocker shaker (AI-7000008, set speed at 4) at room temperature for 30 minutes. An aliquot of the solution (1 mL) is transferred into a microcentrifuge tube and centrifuged at 13,000 rpm for 10 minutes. The supernatant (800 μL) is carefully removed and used for analysis.

Trypsin Standard Solutions. 10±0.1 mg of Sigma Trypsin is dissolved in 5 mL of Solvent A. The resulting solution is centrifuged at 13,000 rpm in an Eppendorf centrifuge for 5 minutes, resulting in a standard solution of 2 mg/mL. Table 5 shows the standard dilutions of Trypsin prepared using this stock solution (2.5 μL of each standard injected for RP-HPLC analysis).

TABLE 5

| Tube # | Volume of Solvent A (mL) | Volume and source of Trypsin (mL) | Final Trypsin Concentration (μg/mL) |
|---|---|---|---|
| 1 | 0 | 2 mL of Std (2 mg/mL) | 2000 |
| 2 | 0 | 1.0 mL of tube 1 + 1 mL of tube 3 | 1500 |
| 3 | 1.0 | 1.0 mL of tube 1 dilution | 1000 |
| 4 | 0 | 1.0 mL of tube 3 + 1 mL of tube 5 | 750 |

TABLE 5-continued

| Tube # | Volume of Solvent A (mL) | Volume and source of Trypsin (mL) | Final Trypsin Concentration (μg/mL) |
|---|---|---|---|
| 5 | 1.0 | 1.0 mL of tube 3 dilution | 500 |
| 6 | 1.0 | 1.0 mL of tube 4 dilution | 250 |
| 7 | 1.0 | 1.0 mL of tube 5 dilution | 125 |
| 8 | 1.0 | 1.0 mL of tube 6 dilution | 62.5 |

RP-HPLC Procedure:

The RP-HPLC method is equilibrated and samples are used with the method (See Table 1 above).

Trypsin peak area of the two major peaks are integrated from each standard run using appropriate settings of threshold and peak width (adjust settings until appropriate baseline positions of the peaks are obtained). Sum the area of two peaks.

The standard curves of the sum of peak area vs. Trypsin amount (μg) are plotted. Printed best-fit equations and values of $R^2$ generated.

$$Y = mX + b;$$

Y: Peak area; X: amount of Trypsin (μg).

After the amount of Trypsin, X, is measured, the average Trypsin peak area of replicates is measured. The Trypsin amount is then determined using the equation of standard curves. Calculation of Trypsin Concentration: mg/g dry weight.

$$Trypsin = Y - b/m \times 10^*$$

*Conversion factor=1/100 μL (injection)×1000 μL (sample)

Example 2

Development of RP-HPLC Method

Comparison of Elution Conditions for Pancreatin API Separation:

Methods: developed method (Table 1, above); Göke (Table 6); and modified Göke (Table 7).

TABLE 6

| Time (min) | Flow (ml/min) | Solvent A (%) | Solvent B (%) |
|---|---|---|---|
| 0 | 1.0 | 100 | 0 |
| 3 | 1.0 | 67 | 33 |
| 5 | 1.0 | 67 | 33 |
| 17 | 1.0 | 61 | 39 |
| 30 | 1.0 | 60 | 40 |
| 35 | 1.0 | 58 | 42 |
| 36 | 1.0 | 54 | 46 |
| 42 | 1.0 | 52 | 48 |
| 45 | 1.0 | 52 | 48 |
| 50 | 1.0 | 45 | 55 |
| 52 | 1.0 | 45 | 55 |
| 60 | 1.0 | 27 | 73 |
| 61 | 1.0 | 27 | 73 |
| 62 | 1.0 | 100 | 0 |
| 65 | 1.0 | 100 | 0 |

TABLE 7

| Time (min) | Flow (ml/min) | Solvent A (%) | Solvent B (%) |
|---|---|---|---|
| 0 | 1.0 | 0 | 100 |
| 3 | 1.0 | 85 | 15 |
| 15 | 1.0 | 67 | 33 |
| 17 | 1.0 | 61 | 39 |
| 30 | 1.0 | 50 | 50 |
| 35 | 1.0 | 50 | 50 |
| 36 | 1.0 | 10 | 90 |
| 39 | 1.0 | 10 | 90 |
| 40 | 1.0 | 100 | 0 |
| 50 | 1.0 | 100 | 0 |

Figure 12:
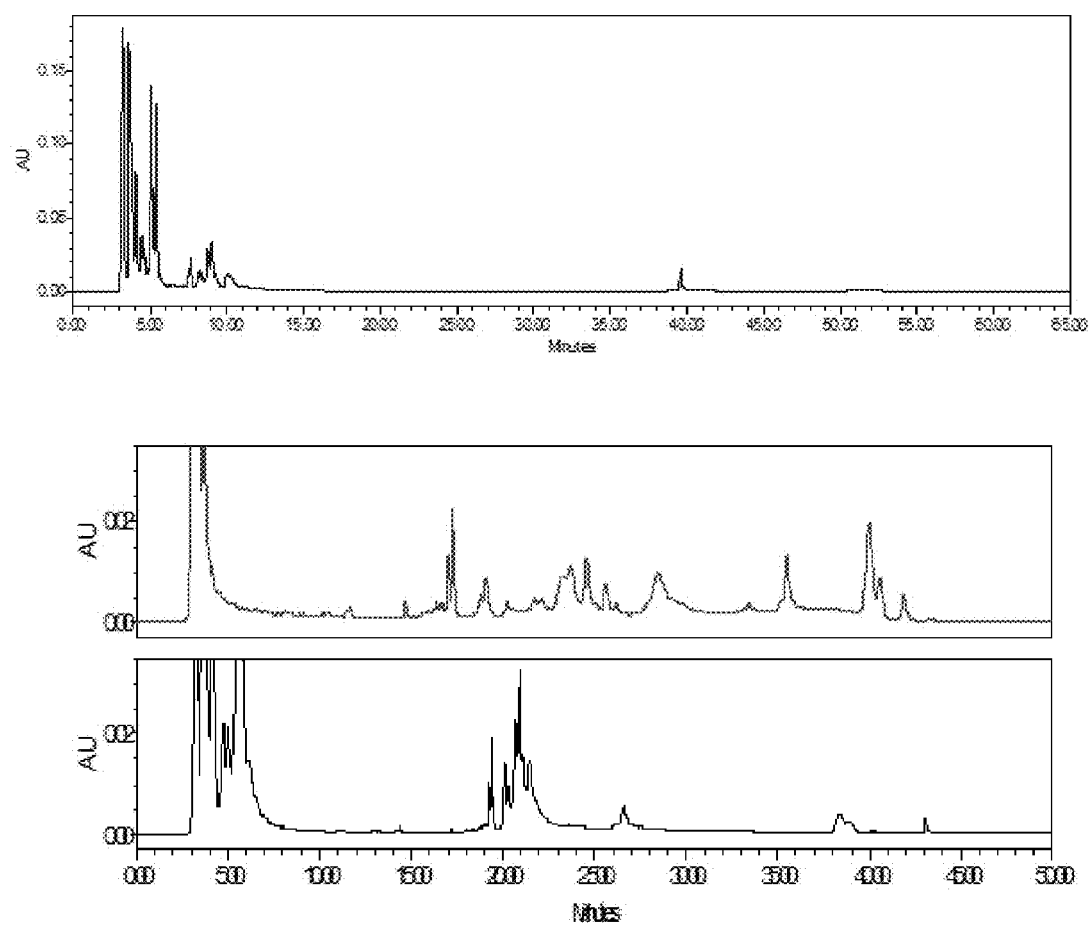
FIG. 12 is the result of the development of an RP-HPLC method: a) Göke; b) developed method; and c) modified Göke.

The results of the three methods are depicted in FIG. 12. The best separation is obtained using the developed method.

Example 3

SDS-PAGE Analysis

The SDS-PAGE procedures were used for: 1) analysis of proteins in 1208 samples; 2) purification of target proteins; 3) quantification of proteins; 4) determination of the molecular weight of RP-HPLC fractions;

5) determination of the purity of protein preparations; 6) Western Blotting; and 7) in-gel digestion of proteins for MS.

Materials:

Novex NuPAGE® 4-12% Bis-Tris mini-gels #NP0321 (Invitrogen.)

Novex NuPAGE 12% Bis-Tris #NP 0341 (Invitrogen)

Novex 4-12% Tris Glycine #EC60252 (Invitrogen)

Novex NuPAGE® antioxidant, 15 mL #NP0005 (Invitrogen)

Novex NuPAGE® MES running buffer (20×) #NP0002 (Invitrogen)

Novex NuPAGE® MOPS running buffer (20×) #NP0001 (Invitrogen)

Novex TrisGlycine running buffer (20×) #LC2675 (Invitrogen)

Novex NuPAGE® LDS sample buffer (4×) #NP0007 (Invitrogen)

Novex NuPAGE® Transfer buffer (20×) #NP0006 (Invitrogen

SeeBlue Plus MW standard #LC5925 (Invitrogen)

Novex Simple Blue Safe Stain #LC6060 (Invitrogen)

Dithiothreitol (DTT), 99%, ACS reagent #45,777-9 (Aldrich Chemical Co.)

Buffer Preparation:

a) MES SDS (1×) Running Buffer—40 mL of Novex NuPAGE® MES SDS buffer concentrate (20×) is diluted to 800 mL with PureLab water in a 1-liter graduated mixing cylinder. The cylinder is sealed with a stopper and slowly inverted five times to mix (minimize foaming).

B) MESS DS (1×) Running Buffer Plus Antioxidant—200 mL of MES SDS (1×) running buffer (see above) is transferred to a 250-mL Erlenmeyer flask. 0.5 mL of Novex NuPAGE® antioxidant is added and the flask is swirled gently to mix.

Sample Loading Buffer (2×):

Prepared fresh on the day of use. For 1 mL of loading buffer, the following components are combined in a microcentrifuge tube: 500 µL Novex NuPAGE® LDS (4×) sample buffer, 200 µL DTT solution (0.5 M), and 300 µL PureLab water. If a larger amount is required, volumes are scaled accordingly. 0.5 M DTT is prepared by dissolving 0.386 g (2.5 mmoles) dithiothreitol in 5.0 mL of PureLab water. 0.5-mL aliquots are stored frozen in microcentrifuge tubes for future use.

Sample Loading Buffer (1×):

For a 1 mL: 250 µL Novex NuPAGE® LDS (4×) sample buffer; 100 µL 0.5 M DTT solution; 650 µL PureLab water.

Sample Preparation:

A) Pancreatin API—Soluble and insoluble pancreatin API protein samples are prepared as follows: 50-60 mg of pancreatin API powder are weighed out and put into a 50-mL tube. 0.1% TFA in PureLab water (Mobile Phase A) is added to make a solution of 2 mg/mL. The tube is sealed and the sample is shaken on a rocker shaker (AI-7000008, speed at 4) at room temperature for 30 minutes. 1 mL of the solution is transferred into a centrifuge tube and centrifuged at 13,000 rpm for 10 minutes. 100 µL of supernatant is carefully removed to a fresh centrifuge tube and 100 µL of 2× sample loading buffer (sample defined as soluble proteins) is added. The rest of the supernatant is removed, 1.0 mL of 0.1% TFA is added, mixed, and centrifugation is repeated one more time. All supernatant is then remove and discarded. The pellet is resuspended with 1 mL of 1× sample loading buffer (sample defined as insoluble protein). All samples are heated at 70±2° C. for 10 minutes in a heating block.

B) Dried HPLC Fraction—The dried HPLC fraction is resuspended with 1× of sample loading buffer (20 µL/mL of collected volume prior to drying) and transferred to a fresh microcentrifuge tube. The tubes are sealed and heated at 70±2° C. for 10 minutes in a heating block.

Running SDS-PAGE:

After heating, samples are spin loaded at 13,000 rpm briefly (30 seconds) and 10 µL (1208 mix) or 20 µL (HPLC fractions or purified protein) is loaded on 4-12% Bis-Tris NuPAGE gel. The upper chamber is filled in Novex XCell SureLock® mini-cell with 200 mL of "SDS Running Buffer (1×) Plus Antioxidant," and the lower chamber is filled with 600 mL of 1× running buffer. The gel(s) is run at 150 V for 1 hour.

Figure 13:
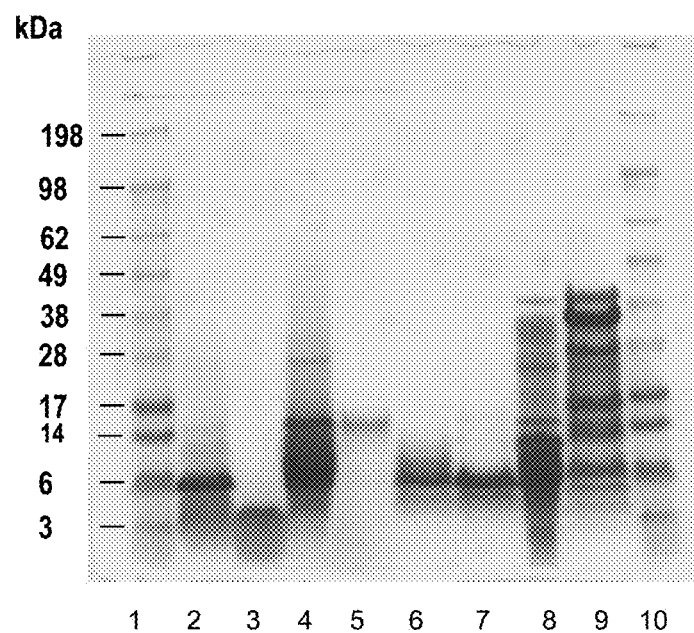
FIG. 13 depicts the optimum running conditions for SDS-PAGE. 4-12% Bis-Tris NuPAGE of colipase and carboxypeptidase B; running conditions: reduced, 1×MES running buffer and 150 V for 55 minutes.
Figure 14:
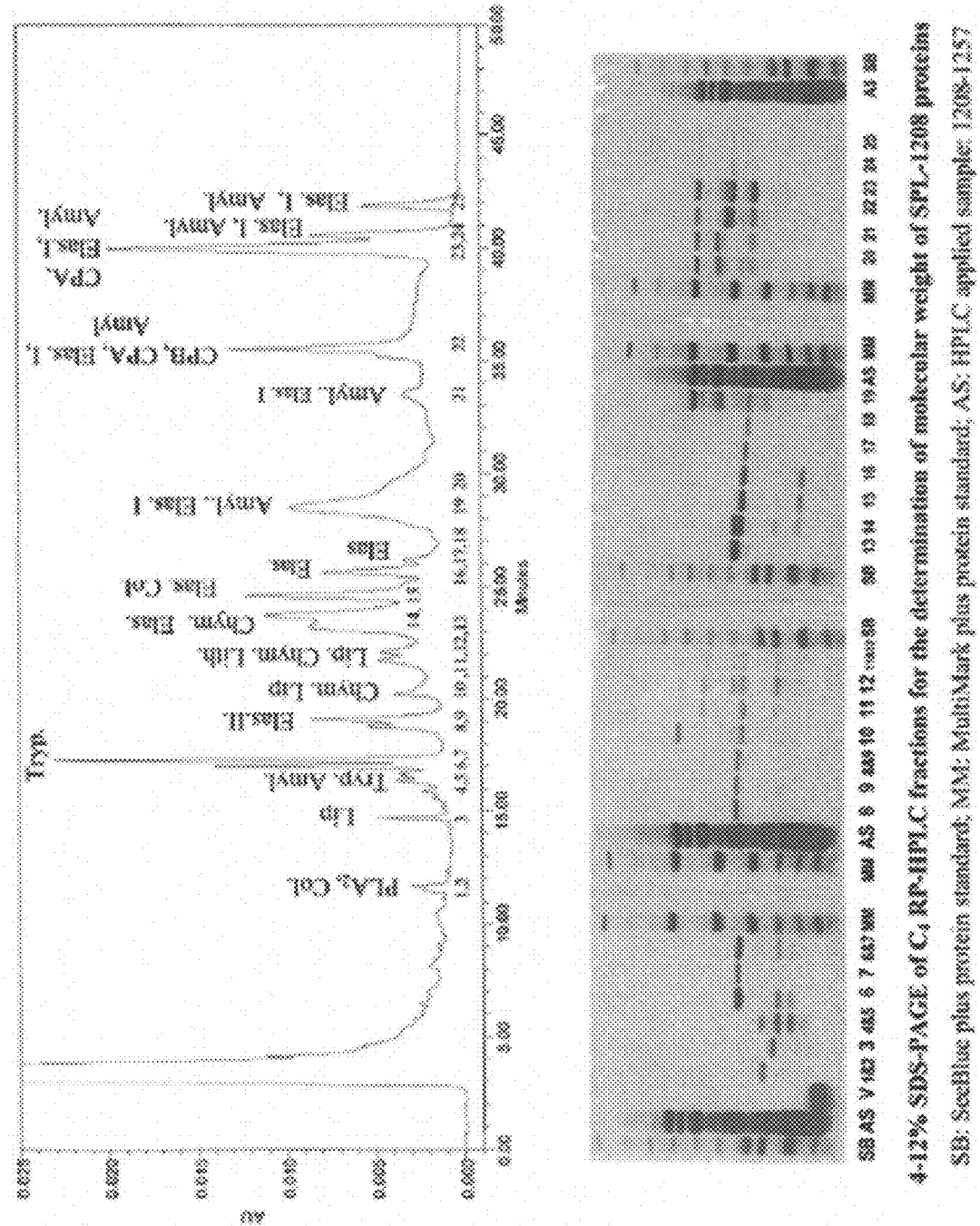
FIG. 14 depicts SDS-PAGE analysis of HPLC-separated fractions for the determination of molecular weight of pancreatin API proteins (4-12% SDS-PAGE of $C_4$ RP-HPLC fractions); SB: SeeBlue plus protein standard; MM: Multi-Mark plus protein standard; AS: HPLC applied sample: sample 1.

The optimum running conditions for SDS-PAGE is depicted in FIG. 13. 4-12% Bis-Tris with MES buffer is chosen for separation of pancreatin API proteins. SDS-PAGE analysis of HPLC-separated fractions for the determination of molecular weight of pancreatin API proteins is depicted in FIG. 14 (4-12% SDS-PAGE of $C_4$ RP-HPLC fractions).

To check if pancreatin proteins are well solubulized in 0.1% TFA for HPLC analysis, fractions of solubilized and insolubilized proteins are prepared as follows in Scheme A:

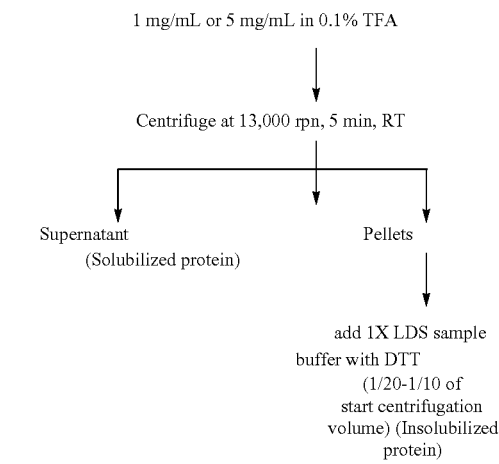

Figure 15:
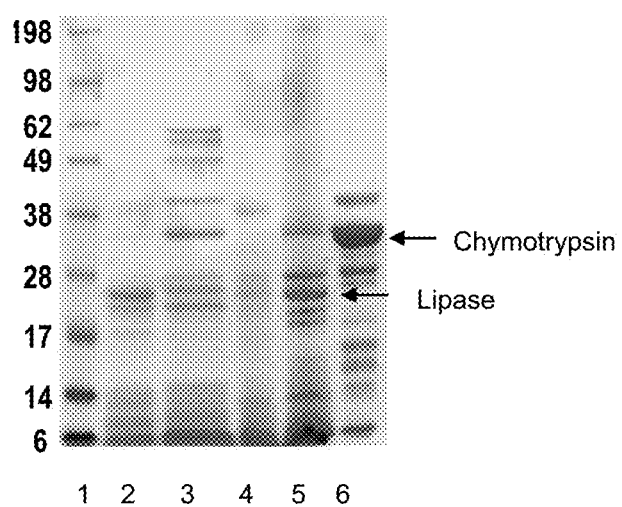
FIG. 15 is a 4-12% Bis-Tris NuPAGE showing solubilized and unsolubilized proteins from sample 1. Lanes—1: See-Blue Plus protein Marker; 2 & 3: 20 µL soluble proteins of 1 mg/mL and 5 mg/mL solution, respectively; 4 & 5: 200 µL of unsolublized proteins of 1 mg/mL and 100 µL of 5 mg/mL solution, respectively; 6: Standard Bovine Chymotrypsin.

4-12% Bis-Tris NuPAGE shows solubilized and unsolubilized proteins from sample 1 (FIG. 15). Protein bands of Chymotrypsin are identified by analyzing the samples side-by-side with the standards. The Lipase band is identified by Western blotting.

Density analysis of the scanned SDS-PAGE image indicates that 97% of pancreatin proteins are solubilized when samples are prepared at 1 mg/mL. The amount of solubilized protein is slightly decreased to 90% in samples of 5 mg/mL. Therefore, preparation of samples at 1 mg/mL for HPLC analysis is preferred.

The fraction of unsolubilized protein contains mainly chymotrypsin and truncated lipases, which are also well represented in the fraction of solubilized protein, as detected by RP-HPLC.

Example 4

Western Blotting

Western Blotting is used to determine the presence of a specific protein in different samples with a specific primary antibody. The experiments are carried out using a Novex Western blot kit (Invitrogen, Cat. #70972).

Preparation of Transfer Buffer (1×):

50 mL 20× NuPAGE transfer buffer (Invitrogen, Cat. #nbNP0006); 100 mL Methanol; 849 mL pure $H_2O$; 1 mL antioxidant.

Procedure for Western Blotting:

A) Preparation of sample for SDS-PAGE (loading samples)—5 µL 4×LDS sample buffer; 2 µL 0.5 M DTT; 13 µL Protein solution. Samples are heated at 70° C., 10 minutes; spin at 13,000 rpm, 1 minute.

B) Run SDS-PAGE (4-12% Bis-Tris NuPAGE)—10 µL of loading samples are loaded. The upper chamber is filled with 200 mL of 1×MES running Buffer and 0.5 mL antioxidant is added. The lower chamber is filled with 600 mL MES buffer and the gels are run at 150 V for 55-60 minutes.

C) Western Blotting—Nitrocellulose membrane filter paper sandwich (Invitrogen Cat. #LC 2000) and 4 blotting pads (Novex Cat. #NaEI9052) are soaked in 1× transfer buffer containing 10% methanol (prepared from 20× NuPAGE transfer buffer, Invitrogen, Cat. # NP0006-1) at room temperature for 5 minutes with shaking (on the rocker shaker, AI-7000008, set speed at 2). After SDS-PAGE, the gels are transferred to the membrane in 1× transfer buffer at room temperature, 15 V for 50 minutes. The membrane is blocked in blocking solution at room temperature for 2 hours (membrane is flipped over after 1 hour) or overnight (placed in refrigerator after 2 hours). The primary antibody is diluted with 1× blocking solution (15 mL): The membrane is incubated in diluted primary antibody for 2 hours at room temperature on a shaker (the membrane is flipped over after 1 hour). The membrane is then washed with 1×TBSTT (25 mL/membrane) for 5 minutes, 3 times, and then washed with 1×TBSTT, 20 mL of 1×TBS for 5 minutes. The membrane is then incubated in 15 mL of diluted secondary antibody (1:7,000 in blocking solution) for 1 hour at room temperature on a shaker (the membrane is flipped over after 30 minutes). The membrane is subsequently washed with 1×TBSTT, 20 mL of 1×TBS for 5 minutes. During the last wash, 15 mL of developing solution is prepared for each membrane as follows: 15 mL pure $H_2O$; 60 μL NBT solution; 60 μL BCIP solution. The wash buffer is drained and the blot is placed, protein side up, in the developing solution.

Figure 16:
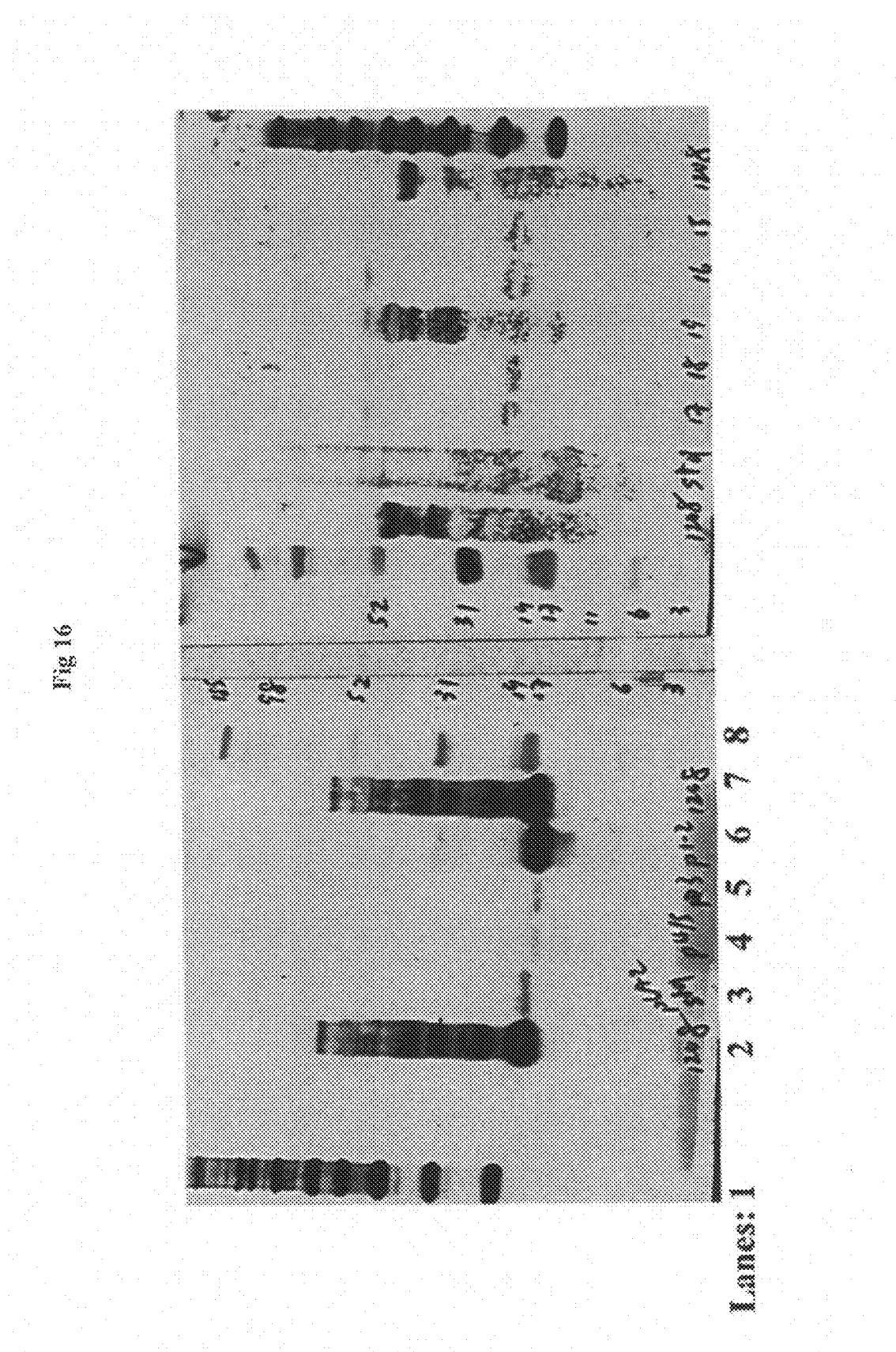
FIG. 16 shows the Western Blot of anti-$PLA_2$. Lanes—1: MagicMark; 2 and 7: RP-HPLC loading sample 1; 3: Porcine $PLA_2$ from Sigma; 4: Pancreatin API peaks 4 and 5; 5: Pancreatin API peak 3; 6: HPLC-pancreatin API peak 1 and 2; 8: MultiMark.

FIG. 16 shows the blot of anti-$PLA_2$ (immunogen: Porcine $PLA_2$; working solution: 1:500 in block solution; antibody incubation: 2 hours at room temperature for primary antibody and 1 hour for secondary antibody (1:7500)). Anti-$PLA_2$ antibody recognizes the 14 kDa protein which is present in pancreatin API peaks 1 and 2.

Figure 17:
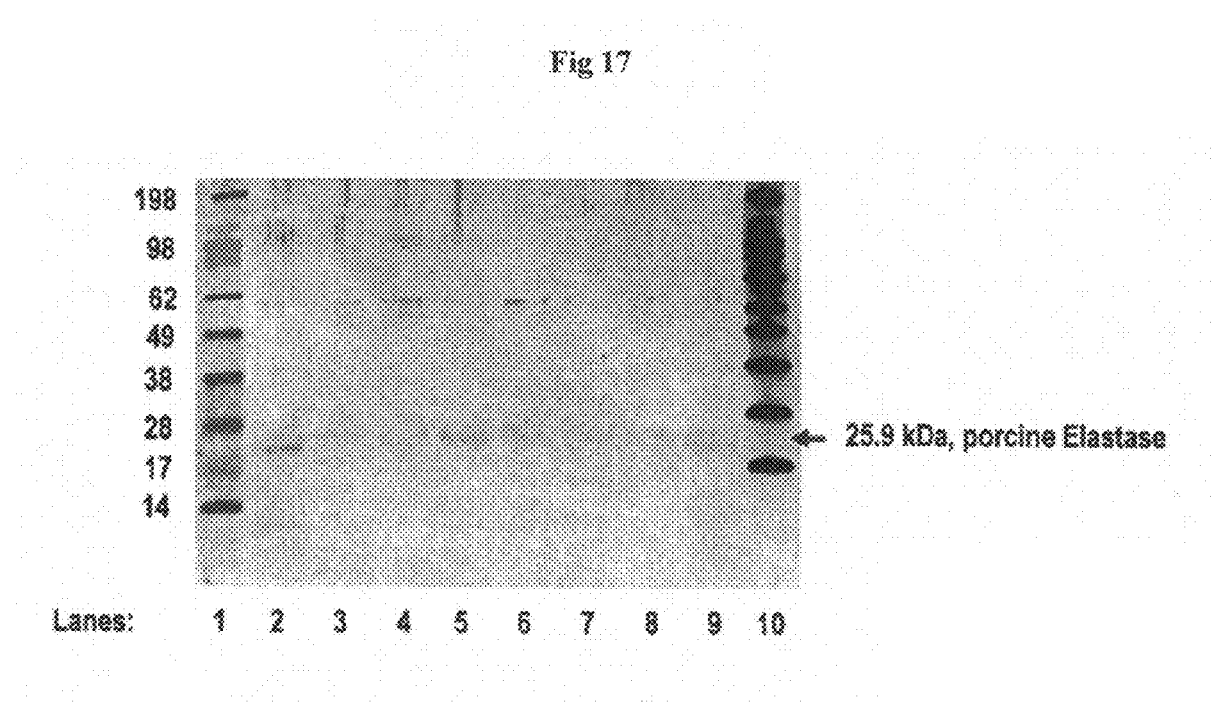
FIG. 17 shows the Western Blot of anti-elastase. Lanes—1: SeeBlue Plus2 protein marker; 2: RP-HPLC loading sample 1; 3: Porcine Elastase from Sigma; 4: Pancreatin API peak fraction 14; 5: Pancreatin API peak fraction 15; 6: Pancreatin API peak fraction 16; 7: Pancreatin API peak fraction 17; 8: Pancreatin API peak fraction 18; 9: RP-HPLC loading sample 1; 10: MagicMark.

FIG. 17 shows the blot of anti-elastase (immunogen: human pancreatic elastase; working solution: 1:1000 in block solution; antibody incubation: 2 hours at room temperature for primary antibody and 1 hour for secondary antibody (1:7500)). Anti-elastase antibody recognizes the 25.9 kDa protein which is present in pancreatin API peaks 14-18.

Figure 18:
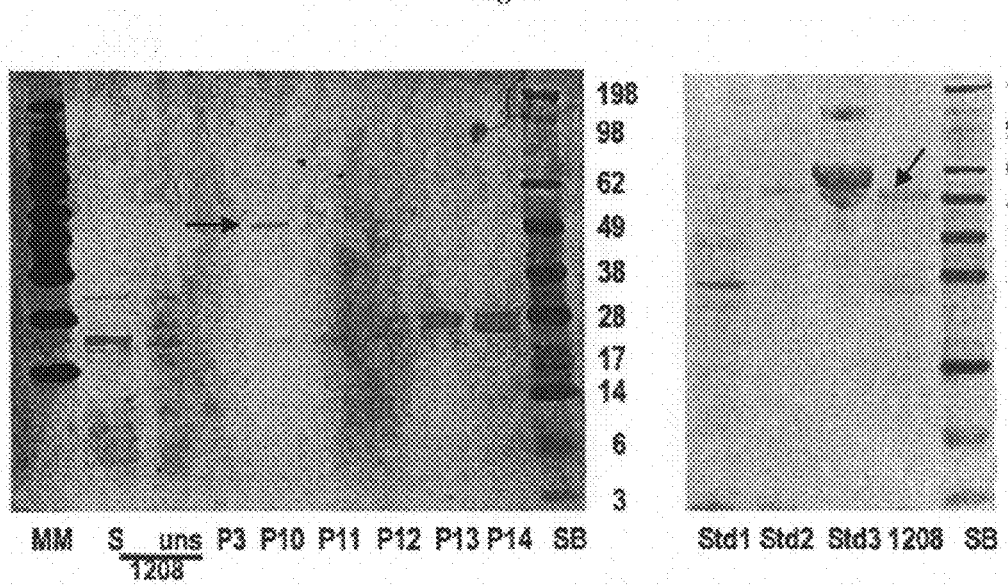
FIG. 18 shows the Western Blot of anti-lipase. S: solubilized Pancreatin API proteins; uns: unsolubilized Pancreatin API proteins; P3, P10-14: HPLC peak fractions; Std1: porcine lipase from Elastin Products Company; Std2: porcine lipase from USP; Std3: porcine lipase from Boehringer Mannhein; Pancreatin API: HPLC loading sample 1. Arrows indicate the full length porcine lipase: 49.9 kDa.

FIG. 18 shows the blot of anti-lipase (immunogen: human pancreatic lipase—full length; working solution: 1:100 in block solution; antibody incubation: 2 hours at room temperature for primary antibody and 1 hour for secondary antibody (1:7500)). Full-length porcine lipase (49.9 kDa) and truncated lipase are detected by anti-lipase antibody in pancreatin API mixture (solubilized and unsolubilized fractions), HPLC-peak fractions 3, 10-14.

Figure 19:
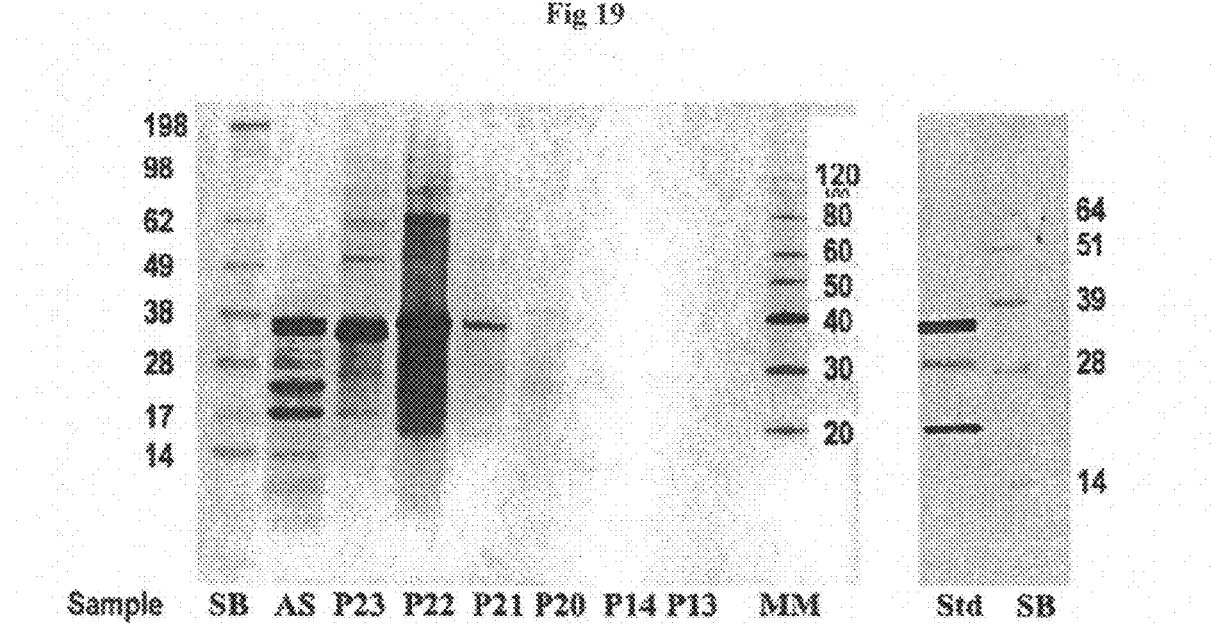
FIG. 19 shows the Western Blot of anti-CP-B. SB: SeeBlue Plus 2 protein marker; AS: HPLC-Applied sample 1; P 13-P23: HPLC peak fractions; MM: MagicMark; Std: Porcine Carboxypeptidase B from Sigma.
Figure 20:
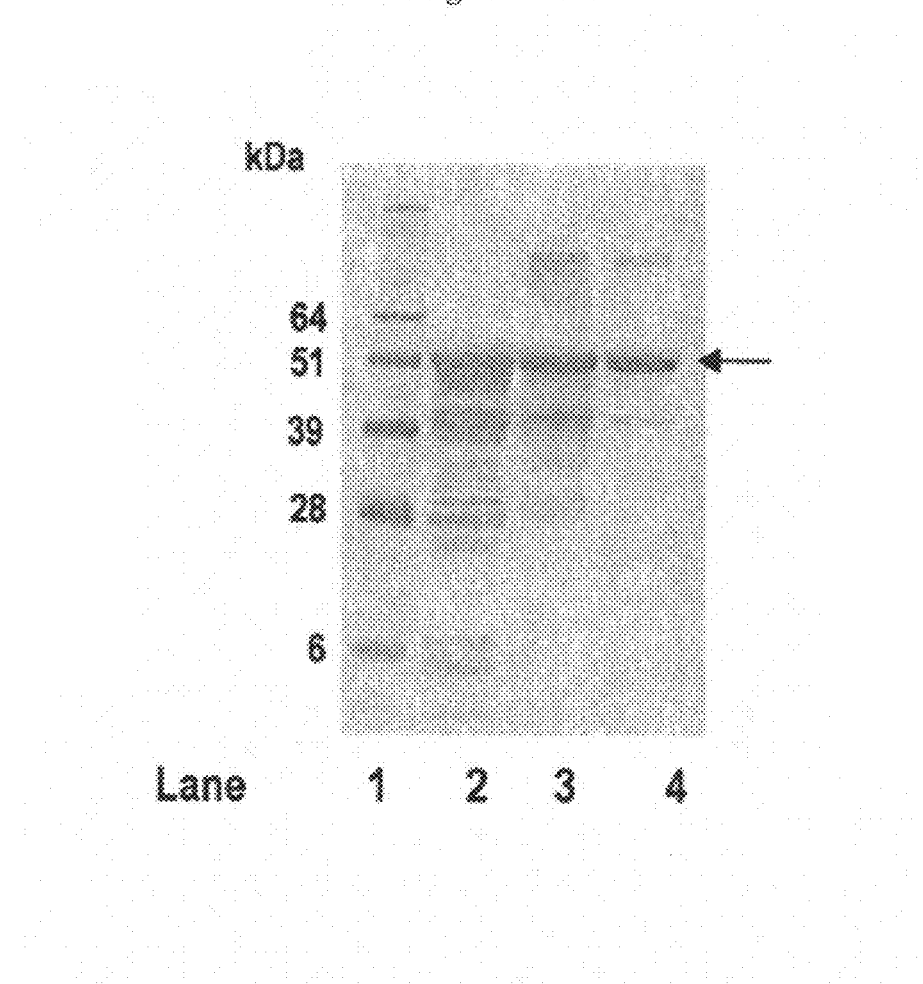
FIG. 20 shows the Western Blot of anti-amylase. Lanes—1: SeeBlue Plus2 Protein Marker; 2: HPLC loading sample 1; 3: Porcine α-Amylase from Sigma; 4: HPLC-1208 peak fraction 19. Arrow indicates the porcine amylase (full length).

FIG. 19 shows the blot of anti-CP-B (immunogen: human porcine carboxypeptidase B; working solution: 1:4000 in block solution; antibody incubation: 2 hours at room temperature for primary antibody and 1 hour for secondary antibody (1:7500)). Anti-CP-B antibody recognizes the 35 kDa protein which is present in pancreatin API peaks 21-23. FIG. 20 shows the blot of anti-amylase (immunogen: human porcine amylase; working solution: 1:4000 in block solution; antibody incubation: 2 hours at room temperature for primary antibody and 1 hour for secondary antibody (1:7500)). Anti-amylase antibody recognizes the 51 kDa protein mix, porcine standard amylase and pancreatin API-peak 19 (reported porcine amylase 50-54 kDa).

Figure 21:
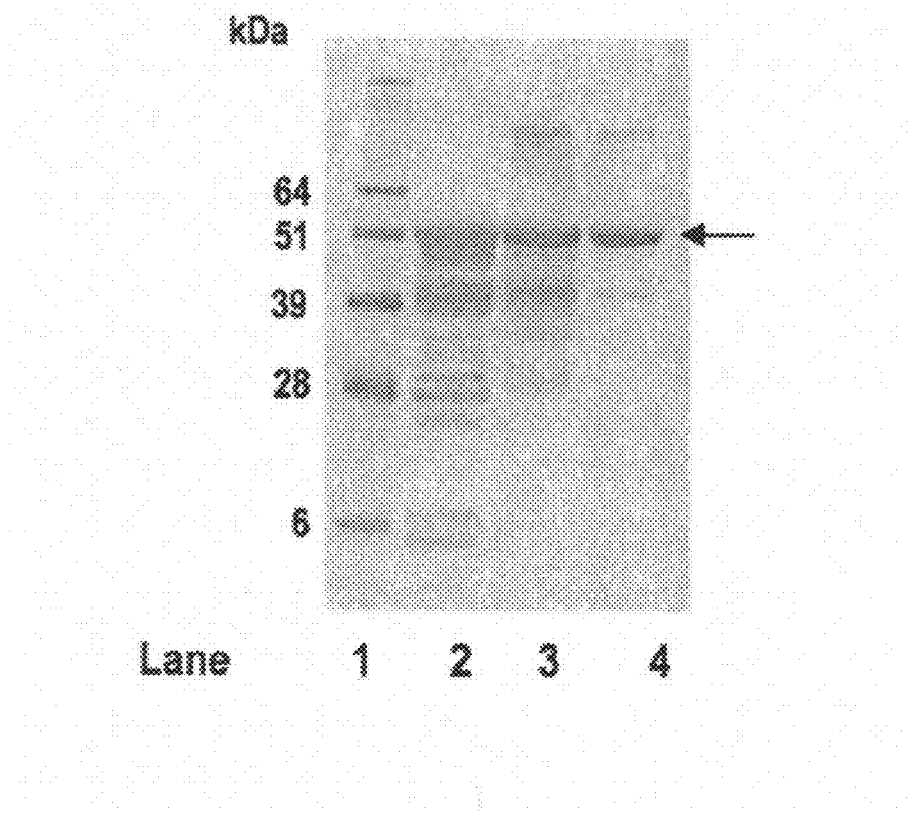
FIG. 21 shows the Western Blot of anti-trypsin. Lanes—1: SeeBlue plus2 protein Marker; 2: Standard porcine trypsin; 3: HPLC-pancreatin API peaks 6 & 7.

FIG. 21 shows the blot of anti-trypsin (immunogen: human porcine trypsin; working solution: 1:1000 in block solution; antibody incubation: 2 hours at room temperature for primary antibody and 1 hour for secondary antibody (1:7500)). Proteins in pancreatin API peaks 6 and 7 reacted with human pancreatic anti-trypsin.

Example 5

MALDI-TOF-TOF MS

Preparation of pancreatin API samples for MALDI-TOF-TOF MS:

Samples—Sample 1 fractions are lyophilized and collected from $C_4$ RP-HPLC.

Sample preparation—20 μL of 1×LDS*/mL is collected, heated at 70° C. for 10 minutes, and centrifuged at 13,000 rpm for 1 minute. *1×LDS sample buffer with 50 mM DTT: for 1 mL 250 μL of 4×LDS sample buffer; 100 μL of 0.5 M DTT; 650 μL of pure water.

SDS-PAGE—4-12% Bis-Tris NuPAGE.
Running buffer—1×MES.
Running condition: 150 V constant, 1 hour under reducing conditions.
Staining—1 hour with Simple Blue.
Enzymatic Digestion and MS analysis:

"In Gel" digestion and mass spectrometric analysis is done at the Mass Spectrometry Facility [Biotechnology Center, University of Wisconsin-Madison]. The digestion is performed as outlined on the website http://www.biotech.wisc.edu/ServicesResearch/MassSpec/ingel.htm.

In short, Coomassie G-250 (Colloidal) stained gel pieces are de-stained completely in MeOH/$H_2O$/$NH_4HCO_3$ [50%:50%:100 mM], dehydrated for 10 min in ACN/$H_2O$/$NH_4HCO_3$ [50%:50%:25 mM] then once more for 1 minute in 100% ACN, dried in a Speed-Vac for 5 minutes, reduced in 25 mM DTT [Dithiotreitol in 25 mM $NH_4HCO_3$] for 30 minutes at 56° C., alkylated with 55 mM IAA [Iodoacetamide in 25 mM $NH_4HCO_3$] in darkness at room temperature for 30 minutes, washed twice in $H_2O$ for 1 minute, equilibrated in 25 mM $NH_4HCO_3$ for 1 minute, dehydrated for 10 minutes in ACN/$H_2O$/$NH_4HCO_3$ [50%:50%:25 mM] then once more for 1 minute in 100% ACN, dried again and rehydrated with 20 μL of trypsin solution [20 ng/μL trypsin (Sequence Grade Modified from PROMEGA Corp.) in 25 mM $NH_4HCO_3$]. The digestion is conducted overnight [18 hrs] at 37° C. and subsequently terminated by acidification with equal volume of 2.5% TFA [Trifluoroacetic Acid]. Peptides generated from digestion are extracted in two subsequent steps: first with equal volume of 0.1% TFA (~50 μL) and vigorous vortexing for 15 minutes and then with the same volume of ACN/$H_2O$/TFA [70%:25%:5%] and vortexing. The collected peptide solution is dried completely in a Speed-Vac then re-suspended in 50 μL of 0.1% TFA and solid-phase extracted (ZipTip® C18 pipette tips Millipore, Billerica, Mass.). Peptides are eluted off the $C_{18}$ zip tip with acetonitrile/$H_2O$/TFA (70%:25%:0.2%) directly onto the Opti-TOF™ 384-well plate (Applied Biosystems, Foster City, Calif.) and re-crystallized with 0.5 μL of matrix [10 mg/mL α-Cyano-4-hydroxycinnamic acid in acetonitrile/$H_2O$/TFA (70%:25%:0.2%). Peptide Map Fingerprint result-dependent MS/MS analysis is performed on a 4800 Matrix-Assisted Laser Desorption/Ionization-Time of Flight-Time of Flight (MALDI TOF-TOF) mass spectrometer (Applied Biosystems, Foster City, Calif.). In short, peptide fingerprint is generated scanning 700-4,000 Da mass range using 1000 shots acquired from 20 randomized regions of the sample spot at 3600 intensity of OptiBeam™ on-axis laser in positive reflectron mode. Ten most abundant precursors, excluding trypsin autolysis peptides and sodium/potassium adducts, are selected for subsequent tandem MS analysis, where 2000 total shots are taken with 4200 laser intensity. Post-source decay (PSD) fragments from the precursors of interest are isolated by timed-ion selection and reaccelerated into the reflectron to generate the MS/MS spectrum. Raw data is deconvoluted using GPS Explorer™ software and submitted for peptide mapping and MS/MS ion search analysis against non-redundant NCBI database with an in-house licensed Mascot search engine (Matrix Science, London; UK).

Figure 22:
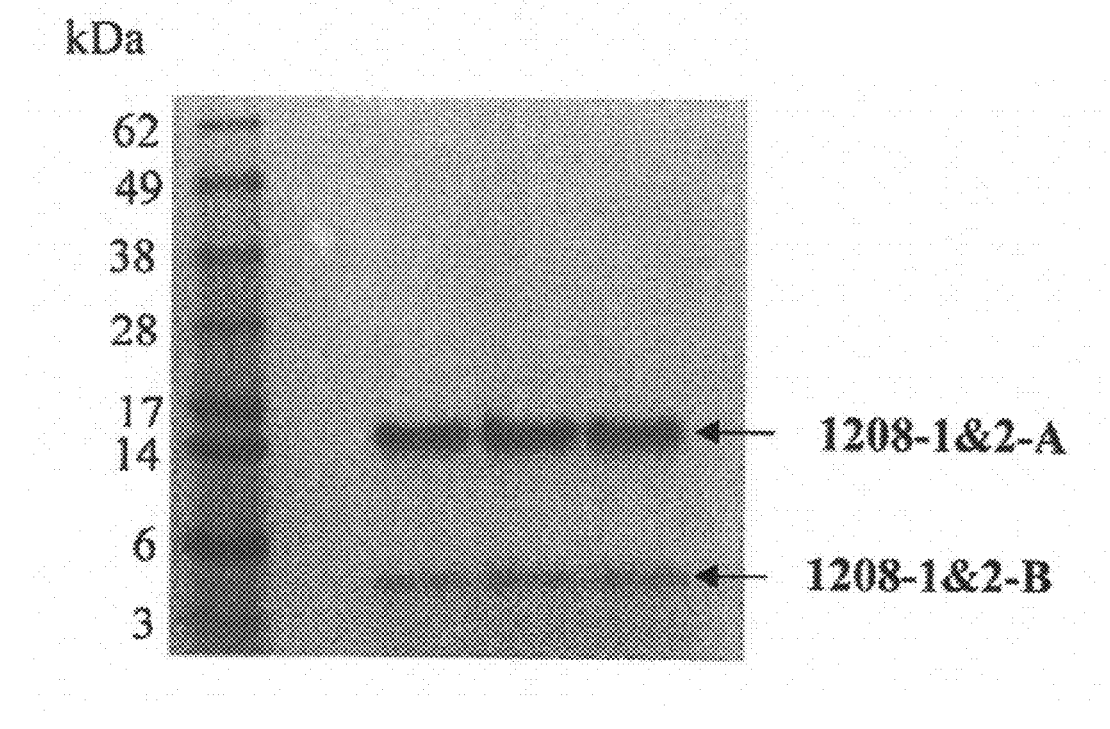
FIG. 22 Western Blot of pancreatin API-1 and -2 (API peaks 1 and 2).

MS Results:

1A) Pancreatin API-1&2-A (API peaks 1 and 2-A) (FIG. 22). Match to: gi|129436 Score: 516 Expect: 1.2e-046 Phospholipase A2, minor isoenzyme (Phosphatidylcholine 2-acyl-hydrolase).

Nominal mass (Mr): 13959, Calculated pI value: 5.61; NCBI BLAST search of gi|1129436 against nr; Taxonomy: *Sus scrofa*; Cleavage by Trypsin: cuts C-term side of KR unless next residue is P; Variable modifications: Carbamidomethyl (C), Deamidation (NQ), Oxidation (M); Sequence Coverage: 85%, Score: 61-93; Sequenced and Matched peptides (Fingerprints) shown in bold.

```
                                                         (SEQ ID NO: 1)
  1  ALWQFRSMIK CTIPGSDPLL DFNNYGCYCG LGGSGTPVDE LDRCCETHDN

51  CYRDAKNLDS CKFLVDNPYT NSYSYSCSNT EITCNSKNNA CEAFICNCDR

101  NAAICFSKAP YNKEHKNLDT KKYC
```

1B) Pancreatin API-1&2-B (FIG. 22). Match to: gi|47523482 Score: 227 Expect: 9.7e-018 pancreatic colipase [*Sus scrofa*].

Nominal mass (Mr): 12132, Calculated pI value: 5.29; NCBI BLAST search of gi|47523482 against nr; Taxonomy: *Sus scrofa*; Links to retrieve other entries containing this sequence from NCBI Entrez: gi|71063983 from *Sus scrofa*, gi|7711136 from *Sus scrofa*, gi|24418847 from *Sus scrofa*; Variable modifications: Carbamidomethyl (C), Deamidation (NQ), Oxidation (M); Cleavage by Trypsin: cuts C-term side of KR unless next residue is P; Sequence Coverage: 33%; Sequenced and Matched peptides (Fingerprints) shown in bold.

```
                                                         (SEQ ID NO: 2)
  1  MEKVLALLLV TLTVAYAVPD PRGIIINLDE GELCLNSAQC KSNCCQHDTI

51  LSLSRCALKA RENSECSAFT LYGVYYKCPC ERGLTCEGDK SLVGSITNTN

101  FGICHDVGRS SD
```

Figure 23:
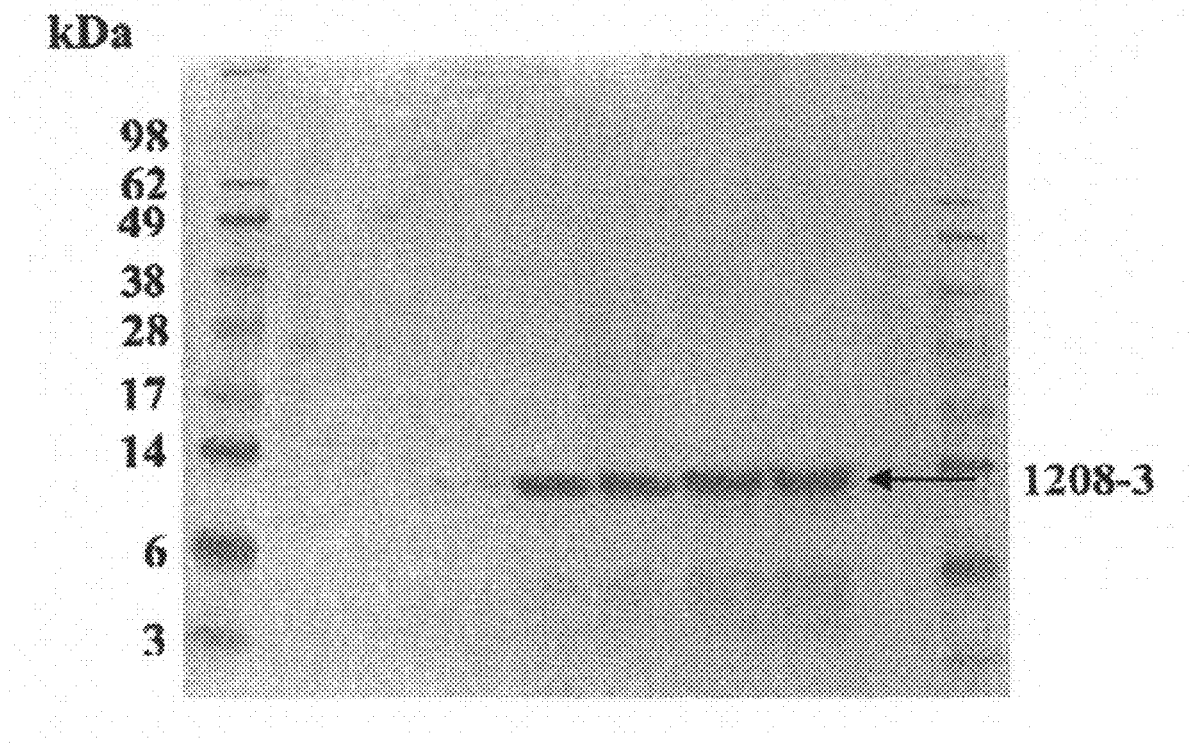
FIG. 23 Western Blot of pancreatin API-3.

2) Pancreatin API-3 (FIG. 23). Match to: gi|67161 Score: 147 Expect: 9.7e-010; triacylglycerol lipase (EC 3.1.1.3)—pig.

Nominal mass ($M_r$): 49894; Calculated pI value: 5.63; NCBI BLAST search of gi|67161 against nr; Unformatted sequence string for pasting into other applications; Taxonomy: *Sus scrofa domestica*; Variable modifications: Carbamidomethyl (C), Deamidation (NQ), Oxidation (M); Cleavage by Trypsin: cuts C-term side of KR unless next residue is P; Sequence Coverage: 18%; Matched peptides shown in bold.

```
                                                         (SEQ ID NO: 3)
  1  SEVCFPRLGC FSDDAPWAGI VQRPLKILPP DKDVDTRFLL YTNQNQNNYQ

51  ELVADPSTIT NSNFRMDRKT RFIIHGFIDK GEEDWLSNIC KNLFKVESVN

101  CICVDWKGGS RTGYTQASQN IRIVGAEVAY FVEVLKSSLG YSPSNVHVIG

151  HSLGSHAAGE AGRRTNGTIE RITGLDPAEP CFQGTPELVR LDPSDAKFVD

201  VIHTDAAPII PNLGFGMSQT VGHLDFFPNG GKQMPGCQKN ILSQIVDIDG
```

```
251 IWEGTRDFVA CNHLRSYKYY ADSILNPDGF AGFPCDSYNV FTANKCFPCP

301 SEGCPQMGHY ADRFPGKTNG VSQVFYLNTG DASNFARWRY KVSVTLSGKK

351 VTGHILVSLF GNEGNSRQYE IYKGTLQPDN THSDEFDSDV EVGDLQKVKF

401 IWYNNNVINP TLPRVGASKI TVERNDGKVY DFCSQETVRE EVLLTLNPC
```

Figure 24:
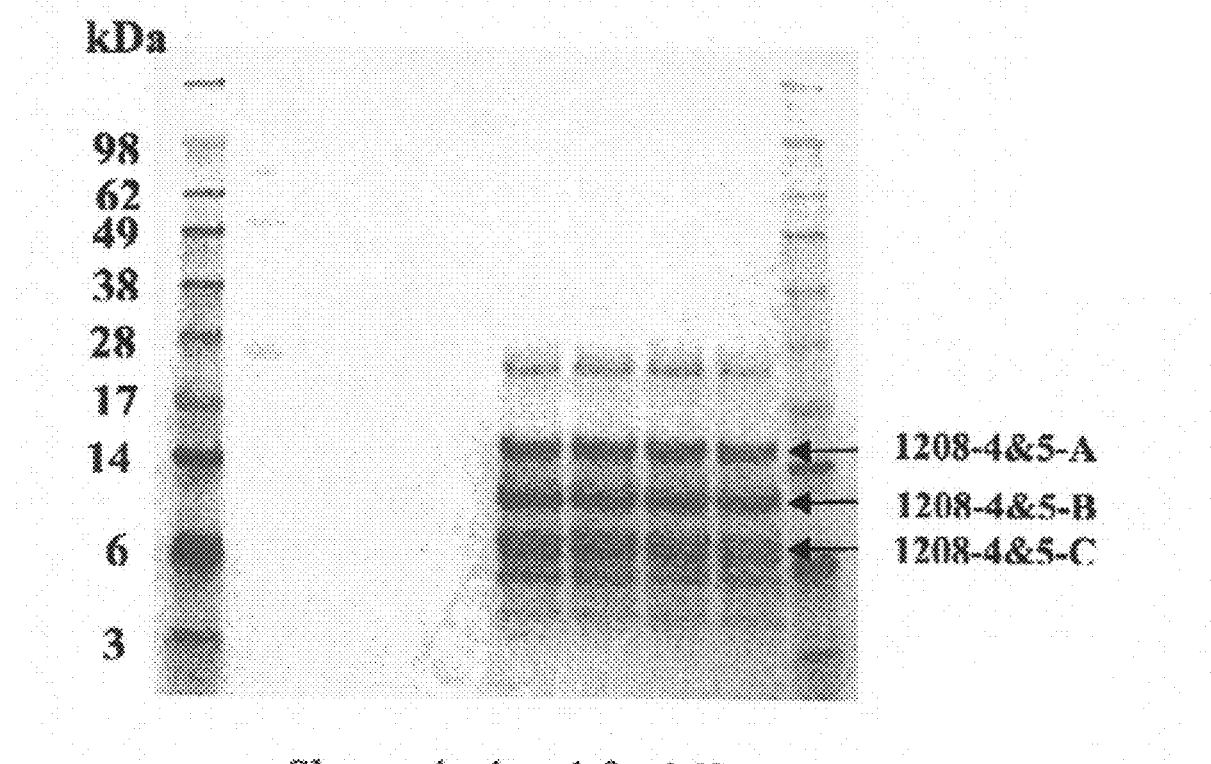
FIG. 24 Western Blot of analysis of pancreatin API-4 and 5.

3A) Pancreatin API-4 and 5-A (FIG. 24). Match to: gi|62738255 Score: 138 Expect: 7.7e-009; Chain A, Crystal Structure Of The Pig Pancreatic Alpha-Amylase Complexed With Malto-Oligosaacharide.

Nominal mass ($M_r$): 55381; Calculated pI value: 5.91; NCBI BLAST search of gi|62738255 against nr; Taxonomy: *Sus scrofa*; Links to retrieve other entries containing this sequence from NCBI Entrez: gi|15825762 from *Sus scrofa*; Sequence Coverage: 20%; Matched peptides shown in bold.

```
                                                    (SEQ ID NO: 4)
  1 XYAPQTQSGR TSIVHLFEWR WVDIALECER YLGPKGFGGV QVSPPNENIV

51 VTNPSRPWWE RYQPVSYKLC TRSGNENEFR DMVTRCNNVG VRIYVDAVIN

101 HMCGSGAAAG TGTTCGSYCN PGNREFPAVP YSAWDFNDGK CKTASGGIES

151 YNDPYQVRDC QLVGLLDLAL EKDYVRSMIA DYLNKLIDIG VAGFRIDASK

201 HMWPGDIKAV LDKLHNLNTN WFPAGSRPFI FQEVIDLGGE AIKSSEYFGN

251 GRVTEFKYGA KLGTVVRKWS GEKMSYLKNW GEGWGFMPSD RALVFVDNHD

301 NQRGHGAGGS SILTFWDARL YKIAVGFMLA HPYGFTRVMS SYRWARNFVN

351 GEDVNDWIGP PNNNGVIKEV TINADTTCGN DWVCEHRWRE IRNMVWFRNV

401 VDGQPFANWW DNGSNQVAFG RGNRGFIVFN NDDWQLSSTL QTGLPGGTYC

451 DVISGDKVGN SCTGIKVYVS SDGTAQFSIS NSAEDPFIAI HAESKL
```

3B) Pancreatin API-4 and 5-B (FIG. 24). Match to: gi|3318722 Score: 120 Expect: 4.8e-007; Chain E, Leech-Derived Tryptase Inhibitor TRYPSIN COMPLEX.

Nominal mass ($M_r$): 23457; Calculated pI value: 8.26; NCBI BLAST search of gi|3318722 against nr; Taxonomy: *Sus scrofa*; gi|9954879 from *Sus scrofa*; Sequence Coverage: 29%; Matched peptides shown in bold.

```
                                                    (SEQ ID NO: 5)
  1 IVGGYTCAAN SIPYQVSLNS GSHFCGGSLI NSQWVVSAAH CYKSRIQVRL

51 GEHNIDVLEG NEQFINAAKI ITHPNFNGNT LDNDIMLIKL SSPATLXSRV

101 ATVSLPRSCA AAGTECLISG WGNTKSSGSS YPSLLQCLKA PVLSDSSCKS

151 SYPGQITGNM ICVGFLEGGK DSCQGDSGGP VVCNGQLQGI VSWGYGCAQK

201 NKPGVYTKVC NYVNWIQQTI AAN
```

3C) Pancreatin API-4 and 5-C (FIG. 24). Match to: gi|2098469 Score: 132 Expect: 3.1e-008; Porcine Pancreatic Alpha-Amylase Complexed with Acarbose.

Nominal mass ($M_r$): 55325; Calculated pI value: 5.68; NCBI BLAST search of gi|2098469 against nr; Taxonomy: *Sus scrofa*; Sequence Coverage: 15%; Matched peptides shown in bold.

```
                                                    (SEQ ID NO: 6)
  1 XYAPQTQSGR TSIVHLFEWR WVDIALECER YLGPKGFGGV QVSPPNENIV

51 VTNPSRPWWE RYQPVSYKLC TRSGNENEFR DMVTRCNNVG VRIYVDAVIN
```

```
101  HMCGSGAAAG  TGTTCGSYCN  PGSREFPAVP  YSAWDFNDGK  CKTASGGIES

151  YNDPYQVRDC  QLVGLLDLAL  EKDYVRSMIA  DYLNKLIDIG  VAGFRIDASK

201  HMWPGDIKAV  LDKLHNLNTN  WFPAGSRPFI  FQEVIDLGGE  AIQSSEYFGN

251  GRVTEFKYGA  KLGTVVRKWS  GEKMSYLKNW  GEGWGFMPSD  RALVFVDNHD

301  NQRGHGAGGA  SILTFWDARL  YKVAVGFMLA  HPYGFTRVMS  SYRWARNFVN

351  GEDVNDWIGP  PNNNGVIKEV  TINADTTCGN  DWVCEHRWRE  IRNMVWFRNV

401  VDGEPFANWW  DNGSNQVAFG  RGNRGFIVFN  NDDWQLSSTL  QTGLPGGTYC

451  DVISGDKVGN  SCTGIKVYVS  SDGTAQFSIS  NSAEDPFIAI  HAESKL
```

Figure 25:
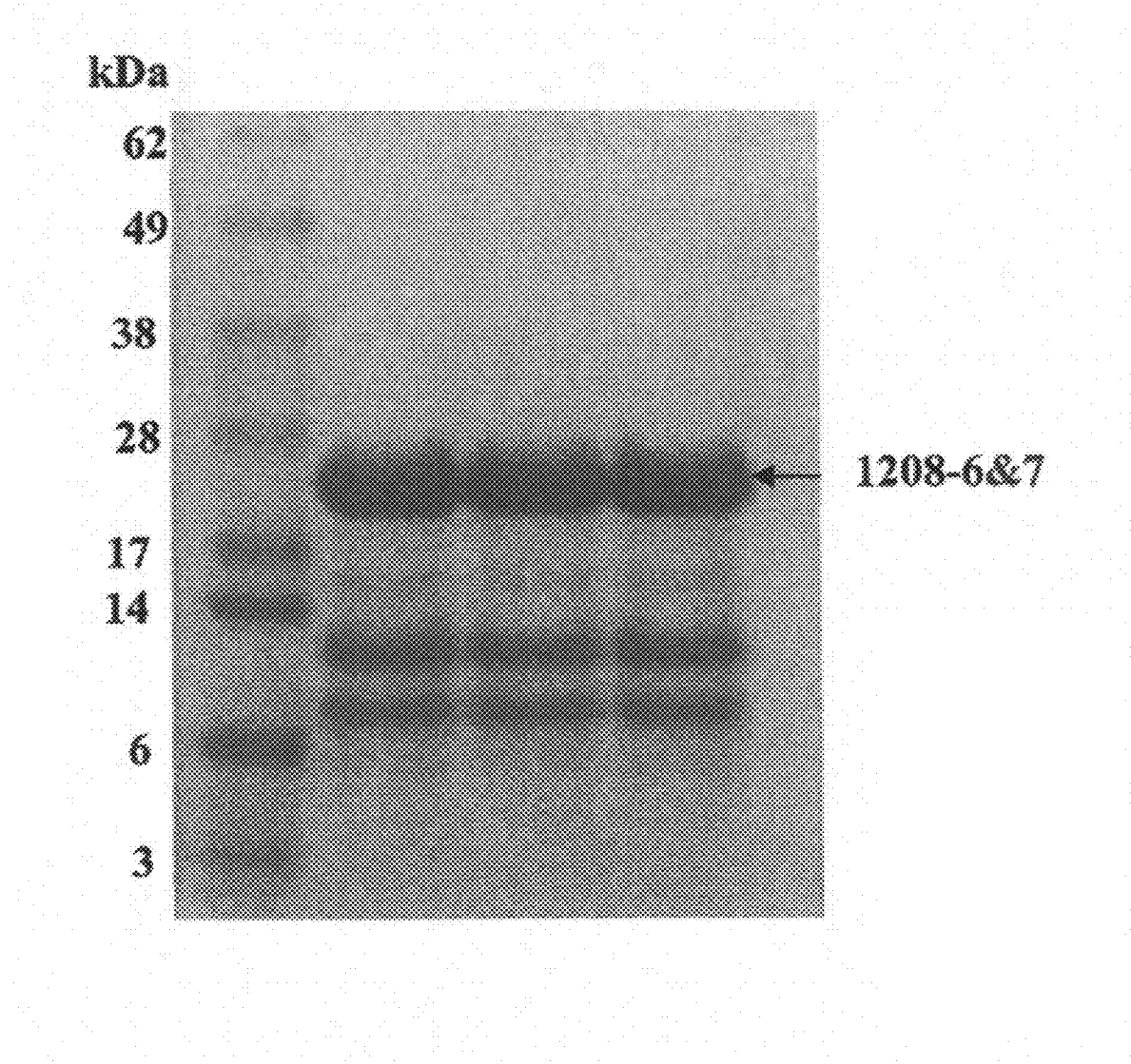
FIG. 25 Western Blot of analysis of pancreatin API-6 and -7.

4) Pancreatin API-6 and 7 (FIG. 25). Match to: gi|136429 Score: 296 Expect: 1.2e-024.

Nominal mass (Mr): 24394, Calculated pI value: 7.00; Taxonomy: *Sus scrofa*; Sequence Coverage: 44%; Sequenced and Matched peptides shown in bold.

```
                                                    (SEQ ID NO: 7)
  1  FPTDDDDKIV  GGYTCAANSI  PYQVSLNSGS  HFCGGSLINS  QWVVSAAHCY

51  KSRIQVRLGE  HNIDVLEGNE  QFINAAKIIT  HPNFNGNTLD  NDIMLIKLSS

101  PATLNSRVAT  VSLPRSCAAA  GTECLISGWG  NTKSSGSSYP  SLLQCLKAPV

151  LSDSSCKSSY  PGQITGNMIC  VGFLEGGKDS  CQGDSGGPVV  CNGQLQGIVS

201  WGYGCAQKNK  PGVYTKVCNY  VNWIQQTIAA  N
```

Figure 26:
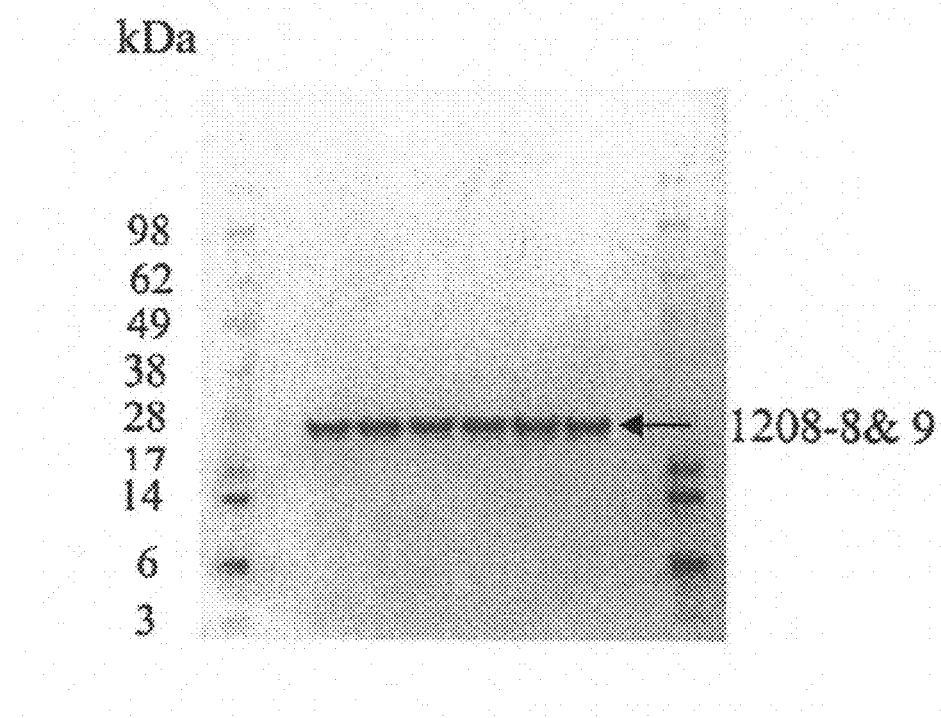
FIG. 26 Western Blot of pancreatin API-8 and -9.

5) Pancreatin API-8 and 9 (FIG. 26). Match to: gi|47523026 Score: 405 Expect: 1.5e-035; pancreatic elastase II [*Sus scrofa*].

Nominal mass ($M_r$): 28681, Calculated pI value: 8.33; NCBI BLAST search of gi|47523026 against nr; Unformatted sequence string for pasting into other applications; Taxonomy: *Sus scrofa*; Links to retrieve other entries containing this sequence from NCBI Entrez: gi|119258 from *Sus scrofa*, gi|164442 from *Sus scrofa*; Variable modifications: Carbamidomethyl (C), Deamidation (NQ), Oxidation (M); Cleavage by Trypsin: cuts C-term side of KR unless next residue is P; Sequence Coverage: 54%; Matched peptides shown in bold.

```
                                                    (SEQ ID NO: 8)
  1  MIRALLLSTL  VAGALSCGLP  ANLPQLPRVV  GGEDARPNSW  PWQVSLQYDS

51  SGQWRHTCGG  TLVDQSWVLT  AAHCISSSRT  YRVVLGRHSL  STNEPGSLAV

101  KVSKLVVHQD  WNSNQLSNGN  DIALLKLASP  VSLTDKIQLG  CLPAAGTILP

151  NNYVCYVTGW  GRLQTNGASP  DILQQGQLLV  VDYATCSKPG  WWGSTVKTNM

201  ICAGGDGIIS  SCNGDSGGPL  NCQGANGQWQ  VHGIVSFGSS  LGCNYYHKPS
```

Figure 27:
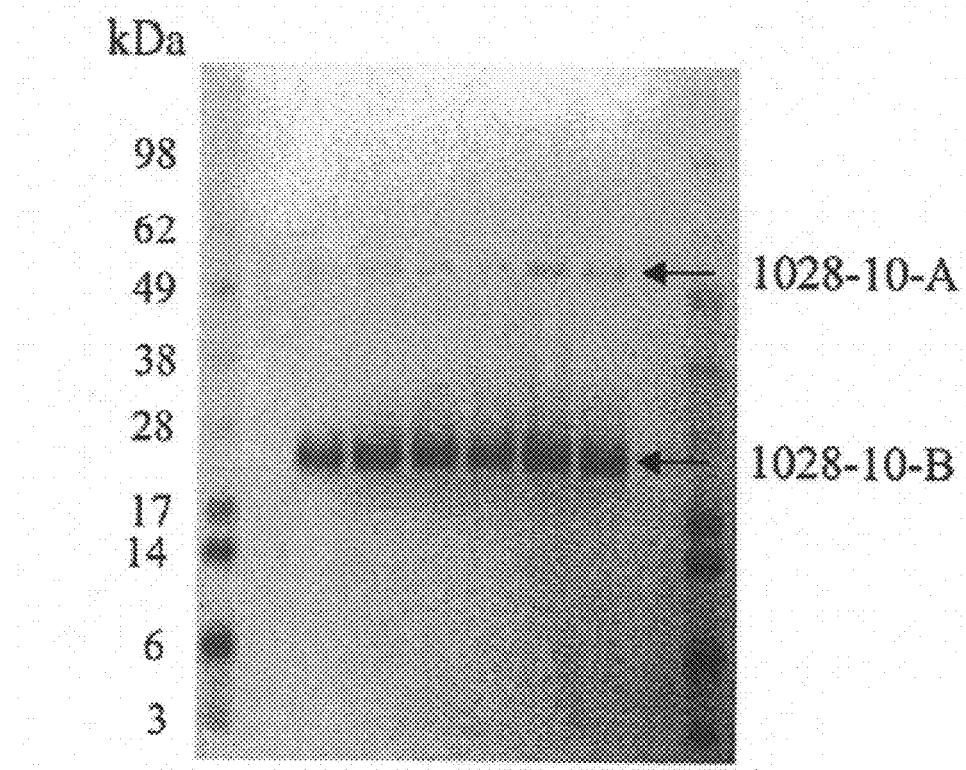
FIG. 27 Western Blot of pancreatin API-10.

6A) Pancreatin API-10-A (FIG. 27). Match to: gi|67161 Score: 486 Expect: 1.2e-043; triacylglycerol lipase (EC 3.1.1.3)—pig.

Nominal mass ($M_r$): 49894; Calculated pI value: 5.63; NCBI BLAST search of gi|67161 against nr; Unformatted sequence string for pasting into other applications; Taxonomy: *Sus scrofa domestica*; Sequence Coverage: 56%; Matched peptides shown in bold.

```
                                                    (SEQ ID NO: 9)
  1  SEVCFPRLGC  FSDDAPWAGI  VQRPLKILPP  DKDVDTRFLL  YTNQNQNNYQ

51  ELVADPSTIT  NSNFRMDRKT  RFIIHGFIDK  GEEDWLSNIC  KNLFKVESVN
```

```
101  CICVDWKGGS  RTGYTQASQN  IRIVGAEVAY  FVEVLKSSLG  YSPSNVHVIG

151  HSLGSHAAGE  AGRRTNGTIE  RITGLDPAEP  CFQGTPELVR  LDPSDAKFVD

201  VIHTDAAPII  PNLGFGMSQT  VGHLDFFPNG  GKQMPGCQKN  ILSQIVDIDG

251  IWEGTRDFVA  CNHLRSYKYY  ADSILNPDGF  AGFPCDSYNV  FTANKCFPCP

301  SEGCPQMGHY  ADRFPGKTNG  VSQVFYLNTG  DASNFARWRY  KVSVTLSGKK

351  VTGHILVSLF  GNEGNSRQYE  IYKGTLQPDN  THSDEFDSDV  EVGDLQKVKF

401  IWYNNNVINP  TLPRVGASKI  TVERNDGKVY  DFCSQETVRE  EVLLTLNPC
```

6b) Pancreatin API-10-B: similar to chymotrypsin-like (FIG. 27*b*). Match to: gi|73957472 Score: 129 Expect: 6.1e-008; PREDICTED: similar to chymotrypsin-like.

Nominal mass (M$_r$): 28200; Calculated pI value: 8.85; NCBI BLAST search of gi|73957472 against nr; Taxonomy: *Canis familiaris*; Sequence Coverage: 12%; Matched peptides shown in bold.

```
                                                    (SEQ ID NO: 10)
  1  MLLLSLTLSL  VLLGSSWGCG  IPAIKPVLSF  SQRIVNGENA  VPGSWPWQVS

51  LQDKSGFHFC  GGSLISQSWV  VTAAHCNVIP  GRHVVVLGEY  DRSSNAEPLQ

101  VLSISKAITY  PSWNPTTLNN  DLTLLKLASP  ARYTQRISPV  CLASPDEELP

151  AGLKCATTGW  GRLSGVGNVT  PARLQQVALP  LVTVNECRQY  WGSRITDAMI

201  CAGGSGASSC  QGDSGGPLVC  QKGNTWVLIG  IVSWGTTNCN  VRQPAIYTRV

251  SKFSTWISQV  IAYN
```

7A) Pancreatin API-12-A: triacylglycerol lipase (EC 3.1.1.3) (FIG. 28).

Nominal mass (Mr): 49894; Calculated pI value: 5.63; Taxonomy: *Sus scrofa domestica*; Sequence Coverage: 62%, Score: 80-98; Matched peptides shown in bold.

```
                                                    (SEQ ID NO: 11)
  1  SEVCFPRLGC  FSDDAPWAGI  VQRPLKILPP  DKDVDTRFLL  YTNQNQNNYQ

51  ELVADPSTIT  NSNFRMDRKT  RFIIHGFIDK  GEEDWLSNIC  KNLFKVESVN

101  CICVDWKGGS  RTGYTQASQN  IRIVGAEVAY  FVEVLKSSLG  YSPSNVHVIG

151  HSLGSHAAGE  AGRRTNGTIE  RITGLDPAEP  CFQGTPELVR  LDPSDAKFVD

201  VIHTDAAPII  PNLGFGMSQT  VGHLDFFPNG  GKQMPGCQKN  ILSQIVDIDG

251  IWEGTRDFVA  CNHLRSYKYY  ADSILNPDGF  AGFPCDSYNV  FTANKCFPCP

301  SEGCPQMGHY  ADRFPGKTNG  VSQVFYLNTG  DASNFARWRY  KVSVTLSGKK

351  VTGHILVSLF  GNEGNSRQYE  IYKGTLQPDN  THSDEFDSDV  EVGDLQKVKF

401  IWYNNNVINP  TLPRVGASKI  TVERNDGKVY  DFCSQETVRE  EVLLTLNPC
```

7B) Pancreatin API-12-B: triacylglycerol lipase (EC 3.1.1.3) (FIG. 28).

Nominal mass (Mr): 49894; Calculated pI value: 5.63; Taxonomy: *Sus scrofa domestica*; Sequence Coverage: 33%; Matched peptides shown in bold.

```
                                                    (SEQ ID NO: 12)
  1  SEVCFPRLGC  FSDDAPWAGI  VQRPLKILPP  DKDVDTRFLL  YTNQNQNNYQ

51  ELVADPSTIT  NSNFRMDRKT  RFIIHGFIDK  GEEDWLSNIC  KNLFKVESVN
```

```
101  CICVDWKGGS RTGYTQASQN IRIVGAEVAY FVEVLKSSLG YSPSNVHVIG

151  HSLGSHAAGE AGRRTNGTIE RITGLDPAEP CFQGTPELVR LDPSDAKFVD

201  VIHTDAAPII PNLGFGMSQT VGHLDFFPNG GKQMPGCQKN ILSQIVDIDG

251  IWEGTRDFVA CNHLRSYKYY ADSILNPDGF AGFPCDSYNV FTANKCFPCP

301  SEGCPQMGHY ADRFPGKTNG VSQVFYLNTG DASNFARWRY KVSVTLSGKK

351  VTGHILVSLF GNEGNSRQYE IYKGTLQPDN THSDEFDSDV EVGDLQKVKF

401  IWYNNNVINP TLPRVGASKI TVERNDGKVY DFCSQETVRE EVLLTLNPC
```

7C) Pancreatin API-12-C (FIG. 28): Lithostathine precursor (FIG. 27c). Match to: gi|3024090 Score: 104 Expect: 1.9e-005.

Nominal mass (Mr): 13140; Calculated pI value: 4.85; Taxonomy: *Sus scrofa*; Sequence Coverage: 32%, scor: 95; Matched peptides shown in bold.

```
                                                        (SEQ ID NO: 13)
  1  MLPSMSLPSL XWMLLSCLML LSQVQGEDSP ADTPSARISC PKGSMAYASY

51  CYALFITPKT WMGADMACQK RPSGHLVSVL SGAEASFVSS LIKNNLNALS

101  DVWIGLHDPT EGLEPNAGGW EW
```

7D) Pancreatin API-12-D (FIG. 28): Chain A, The Structure Of Native Porcine Pancreatic Elastase. Match to: gi|7546312 Score: 121 Expect: 3.8e-007.

Nominal mass (Mr): 25904; Calculated pI value: 8.42; Sequence Coverage: 34%; Taxonomy: *Sus scrofa*; Matched peptides shown in bold.

```
                                                        (SEQ ID NO: 14)
  1  XVGGTEAQRN SWPSQISLQY RSGSSWAHTC GGTLIRQNWV MTAAHCVDRE

51  LTFRVVVGEH NLNQNDGTEQ YVGVQKIVVH PYWNTDDVAA GYDIALLRLA

101  QSVTLNSYVQ LGVLPRAGTI LANNSPCYIT GWGLTRTNGQ LAQTLQQAYL

151  PTVDYAICSS SSYWGSTVKN SMVCAGGDGV RSGCQGDSGG PLHCLVNGQY

201  AVHGVTSFVS RLGCNVTRKP TVFTRVSAYI SWINNVIASN
```

7E) Pancreatin API-12-E (FIG. 28): Chain A, The Structure Of Native Porcine Pancreatic Elastase. Match to: gi|7546312 Score: 206 Expect: 1.2e-015.

Nominal mass (Mr): 25904; Calculated pI value: 8.42; Taxonomy: *Sus scrofa*; Sequence Coverage: 35%; Matched peptides shown in bold.

```
                                                        (SEQ ID NO: 15)
  1  XVGGTEAQRN SWPSQISLQY RSGSSWAHTC GGTLIRQNWV MTAAHCVDRE

51  LTFRVVVGEH NLNQNDGTEQ YVGVQKIVVH PYWNTDDVAA GYDIALLRLA
```

```
101  QSVTLNSYVQ LGVLPRAGTI LANNSPCYIT GWGLTRTNGQ LAQTLQQAYL

151  PTVDYAICSS SSYWGSTVKN SMVCAGGDGV RSGCQGDSGG PLHCLVNGQY

201  AVHGVTSFVS RLGCNVTRKP TVFTRVSAYI SWINNVIASN
```

Figure 29A:
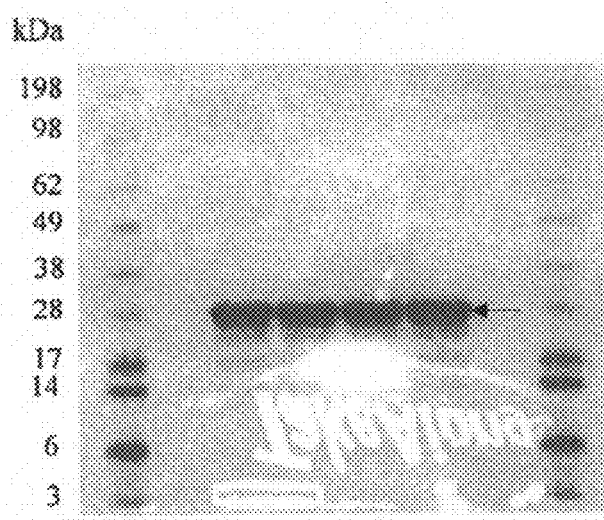
FIG. 29 a) Western Blot and MS b) of pancreatin API-13.

8) Pancreatin API-13 (FIG. 29a): The MS spectrum is good (FIG. 29b). The four most abundant peptides are selected for subsequent tandem MS analysis (see Table 8). No matching sequence is found.

TABLE 8

| Peptide | MS | Sequence | Match (bold) |
| --- | --- | --- | --- |
| 1 | 901.52 | QGNSLLLR (SEQ ID NO: 16) | |
| 2 | 1006.48 | NWNEMGVR (SEQ ID NO: 17) | Envelope glycoprotein (AAV69229.1) |
| 3 | 2468.12 | RDHVKDDPGIPINAGD[251.07]GERR (SEQ ID NO: 18) | Elastase 3B |
| 4 | 2989.43 | WLTFCAHDHRPKVQSQNPRNGAAGEPA (SEQ ID NO: 19) | |

9A) Pancreatin API-14-A: MS results are the same as that of pancreatin API-13.

9B) Pancreatin API-14-B (FIG. 30): Chain A, Crystal Structure Of Porcine Pancreatic Elastase Complexed With A Macroclyclic.

Nominal mass (Mr): 25892; Calculated pI value: 8.44; NCBI BLAST search of gi|109157401 against nr; Unformatted sequence string for pasting into other applications; gi|4930034 from *Sus scrofa*; Sequence Coverage: 52%; Matched peptides shown in bold.

```
                                                      (SEQ ID NO: 20)
 1   VVGGTEAQRN SWPSQISLQY RSGSSWAHTC GGTLIRQNWV MTAAHCVDRE

51   LTFRVVVGEH NLNQNDGTEQ YVGVQKIVVH PYWNTDDVAA GYDIALLRLA

101  QSVTLNSYVQ LGVLPRAGTI LANNSPCYIT GWGLTRTNGQ LAQTLQQAYL

151  PTVDYAICSS SSYWGSTVKN SMVCAGGDGV RSGCQGDSGG PLHCLVNGQY

201  AVHGVTSFVS RLGCNVTRKP TVFTRVSAYI SWINNVIASN
```

10A) Pancreatin API-15-A (FIG. 31): Chain A, The Structure Of Native Porcine Pancreatic Elastase.

Nominal mass (Mr): 25904; Calculated pI value: 8.42; NCBI BLAST search of gi|7546312 against nr; Taxonomy: *Sus scrofa*; Sequence Coverage: 59%, score: 84; Matched peptides shown in bold.

```
                                                      (SEQ ID NO: 21)
 1   XVGGTEAQRN SWPSQISLQY RSGSSWAHTC GGTLIRQNWV MTAAHCVDRE

51   LTFRVVVGEH NLNQNDGTEQ YVGVQKIVVH PYWNTDDVAA GYDIALLRLA
```

```
                                                              -continued
101   QSVTLNSYVQ LGVLPRAGTI LANNSPCYIT GWGLTRTNGQ LAQTLQQAYL

151   PTVDYAICSS SSYWGSTVKN SMVCAGGDGV RSGCQGDSGG PLHCLVNGQY

201   AVHGVTSFVS RLGCNVTRKP TVFTRVSAYI SWINNVIASN
```

10B) Pancreatin API-15-B (FIG. 31): Chain A, The Structure Of Native Porcine Pancreatic Elastase.

Nominal mass (Mr): 25904; Calculated pI value: 8.42; NCBI BLAST search of gi|7546312 against nr; Taxonomy: *Sus scrofa*; Sequence Coverage: 59%, Score: 64-85; Matched peptides shown in bold.

```
                                                            (SEQ ID NO: 22)
  1   XVGGTEAQRN SWPSQISLQY RSGSSWAHTC GGTLIRQNWV MTAAHCVDRE

51   LTFRVVVGEH NLNQNDGTEQ YVGVQKIVVH PYWNTDDVAA GYDIALLRLA

101   QSVTLNSYVQ LGVLPRAGTI LANNSPCYIT GWGLTRTNGQ LAQTLQQAYL

151   PTVDYAICSS SSYWGSTVKN SMVCAGGDGV RSGCQGDSGG PLHCLVNGQY

201   AVHGVTSFVS RLGCNVTRKP TVFTRVSAYI SWINNVIASN
```

10C) Pancreatin API-15-B (FIG. 31): Pancreatic colipase.

Nominal mass (Mr): 12132; Calculated pI value: 5.29; NCBI BLAST search of gi|47523482 against nr; gi|71063983 from *Sus scrofa*; gi|7711136 from *Sus scrofa*; gi|24418847 from *Sus scrofa*; Sequence Coverage: 70%; Matched peptides shown in bold.

```
                                                            (SEQ ID NO: 23)
  1   MEKVLALLLV TLTVAYAVPD PRGIIINLDE GELCLNSAQC KSNCCQHDTI

51   LSLSRCALKA RENSECSAFT LYGVYYKCPC ERGLTCEGDK SLVGSITNTN

101   FGICHDVGRS SD
```

11) Pancreatin API-17 (FIG. 32): Chain A, The Structure Of Native Porcine Pancreatic Elastase.

Nominal mass (Mr): 25904; Calculated pI value: 8.42; NCBI BLAST search of gi|7546312 against nr; Taxonomy: *Sus scrofa*; Sequence Coverage: 42%; Matched peptides shown in bold.

```
                                                            (SEQ ID NO: 24)
  1   XVGGTEAQRN SWPSQISLQY RSGSSWAHTC GGTLIRQNWV MTAAHCVDRE

51   LTFRVVVGEH NLNQNDGTEQ YVGVQKIVVH PYWNTDDVAA GYDIALLRLA

101   QSVTLNSYVQ LGVLPRAGTI LANNSPCYIT GWGLTRTNGQ LAQTLQQAYL

151   PTVDYAICSS SSYWGSTVKN SMVCAGGDGV RSGCQGDSGG PLHCLVNGQY

201   AVHGVTSFVS RLGCNVTRKP TVFTRVSAYI SWINNVIASN
```

12A) Pancreatin API-19-A (FIG. 33): Chain A, Structure Of Porcine Pancreatic Alpha-Amylase. Match to: gi|2780980 Score: 828 Expect: 7.7e-078.

Nominal mass (Mr): 55310; Calculated pI value: 5.79; NCBI BLAST search of gi|2780980 against nr; Taxonomy: *Sus scrofa*; Sequence Coverage: 36%; Matched peptides shown in bold.

```
                                                            (SEQ ID NO: 25)
  1   XYAPQTQSGR TSIVHLFEWR WVDIALECER YLGPKGFGGV QVSPPNENVV

51   VTNPSRPWWE RYQPVSYKLC TRSGNENEFR DMVTRCNNVG VRIYVDAVIN
```

```
101  HMCGSGAAAG  TGTTCGSYCN  PGSREFPAVP  YSAWDFNDGK  CKTASGGIES

151  YNDPYQVRDC  QLVGLLDLAL  EKDYVRSMIA  DYLNKLIDIG  VAGFRIDASK

201  HMWPGDIKAV  LDKLHNLNTN  WFPAGSRPFI  FQEVIDLGGE  AIQSSEYFGN

251  GRVTEFKYGA  KLGTVVRKWS  GEKMSYLKNW  GEGWGFMPSD  RALVFVDNHD

301  NQRGHGAGGA  SILTFWDARL  YKVAVGFMLA  HPYGFTRVMS  SYRWARNFVN

351  GEDVNDWIGP  PNNNGVIKEV  TINADTTCGN  DWVCEHRWRE  IRNMVWFRNV

401  VDGQPFANWW  DNGSNQVAFG  RGNRGFIVFN  NDDWQLSSTL  QTGLPGGTYC

451  DVISGDKVGN  SCTGIKVYVS  SDGTAQFSIS  NSAEDPFIAI  HAESKL
```

12B) Pancreatin API-19-B (FIG. 33): Chain A, Structure Of Porcine Pancreatic Alpha-Amylase.

Nominal mass (Mr): 55310; Calculated pI value: 5.79; NCBI BLAST search of gi|2780980 against nr; Unformatted sequence string for pasting into other applications; Taxonomy: *Sus scrofa*; Sequence Coverage: 29%; Matched peptides shown in bold.

```
                                                    (SEQ ID NO: 26)
  1  XYAPQTQSGR  TSIVHLFEWR  WVDIALECER  YLGPKGFGGV  QVSPPNENVV

51  VTNPSRPWWE  RYQPVSYKLC  TRSGNENEFR  DMVTRCNNVG  VRIYVDAVIN

101  HMCGSGAAAG  TGTTCGSYCN  PGSREFPAVP  YSAWDFNDGK  CKTASGGIES

151  YNDPYQVRDC  QLVGLLDLAL  EKDYVRSMIA  DYLNKLIDIG  VAGFRIDASK

201  HMWPGDIKAV  LDKLHNLNTN  WFPAGSRPFI  FQEVIDLGGE  AIQSSEYFGN

251  GRVTEFKYGA  KLGTVVRKWS  GEKMSYLKNW  GEGWGFMPSD  RALVFVDNHD

301  NQRGHGAGGA  SILTFWDARL  YKVAVGFMLA  HPYGFTRVMS  SYRWARNFVN

351  GEDVNDWIGP  PNNNGVIKEV  TINADTTCGN  DWVCEHRWRE  IRNMVWFRNV

401  VDGQPFANWW  DNGSNQVAFG  RGNRGFIVFN  NDDWQLSSTL  QTGLPGGTYC

451  DVISGDKVGN  SCTGIKVYVS  SDGTAQFSIS  NSAEDPFIAI  HAESKL
```

12C) Pancreatin API-19-C (FIG. 33): alpha-amylase [*Sus scrofa*].

Nominal mass (Mr): 57050; Calculated pI value: 6.51; NCBI BLAST search of gi|47523476 against nr; Taxonomy: *Sus scrofa*; Sequence Coverage: 45%; Matched peptides shown in bold.

```
                                                    (SEQ ID NO: 27)
  1  MKLFLLLSAF  GFCWAQYAPQ  TQSGRTSIVH  LFEWRWVDIA  LECERYLGPK

51  GFGGVQVSPP  NENIVVTNPS  RPWWERYQPV  SYKLCTRSGN  ENEFRDMVTR

101  CNNVGVRIYV  DAVINHMCGS  GAAAGTGTTC  GSYCNPGNRE  FPAVPYSAWD

151  FNDGKCKTAS  GGIESYNDPY  QVRDCQLVGL  LDLALEKDYV  RSMIADYLNK

201  LIDIGVAGFR  IDASKHMWPG  DIKAVLDKLH  NLNTNWFPAG  SRPFIFQEVI

251  DLGGEAIQSS  EYFGNGRVTE  FKYGAKLGTV  VRKWSGEKMS  YLKNWGEGWG

301  FMPSDRALVF  VDNHDNQRGH  GAGGASILTF  WDARLYKVAV  GFMLAHPYGF

351  TRVMSSYRWA  RNFVNGQDVN  DWIGPPNNNG  VIKEVTINAD  TTCGNDWVCE

401  HRWRQIRNMV  WFRNVVDGQP  FANWWANGSN  QVAFGRGNRG  FIVFNNDDWQ
```

```
451  LSSTLQTGLP GGTYCDVISG DKVGNSCTGI KVYVSSDGTA QFSISNSAED

501  PFIAIHAESK L
```

13) Pancreatin API-21 (FIG. 34): Chain A, Structure Of Porcine Pancreatic Alpha-Amylase. Match to: gi|2780980 Score: 285 Expect: 1.5e-023.

Nominal mass (Mr): 55310; Calculated pI value: 5.79; NCBI BLAST search of gi|2780980 against nr; Unformatted sequence string for pasting into other applications; Taxonomy: *Sus scrofa*; Sequence Coverage: 31%; Matched peptides shown in bold.

```
                                                (SEQ ID NO: 28)
  1  XYAPQTQSGR TSIVHLFEWR WVDIALECER YLGPKGFGGV QVSPPNENVV

51  VTNPSRPWWE RYQPVSYKLC TRSGNENEFR DMVTRCNNVG VRIYVDAVIN

101  HMCGSGAAAG TGTTCGSYCN PGSREFPAVP YSAWDFNDGK CKTASGGIES

151  YNDPYQVRDC QLVGLLDLAL EKDYVRSMIA DYLNKLIDIG VAGFRIDASK

201  HMWPGDIKAV LDKLHNLNTN WFPAGSRPFI FQEVIDLGGE AIQSSEYFGN

251  GRVTEFKYGA KLGTVVRKWS GEKMSYLKNW GEGWGFMPSD RALVFVDNHD

301  NQRGHGAGGA SILTFWDARL YKVAVGFMLA HPYGFTRVMS SYRWARNFVN

351  GEDVNDWIGP PNNNGVIKEV TINADTTCGN DWVCEHRWRE IRNMVWFRNV

401  VDGQPFANWW DNGSNQVAFG RGNRGFIVFN NDDWQLSSTL QTGLPGGTYC

451  DVISGDKVGN SCTGIKVYVS SDGTAQFSIS NSAEDPFIAI HAESKL
```

Figure 35:
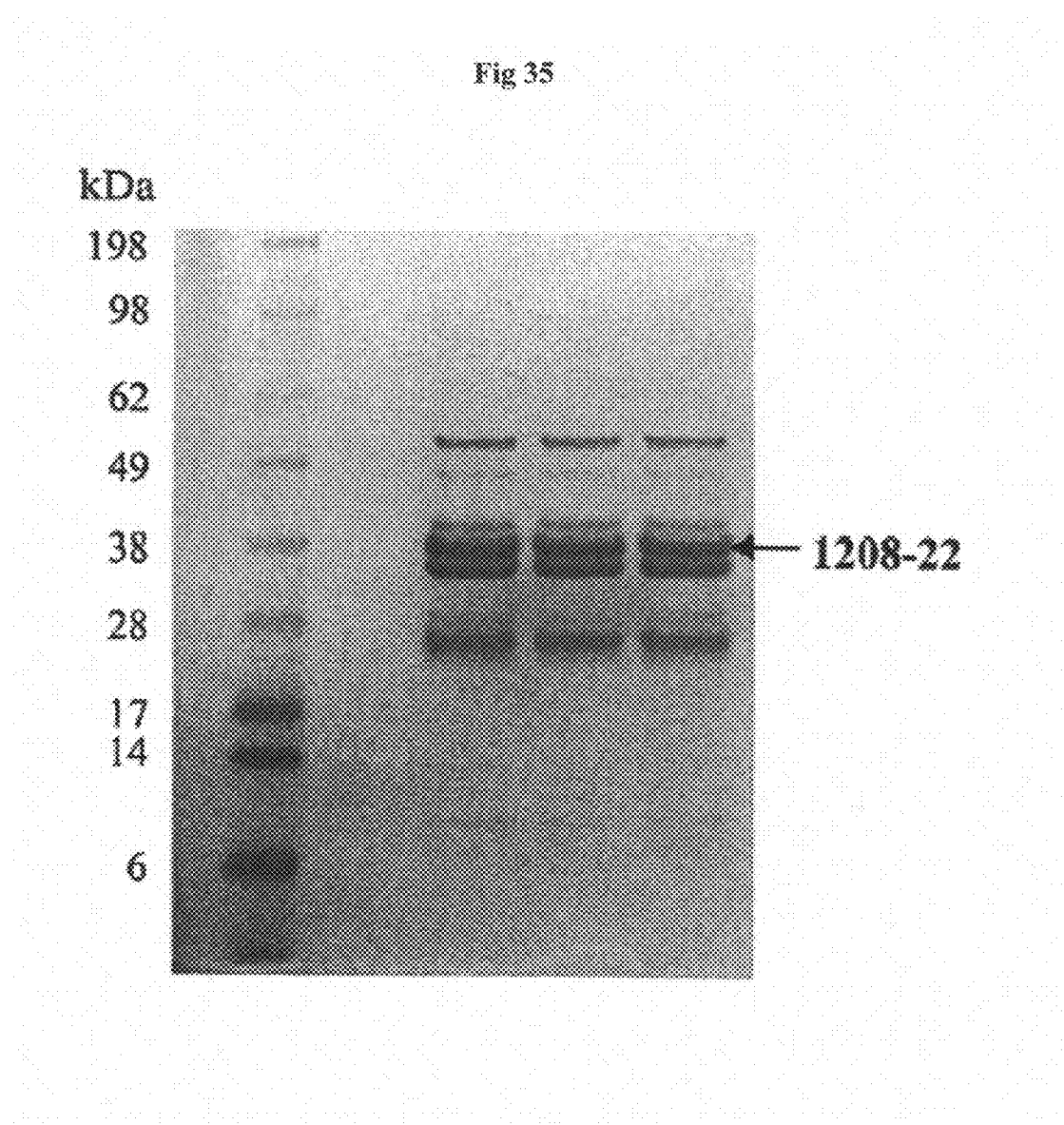
FIG. 35 Western Blot of pancreatin API-22.

14) Pancreatin API-22 (FIG. 35): Carboxypeptidase B. Match to: gi|5457422 Score: 239 Expect: 6.1e-019.

Nominal mass ($M_r$): 47351; Calculated pI value: 5.24; NCBI BLAST search of gi|5457422 against nr; Taxonomy: *Sus scrofa*; Links to retrieve other entries containing this sequence from NCBI Entrez: gi|47523424 from *Sus scrofa*, gi|62906849 from *Sus scrofa*; Sequence Coverage: 43%; Matched peptides shown in bold.

```
                                                (SEQ ID NO: 29)
  1  MLAFLILVTV TLASAHHSGE HFEGEKVFRV NVEDENDISL LHELASTRQI

51  DFWKPDSVTQ IKPHSTVDFR VKAEDILAVE DFLEQNELQY EVLINNLRSV

101  LEAQFDSRVR TTGHSYEKYN NWETIEAWTK QVTSENPDLI SRTAIGTTFL

151  GNNIYLLKVG KPGPNKPAIF MDCGFHAREW ISHAFCQWFV REAVLTYGYE

201  SHMTEFLNKL DFYVLPVLNI DGYIYTWTKN RMWRKTRSTN AGTTCIGTDP

251  NRNFDAGWCT TGASTDPCDE TYCGSAAESE KETKALADFI RNNLSSIKAY

301  LTIHSYSQMI LYPYSYDYKL PENNAELNNL AKAAVKELAT LYGTKYTYGP
```

```
351 GATTIYPAAG GSDDWAYDQG IKYSFTFELR DKGRYGFILP ESQIQATCEE

401 TMLAIKYVTN YVLGHL
```

15A) Pancreatin API-23-A (FIG. 36): alpha-amylase. Match to: gi|47523476 Score: 589 Expect: 6.1e-054; alpha-amylase [*Sus scrofa*].

Nominal mass ($M_r$): 57050; Calculated pI value: 6.51; NCBI BLAST search of gi|47523476 against nr; Taxonomy: *Sus scrofa*; Links to retrieve other entries containing this sequence from NCBI Entrez: gi|6056338 from *Sus scrofa*, gi|33860120 from *Sus scrofa*; Sequence Coverage: 44%; Matched peptides shown in bold.

```
                                                            (SEQ ID NO: 30)
  1 MKLFLLLSAF GFCWAQYAPQ TQSGRTSIVH LFEWRWVDIA LECERYLGPK

51 GFGGVQVSPP NENIVVTNPS RPWWERYQPV SYKLCTRSGN ENEFRDMVTR

101 CNNVGVRIYV DAVINHMCGS GAAAGTGTTC GSYCNPGNRE FPAVPYSAWD

151 FNDGKCKTAS GGIESYNDPY QVRDCQLVGL LDLALEKDYV RSMIADYLNK

201 LIDIGVAGFR IDASKHMWPG DIKAVLDKLH NLNTNWFPAG SRPFIFQEVI

251 DLGGEAIQSS EYFGNGRVTE FKYGAKLGTV VRKWSGEKMS YLKNWGEGWG

301 FMPSDRALVF VDNHDNQRGH GAGGASILTF WDARLYKVAV GFMLAHPYGF

351 TRVMSSYRWA RNFVNGQDVN DWIGPPNNNG VIKEVTINAD TTCGNDWVCE

401 HRWRQIRNMV WFRNVVDGQP FANWWANGSN QVAFGRGNRG FIVFNNDDWQ

451 LSSTLQTGLP GGTYCDVISG DKVGNSCTGI KVYVSSDGTA QFSISNSAED

501 PFIAIHAESK L
```

15B) Pancreatin API-23-B (FIG. 36): Chain A, Porcine Pancreatic Alpha-Amylase. Match to: gi|2780980 Score: 712 Expect: 3.1e-066; Chain A, Structure Of Porcine Pancreatic Alpha-Amylase.

Nominal mass ($M_r$): 55310; Calculated pI value: 5.79; NCBI BLAST search of gi|2780980 against nr; Unformatted sequence string for pasting into other applications; Taxonomy: *Sus scrofa*; Variable modifications: Carbamidomethyl (C), Deamidation (NQ), Oxidation (M); Cleavage by Trypsin: cuts C-term side of KR unless next residue is P; Sequence Coverage: 35%; Matched peptides shown in bold.

```
                                                            (SEQ ID NO: 31)
  1 XYAPQTQSGR TSIVHLFEWR WVDIALECER YLGPKGFGGV QVSPPNENVV

51 VTNPSRPWWE RYQPVSYKLC TRSGNENEFR DMVTRCNNVG VRIYVDAVIN

101 HMCGSGAAAG TGTTCGSYCN PGSREFPAVP YSAWDFNDGK CKTASGGIES

151 YNDPYQVRDC QLVGLLDLAL EKDYVRSMIA DYLNKLIDIG VAGFRIDASK

201 HMWPGDIKAV LDKLHNLNTN WFPAGSRPFI FQEVIDLGGE AIQSSEYFGN

251 GRVTEFKYGA KLGTVVRKWS GEKMSYLKNW GEGWGFMPSD RALVFVDNHD

301 NQRGHGAGGA SILTFWDARL YKVAVGFMLA HPYGFTRVMS SYRWARNFVN

351 GEDVNDWIGP PNNNGVIKEV TINADTTCGN DWVCEHRWRE IRNMVWFRNV
```

```
401 VDGQPFANWW DNGSNQVAFG RGNRGFIVFN NDDWQLSSTL QTGLPGGTYC

451 DVISGDKVGN SCTGIKVYVS SDGTAQFSIS NSAEDPFIAI HAESKL
```

15C) Pancreatin API-23-C (FIG. 36): Chain A, Structure Of Porcine Pancreatic Alpha-Amylase. Match to: gi|2780980 Score: 539 Expect: 6.1e-049; Chain A, Structure Of Porcine Pancreatic Alpha-Amylase.

Nominal mass ($M_r$): 55310; Calculated pI value: 5.79; NCBI BLAST search of gi|2780980 against nr; Unformatted sequence string for pasting into other applications; Taxonomy: *Sus scrofa*; Variable modifications: Carbamidomethyl (C), Deamidation (NQ), Oxidation (M); Cleavage by Trypsin: cuts C-term side of KR unless next residue is P; Sequence Coverage: 37%; Matched peptides shown in bold.

```
                                                    (SEQ ID NO: 32)
  1 XYAPQTQSGR TSIVHLFEWR WVDIALECER YLGPKGFGGV QVSPPNENVV

51 VTNPSRPWWE RYQPVSYKLC TRSGNENEFR DMVTRCNNVG VRIYVDAVIN

101 HMCGSGAAAG TGTTCGSYCN PGSREFPAVP YSAWDFNDGK CKTASGGIES

151 YNDPYQVRDC QLVGLLDLAL EKDYVRSMIA DYLNKLIDIG VAGFRIDASK

201 HMWPGDIKAV LDKLHNLNTN WFPAGSRPFI FQEVIDLGGE AIQSSEYFGN

251 GRVTEFKYGA KLGTVVRKWS GEKMSYLKNW GEGWGFMPSD RALVFVDNHD

301 NQRGHGAGGA SILTFWDARL YKVAVGFMLA HPYGFTRVMS SYRWARNFVN

351 GEDVNDWIGP PNNNGVIKEV TINADTTCGN DWVCEHRWRE IRNMVWFRNV

401 VDGQPFANWW DNGSNQVAFG RGNRGFIVFN NDDWQLSSTL QTGLPGGTYC

451 DVISGDKVGN SCTGIKVYVS SDGTAQFSIS NSAEDPFIAI HAESKL
```

15D) Pancreatin API-23-D (FIG. 36): Carboxypeptidase A1. Match to: gi|47523568 Score: 653 Expect: 2.4e-060; carboxypeptidase A1 precursor [*Sus scrofa*].

Nominal mass ($M_r$): 47206; Calculated pI value: 5.13; NCBI BLAST search of gi|47523568 against nr; Unformatted sequence string for pasting into other applications; Taxonomy: *Sus scrofa*; Links to retrieve other entries containing this sequence from NCBI Entrez: gi|4336196 from *Sus scrofa*, gi|38258878 from *Sus scrofa*; Variable modifications: Carbamidomethyl (C), Deamidation (NQ), Oxidation (M); Cleavage by Trypsin: cuts C-term side of KR unless next residue is P; Sequence Coverage: 38%; Matched peptides shown in bold.

```
                                                    (SEQ ID NO: 33)
  1 MWGLLIFSVL LGGVLAKEDF VGHQVLRISV DDEAQVQKVK ELEDLEHLQL

51 DFWRGPARPG FPIDVRVPFP SIQAVKVFLE AHGIRYTIMI EDVQLLLDEE

101 QEQMFASQGR ARTTSTFNYA TYHTLEEIYD FMDILVAEHP QLVSKLQIGS

151 SYEGRPIYVL KFSTGGNNRP AIWIDTGIHS REWVTQASGV WFAKKITEDY

201 GQDPAFTAIL DNLDIFLEIV TNPDGFAFTH SENRMWRKTR SRTSGSFCVG

251 VDPNRNWDAG FGGAGASSNP CSETYHGKFP NSEVEVKSIV DFVNDHGNIK

301 AFISIHSYSQ LLLYPYGYKT EAPADKDELD QISKSAVAAL TSLYGTKFQY
```

```
351 GSIITTIYQA SGGTIDWTYN QGIKYSFSFE LRDTGRYGFL LPASQIIPTA

401 QETWLALLTI MEHTLNHPY
```

15E) Pancreatin API-23-E (FIG. 36). Match to: gi|355937 Score: 286 Expect: 1.2e-023; elastase 1, pancreatic.

Nominal mass ($M_r$): 28865; Calculated pI value: 8.42; NCBI BLAST search of gi|355937 against nr; Unformatted sequence string for pasting into other applications; Taxonomy: *Sus scrofa domestica*; Sequence Coverage: 38%; Matched peptides shown in bold.

```
                                                    (SEQ ID NO: 34)
  1  MLRLLVVASL VLYGHSTQDF PETNARVVGG TEAQRNSWPS QISLQYRSGS

51  SWAHTCGGTL IRQNWVMTAA HCVDRELTFR VVVGEHNLNQ NDGYEQYVGV

101  QKIVVHPYWN TDDVAAGYDI ALLRLAQSVT LNSYVQLGVL PRAGTILANN

151  SPCYITGWGL TRTNGQLAQT LQQAYLPTVD YAICSSSSYW GSTVKNSMVC

201  AGGDGVRSGC QGDSGGPLHC LVNGQYAVHG VTSFVSRLGC NVTRKPTVFT

251  RVSAYISWIN NVIASN
```

The disclosures of all articles and references, including patents, are incorporated herein by reference. The invention and the manner and process of making and using it are now described in such full, clear, concise and exact terms as to enable any person skilled in the art to which it pertains, to make and use the same. All references cited in this specification are incorporated herein by reference. It is to be understood that the foregoing describes preferred embodiments of the present invention and that modifications may be made therein without departing from the spirit or scope of the present invention.

---

What is claimed is:

1. A method for separating and characterizing proteins in a pancreatin sample comprising:
   a) treating a pancreatin sample with a solvent to afford a soluble protein sample;
   b) fractionating the soluble protein sample using reverse phase-high performance liquid chromatography (RP-HPLC), the RP-HPLC performed on a $C_4$ column, wherein the $C_4$ column is selected from a group consisting of a Vydac 214MS54, 250×4.6 mm, 5 micron column and a water BEH C4, 250×4.6 mm, 3.5 micron column; and wherein the solvent is acetonitrile containing 0.1% trifluoroacetic acid (TFA), the solvent used to elute the fractionated proteins;
   c) collecting each of the fractionated proteins individually; and
   d) characterizing each of the fractionated proteins using MALDI-TOF-MS.

2. The method according to claim 1, wherein the fractionated proteins are characterized by determining molecular weights of said fractionated proteins using SDS-PAGE.

3. The method according to claim 2, wherein further characterization of the fractionated proteins is performed by Western Blot.

4. The method according to claim 2, wherein further characterization of the fractionated proteins is performed by MALDI-TOF-TOF MS.

5. The method according to claim 4, wherein MALDI-TOF-TOF MS determines both accurate peptide mass and peptide sequences of the fractionated proteins.

6. The method according to claim 1, wherein the fractionated proteins are characterized by co-chromatography, the pancreatin sample spiked with commercially-available standards of porcine enzymes, each commercially-available standard of porcine enzyme co-eluting with the fractionated protein identical to it.

7. The method according to claim 6, wherein analysis of the RP-HPLC results in twenty-five major protein peaks.

8. The method according to claim 7, wherein the enzymes are PLA2, lipase, trypsin, elastase, chymotrypsin, Carboxypeptidase-A (CPA), carboxypeptidase-B (CPB) and amylase.

9. The method according to claim 8, wherein PLA2 co-elutes with RP-HPLC peaks 1 and 2, lipase co-elutes with peak 3, trypsin co-elutes with peaks 4-7, elastase co-elutes with peak 15 and amylase co-elutes with peak 19.

10. The method according to claim 1, wherein the eluted proteins are detected at 280 nm.

11. The method according to claim 1, wherein MALDI-TOF-TOF MS determines both accurate peptide mass and peptide sequences of the fractionated proteins.

* * * * *